United States Patent
Nakamura et al.

(10) Patent No.: US 11,555,214 B2
(45) Date of Patent: Jan. 17, 2023

(54) MODIFIED β-GALACTOSIDASE

(71) Applicant: AMANO ENZYME INC., Nagoya (JP)

(72) Inventors: Genichi Nakamura, Kakamigahara (JP); Yuko Kuritani, Kakamigahara (JP); Satoru Ishihara, Kakamigahara (JP); Tetsuya Takahashi, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

(21) Appl. No.: 16/574,149

(22) Filed: Sep. 18, 2019

(65) Prior Publication Data

US 2020/0002739 A1    Jan. 2, 2020

Related U.S. Application Data

(62) Division of application No. 15/022,685, filed as application No. PCT/JP2014/075575 on Sep. 26, 2014, now Pat. No. 10,465,219.

(30) Foreign Application Priority Data

Sep. 30, 2013  (JP) .................. 2013-205097

(51) Int. Cl.
| | | |
|---|---|---|
| *C12N 9/38* | (2006.01) | |
| *C12P 19/14* | (2006.01) | |
| *C12P 19/04* | (2006.01) | |
| *C12P 19/12* | (2006.01) | |

(52) U.S. Cl.
CPC ............. *C12P 19/14* (2013.01); *C12N 9/2471* (2013.01); *C12P 19/04* (2013.01); *C12P 19/12* (2013.01); *C12Y 302/01023* (2013.01)

(58) Field of Classification Search
CPC .............................. C12N 9/2471; C12N 15/52
See application file for complete search history.

(56) References Cited

U.S. PATENT DOCUMENTS

2012/0135468 A1    5/2012 Katase et al.

FOREIGN PATENT DOCUMENTS

| EP | 2439270 A1 | 4/2012 |
|---|---|---|
| WO | 2010/140435 A1 | 12/2010 |

OTHER PUBLICATIONS

Tadasu Urashima et. al., "Recent Advances of the Study on Milk Oligosaccharides of Domestic Farm Animals Including Cows," Kagaku To Seibutsu vol. 50, No. 7. 2012, pp. 498-509.
Jingyuan Song et al., "The Discoidin Domain of Bacillus circulans β-Galactosidase Plays an Essential Role in Repressing Galactooligosaccharide Production," Biosci. Biotechnol Biochem., 77. 2013, pp. 73-79.
Song J. et al., "Bacillus Circulans bga gene for beta galactosidase, complete cds, strain: ATCC 31382," Database DDBJ/EMBL/GenBank, Accession No. AB605256.
International Search Report dated Jan. 6, 2015, issued for PCT/JP2014/075575.
Zahid Mozaffar et al., "Production of trisaccharide from lactose using [beta]-galactosidase from Bacillus circulans modified by glutaraldehyde," Applied Microbiology and Biotechnology, vol. 31, No. 1, Jul. 1, 1989, pp. 59-60. (cited in the Feb. 23, 2017 EP Search Report).
Supplementary European Search Report dated Feb. 23, 2017, issued for the European patent application No. 14850029.1.
Office Action dated May 29, 2018 in connection with Japanese Patent Application 2015-539372.
Song et al., Biosci. Biotechnol. Biochem., 75 (6), pp. 1194-1197, (Year: 2011).

*Primary Examiner* — Richard G Hutson
(74) *Attorney, Agent, or Firm* — Locke Lord LLP

(57) ABSTRACT

The usefulness of β-galactosidases derived from *Bacillus circulans* is further enhanced. A modified β-galactosidase in which one or more amino acids selected from the group consisting of proline 182 (P182), tyrosine 187 (Y187), serine 188 (S188), tryptophan 405 (W405), alanine 406 (A406), glutamine 407 (Q407), tyrosine 449 (Y449), threonine 483 (T483), serine 512 (S512), serine 531 (S531), threonine 533 (T533), serine 534 (S534), asparagine 550 (N550), glutamine 551 (Q551), tryptophan 593 (W593), tyrosine 598 (Y598), proline 602 (P602), proline 604 (P604), tyrosine 609 (Y609), lysine 612 (K612), and tyrosine 615 (Y615), or an amino acid(s) corresponding thereto, has/have been substituted by other amino acid in a β-galactosidase consisting of the amino acid sequence of any of SEQ ID NOs. 1 to 4 or an amino acid sequence having 90% or more identity to the amino acid sequence set forth in any of SEQ ID NOs. 1 to 4.

6 Claims, 13 Drawing Sheets

Specification includes a Sequence Listing.

Fig. 3
(A)
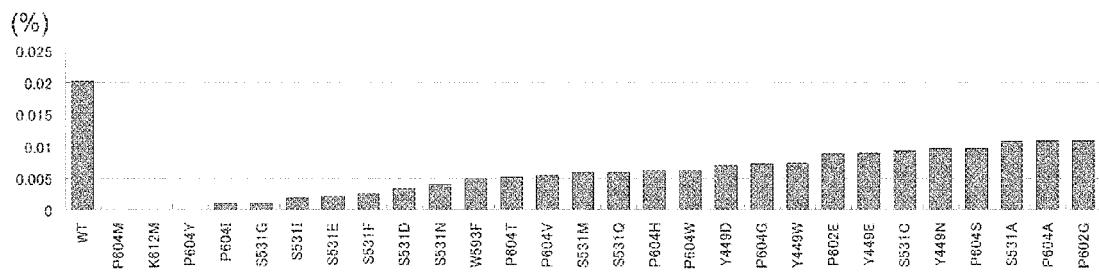
(B)
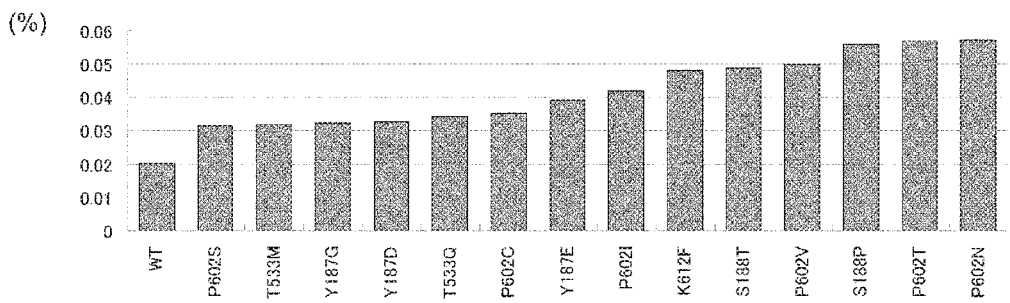

Fig. 4

(A) Mutation sites leading to a decreased saccharide content relative to the wild-type

| | Content of tetrasaccharides (%) | Content of trisaccharides and higher saccharides (%) |
|---|---|---|
| WT | 10.8 | 40.0 |
| S531P | 10.4 | 39.3 |
| W405D | 10.4 | 39.5 |
| S512T | 10.4 | 40.6 |
| W405S | 10.3 | 39.3 |
| P604M | 10.3 | 39.7 |
| W405E | 10.3 | 39.6 |
| Y449I | 10.3 | 39.2 |
| P604I | 10.2 | 39.6 |
| Y449S | 10.2 | 40.2 |
| P602Q | 10.2 | 39.5 |
| W405A | 10.2 | 38.5 |
| P602D | 10.2 | 39.7 |
| Q407R | 10.1 | 40.0 |
| S188I | 10.0 | 39.4 |
| Y449R | 10.0 | 39.7 |
| W405T | 10.0 | 38.5 |
| W405L | 10.0 | 37.6 |
| Y187D | 9.9 | 38.9 |
| W405H | 9.9 | 39.1 |
| W405G | 9.9 | 37.5 |
| Y187L | 9.9 | 39.2 |
| Y449Q | 9.9 | 39.1 |
| N550R | 9.9 | 39.5 |
| Q407G | 9.8 | 38.9 |
| Y449E | 9.8 | 39.4 |
| T483Q | 9.8 | 38.2 |
| N550L | 9.7 | 38.6 |
| P602N | 9.6 | 38.6 |
| S512V | 9.6 | 36.5 |
| N550S | 9.5 | 38.2 |
| W405N | 9.3 | 36.0 |
| S512F | 9.3 | 36.0 |
| P182L | 9.2 | 37.5 |

(B) Mutation sites leading to an increased saccharide content relative to the wild-type

| | Content of tetrasaccharides (%) | Content of trisaccharides and higher saccharides (%) |
|---|---|---|
| WT | 10.8 | 40.0 |
| Y598N | 10.9 | 38.6 |
| Y615T | 11.0 | 39.5 |
| S512K | 11.5 | 37.3 |
| T483K | 11.5 | 39.3 |
| Q551N | 11.6 | 41.0 |
| S512G | 11.6 | 40.1 |
| T483R | 11.8 | 40.6 |
| T483M | 12.0 | 41.9 |

Fig. 5

(A) Mutation sites leading to a decreased saccharide content relative to the wild-type

| | Content of allolactose (%) | Content of trisaccharides and higher saccharides (%) |
|---|---|---|
| WT | 3.58 | 40.2 |
| Y598H | 1.72 | 41.1 |
| Y598F | 1.56 | 39.9 |
| S531D | 1.17 | 40.7 |
| S531L | 1.14 | 40.6 |
| S531M | 1.11 | 40.2 |
| W405D | 1.04 | 39.5 |
| N550F | 0.93 | 40.2 |
| T483M | 0.91 | 42.3 |
| S531K | 0.84 | 40.4 |
| W405S | 0.81 | 39.3 |
| W405T | 0.64 | 38.5 |
| W405A | 0.52 | 38.5 |
| S531F | 0.43 | 39.6 |
| S531G | 0.37 | 39.1 |

(B) Mutation sites leading to an increased saccharide content relative to the wild-type

| | Content of allolactose (%) | Content of trisaccharides and higher saccharides (%) |
|---|---|---|
| WT | 3.58 | 40.2 |
| P602D | 4.03 | 39.7 |
| Y449E | 4.05 | 39.4 |
| Q551H | 4.17 | 38.8 |
| S512T | 4.74 | 40.6 |
| S188E | 4.99 | 39.9 |
| Q407R | 5.02 | 40.0 |
| Y449R | 5.02 | 39.7 |
| N550K | 5.10 | 39.6 |
| S188N | 5.20 | 40.1 |
| S512G | 5.25 | 39.8 |
| N550A | 5.25 | 39.5 |
| Y187N | 5.44 | 39.5 |
| S534K | 5.48 | 40.1 |
| N550M | 5.55 | 38.6 |
| Y187E | 5.56 | 41.2 |
| A406P | 5.80 | 39.7 |
| Y449P | 5.93 | 39.7 |
| Q551K | 5.99 | 39.8 |
| S512V | 6.06 | 36.5 |
| S534Q | 6.08 | 40.4 |
| P182L | 6.15 | 37.6 |
| K612I | 6.26 | 39.2 |
| K612F | 6.32 | 38.8 |
| T483S | 6.42 | 39.8 |
| N550R | 6.48 | 39.5 |
| P602C | 6.57 | 39.3 |
| Y187D | 6.59 | 38.9 |
| S188I | 7.00 | 39.4 |
| Q407K | 7.08 | 39.4 |
| Y609T | 7.23 | 39.3 |
| S188G | 7.38 | 39.2 |
| N550L | 7.53 | 38.6 |
| W405H | 7.60 | 39.1 |
| Q407F | 7.81 | 38.0 |
| N550G | 8.33 | 38.3 |
| T483Q | 8.36 | 38.2 |
| P602N | 8.53 | 38.6 |
| N550S | 8.63 | 38.2 |
| Q407A | 8.77 | 38.8 |
| P182S | 9.59 | 38.7 |
| Y609Q | 9.68 | 38.4 |
| Q407G | 10.19 | 39.3 |

Fig. 6

| | Content of tetrasaccharides (%) | Content of trisaccharides and higher saccharides (%) |
|---|---|---|
| WT | 10.4 | 38.5 |
| W1540F | 10.6 | 39.7 |
| W1540V | 10.6 | 40.2 |
| W1540R | 10.6 | 40.0 |
| W1540L | 10.6 | 40.1 |
| W1540N | 10.6 | 40.4 |
| W1540I | 10.7 | 40.1 |
| W1540M | 10.7 | 40.2 |
| W1540H | 10.7 | 40.1 |
| W1540S | 10.7 | 39.9 |
| W1540C | 10.8 | 39.8 |
| W1540E | 10.8 | 40.4 |
| W1540P | 10.8 | 40.2 |
| W1540A | 10.8 | 40.1 |
| W1540Q | 10.9 | 40.0 |
| W1540T | 10.9 | 40.0 |
| W1540D | 10.9 | 40.3 |
| W1540G | 10.9 | 40.3 |
| W1540K | 11.1 | 40.1 |

Fig. 7

(A) Decreased content of tetrasaccharides

| Mutant | Content of tetrasaccharides (%) | Content of trisaccharides and higher saccharides (%) |
|---|---|---|
| WT | 10.8 | 40.0 |
| S512W | 10.4 | 40.4 |
| E513T | 10.4 | 40.1 |
| G485T | 10.4 | 41.3 |
| G479L | 10.4 | 40.2 |
| G349W | 10.4 | 40.8 |
| D486A | 10.4 | 40.8 |
| S512C | 10.4 | 39.5 |
| N515A | 10.4 | 40.1 |
| G485N | 10.4 | 40.3 |
| S512E | 10.3 | 37.6 |
| N515D | 10.3 | 40.1 |
| Y606D | 10.3 | 39.4 |
| Y598N | 10.3 | 41.5 |
| W186M | 10.3 | 40.9 |
| T483S | 10.3 | 40.0 |
| P182Y | 10.3 | 40.0 |
| N514L | 10.3 | 39.9 |
| K487W | 10.3 | 42.7 |
| K487V | 10.3 | 42.6 |
| K482V | 10.3 | 38.6 |
| F91A | 10.3 | 40.0 |
| D486T | 10.3 | 40.5 |
| D486L | 10.3 | 40.6 |
| G485D | 10.3 | 40.4 |
| N515I | 10.3 | 40.0 |
| N515L | 10.2 | 39.7 |
| E513N | 10.2 | 39.6 |
| E513V | 10.2 | 39.7 |
| N515P | 10.2 | 38.7 |
| N515V | 10.2 | 39.6 |
| E513H | 10.2 | 39.4 |
| Y609S | 10.2 | 39.9 |
| Y609N | 10.2 | 39.9 |
| Y606K | 10.2 | 39.8 |
| Y605I | 10.2 | 40.8 |
| Y605C | 10.2 | 40.9 |
| Y598H | 10.2 | 41.5 |
| Y153G | 10.2 | 39.5 |
| R484N | 10.2 | 39.1 |
| Q407Y | 10.2 | 40.1 |
| Q407V | 10.2 | 40.0 |
| K482M | 10.2 | 39.0 |
| F402G | 10.2 | 39.9 |
| E513L | 10.2 | 40.1 |
| D486E | 10.2 | 40.5 |
| E513K | 10.2 | 39.6 |
| G485Q | 10.2 | 40.0 |
| E513M | 10.2 | 39.4 |
| N515G | 10.1 | 39.7 |
| S512D | 10.1 | 37.1 |
| Y606G | 10.1 | 39.3 |
| Y605T | 10.1 | 40.0 |
| Y605R | 10.1 | 41.0 |
| Y605K | 10.1 | 40.5 |
| V488W | 10.1 | 39.5 |
| S512N | 10.1 | 40.6 |
| G479P | 10.1 | 39.5 |
| F91I | 10.1 | 39.7 |
| F624G | 10.1 | 40.5 |
| D486K | 10.1 | 39.8 |
| S512Q | 10.1 | 38.8 |
| Y606L | 10.0 | 39.3 |
| Y606I | 10.0 | 39.5 |
| Y606H | 10.0 | 39.1 |
| Y606F | 10.0 | 39.5 |
| Y606E | 10.0 | 40.0 |
| Y606C | 10.0 | 39.7 |
| Y518W | 10.0 | 39.4 |
| T533E | 10.0 | 40.4 |
| Q407M | 10.0 | 39.5 |
| Q407L | 10.0 | 39.7 |
| N514E | 10.0 | 38.7 |
| H345G | 10.0 | 38.6 |
| E480N | 10.0 | 38.9 |
| D517K | 10.0 | 39.5 |
| D486M | 10.0 | 40.9 |
| Y609E | 9.9 | 39.3 |
| Y606S | 9.9 | 39.3 |
| T573E | 9.9 | 39.2 |
| K487N | 9.9 | 41.9 |
| K487I | 9.9 | 41.7 |
| E513C | 9.9 | 39.8 |
| V488R | 9.9 | 39.2 |
| E513Q | 9.9 | 38.7 |
| V488T | 9.9 | 39.3 |
| V488Y | 9.8 | 39.2 |
| V488S | 9.8 | 39.1 |
| V488I | 9.8 | 39.1 |
| Y547G | 9.8 | 40.0 |
| R484Q | 9.8 | 41.0 |
| R484M | 9.8 | 38.7 |
| Q407I | 9.8 | 39.2 |
| K487H | 9.8 | 41.2 |
| K487F | 9.8 | 41.1 |
| K487C | 9.8 | 41.1 |
| G479Q | 9.8 | 38.6 |
| D486W | 9.8 | 40.3 |
| V488L | 9.8 | 38.9 |
| V488G | 9.8 | 39.5 |
| E513F | 9.7 | 36.6 |
| Y192G | 9.7 | 39.9 |
| W650G | 9.7 | 39.9 |
| R572Y | 9.7 | 39.6 |
| R572W | 9.7 | 39.8 |
| R572M | 9.7 | 40.0 |
| P182W | 9.7 | 40.0 |
| N514K | 9.7 | 39.2 |
| D517W | 9.7 | 38.6 |
| E513S | 9.7 | 38.6 |
| Y606A | 9.6 | 38.7 |
| W648G | 9.6 | 39.6 |
| R572T | 9.6 | 40.0 |
| F616G | 9.6 | 38.7 |
| S512P | 9.6 | 35.3 |
| Y606M | 9.5 | 38.0 |
| Y605P | 9.5 | 39.1 |
| Y605H | 9.5 | 39.6 |
| Y519G | 9.5 | 39.8 |
| R572L | 9.5 | 39.5 |
| R572C | 9.5 | 39.8 |
| R484I | 9.5 | 38.3 |
| D486R | 9.5 | 39.5 |
| E513P | 9.5 | 37.7 |
| E513R | 9.5 | 36.5 |
| K487Q | 9.4 | 38.8 |
| Y496G | 9.4 | 39.3 |
| Y134G | 9.4 | 39.2 |
| T483G | 9.4 | 38.9 |
| N515E | 9.4 | 39.8 |
| K487T | 9.4 | 38.9 |
| D486P | 9.4 | 39.0 |
| D486F | 9.4 | 39.8 |
| E513A | 9.3 | 37.5 |
| Y605D | 9.3 | 38.5 |
| Y555G | 9.3 | 38.8 |
| Y549G | 9.3 | 38.7 |
| K487Y | 9.3 | 40.0 |
| K487E | 9.3 | 41.5 |
| D486I | 9.3 | 39.8 |
| Y295G | 9.2 | 38.9 |
| Y103G | 9.2 | 38.9 |
| D486Y | 9.2 | 39.8 |
| D486Q | 9.2 | 39.0 |
| E513G | 9.2 | 37.2 |
| K487L | 9.2 | 37.7 |
| E513D | 9.1 | 36.8 |
| W85G | 9.1 | 38.6 |
| R484F | 9.1 | 38.5 |
| K487R | 9.1 | 38.7 |

Fig. 8

(B) Increased content of tetrasaccharides

|  | Content of tetrasaccharides (%) | Content of trisaccharides and higher saccharides (%) |
|---|---|---|
| WT | 10.8 | 40.0 |
| N515K | 11.0 | 41.6 |
| G569V | 11.0 | 40.5 |
| R484D | 11.0 | 40.3 |
| W76G | 11.0 | 40.6 |
| G485T | 11.0 | 41.4 |
| S512L | 11.1 | 38.9 |
| G569K | 11.1 | 40.8 |
| N514D | 11.1 | 40.9 |
| T483W | 11.1 | 41.2 |
| N515R | 11.1 | 41.1 |
| S512M | 11.2 | 39.6 |
| F596G | 11.2 | 40.8 |
| N515Y | 11.2 | 38.7 |
| V488P | 11.3 | 42.5 |
| K487G | 11.3 | 44.5 |
| E480Q | 11.4 | 40.5 |
| G569P | 11.5 | 41.5 |
| N515F | 11.5 | 42.4 |
| N515W | 11.5 | 42.7 |
| R484G | 11.6 | 44.3 |
| R484S | 11.6 | 44.1 |
| R484C | 11.7 | 43.2 |
| G485P | 11.9 | 41.5 |
| K487P | 11.9 | 44.9 |
| R484Y | 11.9 | 42.3 |
| R484A | 12.4 | 43.4 |
| R484K | 12.6 | 41.6 |
| R484P | 12.8 | 43.8 |

Fig. 9

Increased content of tetrasaccharides

|  | Content of tetrasaccharides (%) | Content of trisaccharides and higher saccharides (%) |
| --- | --- | --- |
| WT-A | 10.4 | 38.5 |
| N515K | 10.9 | 42.2 |
| N515W | 11.0 | 41.9 |
| N514W | 11.4 | 42.9 |
| K487P | 12.0 | 42.7 |
| K487G | 12.0 | 44.0 |

Fig. 10

(Ex.1) Decreased contents of tetrasaccharides and allolactose

| | | Content of tetrasaccharides (%) | Content of allolactose (%) | Content of trisaccharides and higher saccharides (%) |
|---|---|---|---|---|
| WT | | 10.8 | 3.58 | 40.0 |
| N550F | P602Q | 10.2 | 2.47 | 39.2 |
| Q407R | N550F | 10.1 | 2.07 | 40.4 |
| S188I | N550F | 10.1 | 0.91 | 39.1 |
| Y449Q | Y598H | 10.0 | 1.05 | 38.2 |

(Ex.3) Decreased content of tetrasaccharides and increased content of allolactose

| | | Content of tetrasaccharides (%) | Content of allolactose (%) | Content of trisaccharides and higher saccharides (%) |
|---|---|---|---|---|
| WT | | 10.8 | 3.58 | 40.0 |
| Q407R | Y449E | 9.7 | 8.08 | 38.2 |

(Ex.4) Increased content of tetrasaccharides and decreased content of allolactose

| | | Content of tetrasaccharides (%) | Content of allolactose (%) | Content of trisaccharides and higher saccharides (%) |
|---|---|---|---|---|
| WT | | 10.8 | 3.58 | 40.0 |
| N550F | Y598N | 11.0 | 2.04 | 41.4 |

(Ex.5-1) Decreased content of tetrasaccharides

| | | Content of tetrasaccharides (%) | Content of trisaccharides and higher saccharides (%) |
|---|---|---|---|
| WT | | 10.8 | 40.0 |
| K487W | D517K | 10.4 | 41.7 |
| P182L | Y449Q | 10.3 | 39.3 |
| S188I | T483E | 10.3 | 40.1 |
| K487W | N515G | 10.3 | 41.9 |
| Q407R | N550S | 10.2 | 40.1 |
| Q407R | T483G | 10.2 | 40.0 |
| P182L | Y449E | 10.2 | 39.9 |
| K487W | D517W | 10.2 | 40.0 |
| S188I | Y449Q | 10.2 | 39.5 |
| Y187L | S512N | 10.1 | 40.1 |
| Q407R | Y449Q | 10.1 | 39.1 |
| Y187L | Y449Q | 10.0 | 39.4 |
| S188I | Q407R | 10.0 | 39.1 |
| Y187L | S512C | 9.8 | 39.1 |
| Q407L | S512V | 9.8 | 38.6 |
| Y449Q | N550S | 9.8 | 38.8 |
| Y187L | Q407R | 9.6 | 38.4 |
| Y187L | S512T | 9.6 | 39.1 |
| K487W | S512T | 9.6 | 39.9 |
| Y187L | Y449E | 9.6 | 38.3 |

(Ex.5-2) Increased content of tetrasaccharides

| | | Content of tetrasaccharides (%) | Content of trisaccharides and higher saccharides (%) |
|---|---|---|---|
| WT | | 10.8 | 40.0 |
| K487P | N515R | 11.0 | 42.3 |

Fig. 11

(A) Decreased content of tetrasaccharides

| | | Content of tetrasaccharides (%) | Content of trisaccharides and higher saccharides (%) |
|---|---|---|---|
| WT | | 10.8 | 40.0 |
| T180V | N550F | 10.4 | 41.4 |
| Y449D | Y598F | 10.4 | 39.9 |
| G485K | D517W | 10.4 | 41.0 |
| G485K | G569W | 10.4 | 40.1 |
| G485K | G571K | 10.4 | 40.3 |
| G485K | R572W | 10.4 | 40.2 |
| R376P | N550W | 10.4 | 40.5 |
| V488W | N514W | 10.4 | 40.2 |
| Y187L | K487A | 10.4 | 42.5 |
| Y449Q | Y615P | 10.4 | 40.2 |
| P182L | R376P | 10.4 | 40.3 |
| T483Q | P602Q | 10.4 | 39.4 |
| T483G | Y615L | 10.4 | 40.0 |
| Y187L | S512A | 10.3 | 40.4 |
| P182W | Y449Q | 10.3 | 39.5 |
| T483G | N550S | 10.3 | 41.1 |
| G485K | Y516W | 10.3 | 41.2 |
| G485W | D517W | 10.3 | 38.8 |
| R484H | K487H | 10.3 | 41.3 |
| V488K | G569K | 10.3 | 40.0 |
| V488K | R572K | 10.3 | 40.3 |
| V488K | T573W | 10.3 | 40.0 |
| R376P | Y449Q | 10.3 | 40.2 |
| Q407R | Y615L | 10.3 | 40.1 |
| T180V | Y187L | 10.2 | 40.1 |
| Q407L | T533E | 10.2 | 39.9 |
| T180V | Q407R | 10.2 | 40.6 |
| Y449Q | Y615G | 10.2 | 39.6 |
| G485K | D517K | 10.2 | 39.8 |
| G485W | Y516W | 10.2 | 40.8 |
| K487A | S512V | 10.2 | 38.8 |
| K487G | N515Q | 10.2 | 42.7 |
| R376P | N550Y | 10.2 | 40.0 |
| R484W | K487D | 10.2 | 40.0 |
| T533E | Y615G | 10.2 | 40.7 |
| V488K | D517K | 10.2 | 39.8 |
| T533E | N550S | 10.2 | 40.1 |
| T180V | S512V | 10.2 | 39.8 |
| T180V | S188I | 10.2 | 40.3 |
| G485K | T573W | 10.1 | 39.9 |
| K487W | T573K | 10.1 | 40.7 |
| V488K | T573K | 10.1 | 40.0 |
| V488W | T573W | 10.1 | 39.9 |
| Y187L | T533N | 10.1 | 39.3 |
| T483G | S512V | 10.1 | 38.4 |
| W570Y | Y615L | 10.1 | 38.3 |
| T180V | Y615P | 10.0 | 39.6 |
| G485W | T573K | 10.0 | 39.6 |
| V488K | G569W | 10.0 | 38.7 |
| V488K | N514K | 10.0 | 39.6 |
| V488K | Y516W | 10.0 | 39.6 |
| S512V | N550S | 10.0 | 39.1 |
| T180V | Y449E | 9.9 | 39.4 |
| Q407R | Y615P | 9.9 | 38.8 |
| G485K | V488W | 9.9 | 39.9 |
| R484W | T573W | 9.9 | 38.6 |
| Q407L | Y615L | 9.9 | 39.2 |
| Q407L | W570Y | 9.8 | 38.0 |
| F91S | Q407M | 9.8 | 39.0 |
| Y449Q | T533E | 9.7 | 38.6 |
| T180V | T483G | 9.6 | 38.7 |
| R376P | S512V | 9.6 | 38.2 |
| E500A | I501A | 9.5 | 38.2 |
| V488K | Y516K | 9.5 | 38.3 |
| R376P | Q407L | 9.4 | 38.2 |
| G485W | T573W | 9.4 | 38.6 |
| K487W | W593F | 9.2 | 39.1 |

(B) Increased content of tetrasaccharides

| | | Content of tetrasaccharides (%) | Content of trisaccharides and higher saccharides (%) |
|---|---|---|---|
| WT | | 10.8 | 40.0 |
| N550S | Y598N | 11.0 | 41.2 |
| R376P | Y598N | 11.0 | 41.4 |
| T180V | Y598N | 11.0 | 41.2 |
| T483G | Y615G | 11.0 | 39.6 |
| F91V | E513G | 11.0 | 41.4 |
| V488W | N515K | 11.0 | 40.8 |
| N550S | Y615L | 11.0 | 39.8 |
| N550S | Y615P | 11.1 | 41.4 |
| K487A | Y615L | 11.1 | 43.9 |
| K487W | N514K | 11.1 | 43.3 |
| K487W | Y516W | 11.1 | 44.0 |
| R484H | K487D | 11.1 | 42.9 |
| R484K | G569K | 11.1 | 40.1 |
| T483G | K487A | 11.1 | 43.5 |
| T483M | K487P | 11.1 | 42.2 |
| P182L | Y615L | 11.1 | 39.8 |
| N550S | Y615G | 11.2 | 39.3 |
| T180V | Y615G | 11.2 | 39.8 |
| K487W | G569K | 11.2 | 39.5 |
| K487Y | N515W | 11.2 | 41.6 |
| V488W | N515W | 11.2 | 40.5 |
| V488Y | N515W | 11.2 | 40.0 |
| Q407L | Y615G | 11.2 | 39.0 |
| Q407L | T483K | 11.3 | 41.6 |
| T180V | T483K | 11.3 | 41.6 |
| G485D | K487H | 11.3 | 43.2 |
| G485K | G569K | 11.3 | 43.5 |
| G485K | K487H | 11.3 | 42.5 |
| K487A | W593F | 11.3 | 44.7 |
| K487Y | N515F | 11.3 | 41.0 |
| R484W | N515K | 11.3 | 41.9 |
| T483G | T533E | 11.3 | 40.6 |
| G485K | N515K | 11.4 | 41.4 |
| K487A | S531A | 11.4 | 44.4 |
| R484K | R572W | 11.4 | 40.4 |
| V488K | N515K | 11.4 | 42.0 |
| Q407L | K487P | 11.5 | 44.9 |
| R484K | E513W | 11.5 | 42.0 |
| Y449E | K487A | 11.5 | 44.2 |
| G485W | N515K | 11.6 | 42.1 |
| R484K | N514K | 11.6 | 42.7 |
| V488K | N515W | 11.6 | 42.2 |
| G485K | N514K | 11.7 | 41.4 |
| R484K | D517W | 11.7 | 38.9 |
| R484K | G571K | 11.7 | 42.2 |
| R484K | Y516K | 11.7 | 42.5 |
| T483M | K487A | 11.7 | 45.9 |
| G485R | K487D | 11.7 | 42.7 |
| K487W | N514W | 11.8 | 43.8 |
| R484K | N514W | 11.8 | 43.4 |
| Y449E | K487P | 11.8 | 43.3 |
| G485W | N515W | 12.1 | 42.1 |
| G485W | E513W | 12.2 | 40.0 |
| R484K | N515K | 12.2 | 44.0 |
| R484K | T573K | 12.2 | 40.9 |
| G485K | N515W | 12.3 | 42.3 |
| R484K | N515W | 12.3 | 43.0 |
| R484K | R572K | 12.4 | 41.6 |
| T483M | K487G | 12.4 | 46.6 |
| R484K | T573W | 12.7 | 42.1 |

Fig. 12

(A) Decreased content of tetrasaccharides

|  | Content of tetrasaccharides (%) | Content of trisaccharides and higher saccharides (%) |
|---|---|---|
| WT | 10.8 | 40.0 |
| G485R_D486R_K487R | 10.4 | 40.2 |
| R484D_G485D_K487D | 10.4 | 40.5 |
| R484A_G485A_K487D | 9.9 | 39.4 |
| R484A_G485A_D486A_K487A | 9.9 | 39.6 |
| R484A_G485A_D486P_K487P | 9.7 | 38.8 |

(B) Increased content of tetrasaccharides

|  | Content of tetrasaccharides (%) | Content of trisaccharides and higher saccharides (%) |
|---|---|---|
| WT | 10.8 | 40.0 |
| R484A_G485A_K487D | 11.1 | 41.9 |
| R484A_G485A_D486A_K487A | 11.2 | 40.9 |
| R484D_G485D_D486R_K487R | 11.4 | 41.2 |
| G485R_D486W_K487W | 11.4 | 42.8 |
| R484D_G485D_D486P_K487P | 11.6 | 42.8 |
| G485R_D486A_K487A | 11.6 | 43.8 |
| R484D_G485D_D486A_K487A | 11.7 | 42.5 |
| G485R_D486P_K487P | 11.8 | 43.2 |
| R484P_G485P_D486R_K487R | 11.9 | 41.6 |
| R484D_G485D_D486W_K487W | 12.3 | 42.1 |
| R484C_D486H_K487R | 12.5 | 42.0 |
| R484A_G485A_D486R_K487R | 13.1 | 41.7 |

Fig. 13

(A) Decreased content of tetrasaccharides

|  | Content of tetrasaccharides (%) | Content of trisaccharides and higher saccharides (%) |
| --- | --- | --- |
| WT | 10.8 | 40.0 |
| Δ484-487 | 10.2 | 39.1 |
| N514-W-W-N515 | 10.1 | 40.7 |
| P604-W-W-Y605 | 10.1 | 39.7 |
| P604-A-A-A-A-Y605 | 10.0 | 39.4 |
| P604-F-F-F-F-Y605 | 10.0 | 38.5 |
| N514-F-F-N515 | 10.0 | 39.9 |

(B) Increased content of tetrasaccharides

|  | Content of tetrasaccharides (%) | Content of trisaccharides and higher saccharides (%) |
| --- | --- | --- |
| WT | 10.8 | 40.0 |
| G485-S-S-S-D486 | 11.0 | 41.5 |
| R484-S-S-S-S-G485 | 11.1 | 41.9 |
| Δ485-486_K487R | 11.1 | 41.4 |
| R484-A-A-A-A-A-A-A-A-G485 | 11.1 | 42.4 |
| R484-S-S-G485 | 11.2 | 42.2 |
| R484-W-W-W-W-G485 | 11.4 | 42.7 |
| R484-A-A-G485 | 11.5 | 43.5 |
| Δ485-486_R484W_K487W | 11.5 | 40.4 |
| R484-A-A-A-A-G485 | 11.5 | 43.3 |
| R484-R-R-R-R-G485 | 11.6 | 41.6 |
| R484-D-D-D-D-D-D-D-D-G485 | 11.6 | 43.1 |
| R484-W-W-G485 | 11.8 | 42.0 |
| R484-P-P-P-P-G485 | 11.9 | 42.6 |
| R484-P-P-G485 | 12.0 | 43.5 |
| R484-P-P-P-P-P-P-P-P-G485 | 12.0 | 43.2 |
| R484-K-K-K-K-K-K-K-K-G485 | 12.0 | 42.3 |
| R484-D-D-D-D-G485 | 12.1 | 44.3 |
| R484-K-K-G485 | 12.1 | 42.3 |
| Δ485-486_R484P_K487P | 12.1 | 42.2 |
| R484-F-F-F-F-F-F-F-F-G485 | 12.2 | 40.6 |
| R484-F-F-G485 | 12.4 | 42.8 |
| R484-R-R-G485 | 12.4 | 41.5 |
| R484-F-F-F-F-G485 | 12.8 | 42.3 |
| Δ485_D486H | 13.0 | 42.4 |

SEQUENCE LISTING

```
<160> NUMBER OF SEQ ID NOS: 8

<210> SEQ ID NO 1
<211> LENGTH: 1737
<212> TYPE: PRT
<213> ORGANISM: Bacillus circulans

<400> SEQUENCE: 1

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80
```

-continued

```
Leu Pro His Asp Trp Ser Ile Glu Leu Asp Phe Asn Lys Asn Ser Leu
                 85                  90                  95

Ala Thr His Glu Gly Gly Tyr Leu Asp Gly Gly Ile Gly Trp Tyr Arg
            100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
            130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
            195                 200                 205

Tyr Gly Thr Phe Val Thr Thr Pro Asn Leu Glu Lys Ser Ile Lys Glu
            210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Gly
            260                 265                 270

Thr Val Thr Pro Phe Glu Gln Asn Thr Val Ile Lys Gln Pro Lys Leu
            275                 280                 285

Trp Ser Ile Asp Lys Pro Tyr Arg Tyr Asn Leu Val Thr Glu Val Ile
290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
            370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
            435                 440                 445

Tyr Asp Thr Thr Asn Ala Ala Gly Val Glu Thr Ala Arg Asn Leu Val
            450                 455                 460

Gly Trp Val Lys Glu Ile Asp Thr Thr Arg Pro Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
```

```
                500             505             510
    Glu Asn Asn Tyr Asp Gly Tyr His Lys Gln Asn Pro Ser Trp Lys Leu
                515             520             525
    Tyr Gly Ser Glu Thr Ser Ser Ala Thr Arg Ser Arg Gly Val Tyr Thr
                530             535             540
    His Pro Tyr Gln Tyr Asn Gln Ser Thr Lys Tyr Ala Asp Leu Gln Gln
    545             550             555             560
    Ser Ser Tyr Asp Asn Asp Tyr Val Gly Trp Gly Arg Thr Ala Glu Asp
                    565             570             575
    Ala Trp Lys Tyr Asp Arg Asp Leu Lys His Ile Ala Gly Gln Phe Ile
                580             585             590
    Trp Thr Gly Phe Asp Tyr Ile Gly Glu Pro Thr Pro Tyr Tyr Asn Ser
                595             600             605
    Tyr Pro Ala Lys Ser Ser Tyr Phe Gly Ala Val Asp Thr Ala Gly Phe
                610             615             620
    Pro Lys Asp Ile Phe Tyr Tyr Gln Ser Gln Trp Lys Lys Glu Pro
    625             630             635             640
    Met Val His Leu Leu Pro His Trp Asn Trp Lys Glu Gly Glu Lys Val
                    645             650             655
    Arg Val Leu Ala Tyr Thr Asn Ala Ser Lys Val Glu Leu Val Leu Asn
                660             665             670
    Gly Glu Ser Leu Gly Glu Lys Asn Tyr Asp Asn Lys Gln Thr Ser Trp
                675             680             685
    Gly Ala Pro Tyr Lys Glu Thr Lys Asp Gly Lys Thr Tyr Leu Glu Trp
                690             695             700
    Ala Val Pro Phe Lys Pro Gly Lys Leu Glu Ala Val Ala Lys Asp Glu
    705             710             715             720
    Asn Gly Lys Val Ile Ala Arg Asp Gln Val Val Thr Ala Gly Glu Pro
                    725             730             735
    Ala Ser Val Arg Leu Thr Ala Asp Arg Lys Val Val Lys Ala Asp Gly
                740             745             750
    Thr Asp Leu Ser Phe Ile Thr Ala Asp Ile Val Asp Ser Lys Gly Ile
                755             760             765
    Val Val Pro Asp Ala Asp His Leu Ile Thr Phe Asn Val Thr Gly Gln
                770             775             780
    Gly Glu Leu Ala Gly Val Asp Asn Gly Asn Ala Ser Ser Val Glu Arg
    785             790             795             800
    Tyr Lys Asp Asn Lys Arg Lys Ala Phe Ser Gly Lys Ala Leu Ala Ile
                    805             810             815
    Val Gln Ser Ser Lys Leu Ser Gly Lys Ile Thr Val His Ala Ser Val
                820             825             830
    Ala Gly Leu Ser Ser Asp Ser Thr Ser Val Phe Thr Val Thr Pro Ala
                835             840             845
    Asp His Asp Lys Lys Ile Val Ala Gly Ile Asp Asp Val Asn Leu Thr
                850             855             860
    Val Asp Val Asn Glu Ala Pro Lys Leu Pro Ser Glu Ile Lys Val Tyr
    865             870             875             880
    Tyr Ser Asp Glu Ser Ala Ala Lys Asn Val Thr Trp Asp Glu Val
                    885             890             895
    Asp Pro Lys Gln Tyr Ser Thr Val Gly Glu Phe Thr Val Glu Gly Ser
                900             905             910
    Val Glu Gly Thr Ser Leu Lys Ala Lys Ala Phe Val Ile Val Lys Gly
                915             920             925
```

-continued

```
Ile Val Ala Val Lys Pro Tyr Ser Thr Ala Thr Lys Val Gly Val Gln
            930             935             940

Pro Val Leu Pro Glu Lys Ala Thr Leu Leu Tyr Ser Asp Gly Thr Thr
945             950             955             960

Lys Gly Ala Thr Val Thr Trp Asp Glu Ile Pro Glu Asp Lys Leu Ala
                965             970             975

Lys Glu Gly Arg Phe Thr Val Glu Gly Ser Val Glu Gly Thr Asp Leu
            980             985             990

Lys Ala Asn Val Tyr Val Arg Val  Thr Asn Glu Val Lys  Ser Val Asn
            995             1000            1005

Ile Met  Leu Gln Glu Gln Gly  Ser Ala Tyr Pro Lys  Leu Glu Ala
     1010            1015            1020

Thr Phe  Thr Asn Pro Ala Asp  Asn Leu Gln His Leu  Asn Asp Gly
     1025            1030            1035

Ile Lys  Ser Tyr Thr Asn Asn  Pro Val Asn Arg Trp  Thr Asn Trp
     1040            1045            1050

Thr Arg  Thr Pro Arg Asp Ala  Gly Asp Ser Ile Thr  Val Asn Phe
     1055            1060            1065

Gly Lys  Lys His Val Ile Asn  Asn Leu Asp Leu Phe  Val Phe Thr
     1070            1075            1080

Asp Ser  Gly Thr Val Val Pro  Glu Lys Ala Glu Val  Gln Tyr Trp
     1085            1090            1095

Asp Gly  Thr Ala Trp Lys Asp  Val Glu Asn Leu Thr  Gln Pro Ser
     1100            1105            1110

Pro Tyr  Val Val Glu Lys Asn  Glu Leu Thr Phe Asp  Ala Val Ala
     1115            1120            1125

Thr Glu  Lys Leu Lys Phe His  Leu Thr Pro Ser Val  Lys Gly Lys
     1130            1135            1140

Phe Leu  Ala Leu Thr Glu Ala  Glu Val Tyr Ala Asp  Gln Ile Val
     1145            1150            1155

Met Gly  Glu Thr Ala Lys Leu  Gln Ser Ile Thr Val  Asn Gly Lys
     1160            1165            1170

Ala Leu  Glu Gly Phe Asp His  Ala Lys Lys Asn Tyr  Glu Leu Val
     1175            1180            1185

Leu Pro  Tyr Gly Ser Glu Leu  Pro Lys Ile Glu Ala  Ala Ala Ala
     1190            1195            1200

Asp Asn  Ala Thr Val Thr Ile  Leu Pro Ala Phe Ser  Tyr Pro Gly
     1205            1210            1215

Thr Ala  Lys Leu Phe Val Thr  Ser Glu Asp Gly Lys  Val Thr Thr
     1220            1225            1230

Glu Tyr  Ser Ile Gly Val Ser  Thr Glu Pro Lys Leu  Val Ser
     1235            1240            1245

Ala Glu  Leu Ser Ala Asp Lys  Thr Asn Val Met Glu  Asp Asp Ile
     1250            1255            1260

Ile Asp  Leu Lys Val Ile Gly  Leu Phe Glu Ser Lys  Glu Lys Ile
     1265            1270            1275

Asp Val  Thr Asp Ser Gln Pro  Thr Tyr Glu Phe Asp  Gln Gln Ile
     1280            1285            1290

Ile Lys  Ile Glu Gly Asn Lys  Leu Tyr Ala Leu Glu  Thr Gly Asn
     1295            1300            1305

Val Lys  Val Lys Val Thr Val  Thr Tyr Lys Gly Val  Ser Val Thr
     1310            1315            1320
```

-continued

```
Thr Pro Ala Leu Glu Phe Thr Ile Ala Lys Asn Pro Ala Pro Lys
1325                1330                1335

Tyr Ile Thr Ser Leu Glu Pro Val Thr Val Val Lys Lys Gly
    1340                1345                1350

Glu Ala Pro Glu Leu Pro Ala Thr Val Val Ala His Tyr Asn Arg
    1355                1360                1365

Gly Ile Pro Arg Asp Val Lys Val Lys Trp Glu Arg Ile Asn Pro
    1370                1375                1380

Ser Lys Tyr Gln Gln Leu Gly Glu Phe Thr Val Ser Gly Met Val
    1385                1390                1395

Glu Gly Thr Asp Ile Lys Ala Gln Ala Lys Val Ile Val Lys Gly
    1400                1405                1410

Ala Val Ala Val Glu Asp Ile Arg Met Ala Val Leu Leu Lys Gln
    1415                1420                1425

Met Pro Gln Leu Pro Gly Lys Val Thr Val Tyr Tyr Ser Asp Gly
    1430                1435                1440

Ala Glu Glu Gln Arg Ala Val Lys Trp Glu Glu Ile Pro Gln Glu
    1445                1450                1455

Glu Leu Glu Asn Val Gly Glu Phe Lys Val Lys Gly Asp Val Asn
    1460                1465                1470

Gly Val Lys Leu Lys Ala Thr Ala Thr Ile Arg Val Thr Asp Glu
    1475                1480                1485

Val Gly Gly Glu Gln Asn Ile Ser Arg Ala Lys Asn Gly Tyr Glu
    1490                1495                1500

Tyr Pro Lys Ala Glu Ala Ser Phe Thr Asn Asn Gly Pro Gly Ser
    1505                1510                1515

Ser Asp Arg Ile Glu Ala Ile Asn Asp Asp Val Ile Ser Tyr Glu
    1520                1525                1530

Ala Asn Pro His Asn Arg Trp Thr Asn Trp Gln Pro Val Pro Arg
    1535                1540                1545

Ala Gly Asp Trp Val Ser Ile Thr Phe Gly Asp Tyr Glu Pro Thr
    1550                1555                1560

Glu Tyr Asp Val Asp Ser Met Glu Ile His Trp Phe Ala Asp His
    1565                1570                1575

Gly Thr Ser Tyr Pro Glu Arg Phe Gln Ile Glu Tyr Lys Ser Gly
    1580                1585                1590

Asp Ser Trp Lys Glu Val Thr Ser Leu Lys Ser Asp Pro Ala Ser
    1595                1600                1605

Pro Ala Leu Gly Lys Ala Asn Val Tyr Ser Phe Asp Arg Val Lys
    1610                1615                1620

Thr Ser Ala Ile Arg Val Lys Met Thr Ala Gln Ala Gly Lys Ser
    1625                1630                1635

Leu Ala Ile Thr Glu Leu Lys Val Phe Ser Lys Trp Pro Lys Ala
    1640                1645                1650

Gly Thr Glu Pro Glu Val Thr Asp Ile Lys Val Gly Gly Lys Ser
    1655                1660                1665

Ile Leu Glu Asp Phe Glu Gln Lys Gly Asp His Tyr Glu Val Thr
    1670                1675                1680

Ile Asp Ala Gly Asp Ala Asn Val Met Pro Lys Ile Asn Val Lys
    1685                1690                1695

Ala Lys Asp Gln Thr Ser Ile Thr Ile Val Pro Ala Val Thr Ser
    1700                1705                1710

Pro Ser Thr Ala Lys Val Ile Ala Lys Ser Glu Asp Gly Lys Lys
```

```
                    1715                1720                1725
        Val Lys Val Tyr Ser Ile His Tyr Lys
            1730                1735

<210> SEQ ID NO 2
<211> LENGTH: 1422
<212> TYPE: PRT
<213> ORGANISM: Bacillus circulans

<400> SEQUENCE: 2

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
    290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350
```

```
Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
    450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
```

-continued

```
            770             775             780
Gly Glu Leu Ala Gly Val Asp Asn Gly Asn Ala Ser Ser Val Glu Arg
785             790             795             800

Tyr Lys Asp Asn Lys Arg Lys Ala Phe Ser Gly Lys Ala Leu Ala Ile
            805             810             815

Val Gln Ser Ser Lys Leu Ser Gly Lys Ile Thr Val His Ala Ser Val
            820             825             830

Ala Gly Leu Ser Ser Asp Ser Thr Ser Val Phe Thr Val Thr Pro Ala
            835             840             845

Asp His Asp Lys Lys Ile Val Ala Gly Ile Asp Asp Val Asn Leu Thr
850             855             860

Val Asp Val Asn Glu Ala Pro Lys Leu Pro Ser Glu Ile Lys Val Tyr
865             870             875             880

Tyr Ser Asp Glu Ser Ala Ala Ala Lys Asn Val Thr Trp Asp Glu Val
            885             890             895

Asp Pro Lys Gln Tyr Ser Thr Val Gly Glu Phe Thr Val Glu Gly Ser
            900             905             910

Val Glu Gly Thr Ser Leu Lys Ala Lys Ala Phe Val Ile Val Lys Gly
            915             920             925

Ile Val Ala Val Lys Pro Tyr Ser Thr Ala Thr Lys Val Gly Val Gln
            930             935             940

Pro Val Leu Pro Glu Lys Ala Thr Leu Leu Tyr Ser Asp Gly Thr Thr
945             950             955             960

Lys Gly Ala Thr Val Thr Trp Asp Glu Ile Pro Glu Asp Lys Leu Ala
            965             970             975

Lys Glu Gly Arg Phe Thr Val Glu Gly Ser Val Glu Gly Thr Asp Leu
            980             985             990

Lys Ala Asn Val Tyr Val Arg Val  Thr Asn Glu Val Lys  Ser Val Asn
            995             1000             1005

Ile Met  Leu Gln Glu Gln Gly  Ser Ala Tyr Pro Lys  Leu Glu Ala
1010             1015             1020

Thr Phe  Thr Asn Pro Ala Asp  Asn Leu Gln His Leu  Asn Asp Gly
1025             1030             1035

Ile Lys  Ser Tyr Thr Asn Asn  Pro Val Asn Arg Trp  Thr Asn Trp
1040             1045             1050

Thr Arg  Thr Pro Arg Asp Ala  Gly Asp Ser Ile Thr  Val Asn Phe
1055             1060             1065

Gly Lys  Lys His Val Ile Asn  Asn Leu Asp Leu Phe  Val Phe Thr
1070             1075             1080

Asp Ser  Gly Thr Val Val Pro  Glu Lys Ala Glu Val  Gln Tyr Trp
1085             1090             1095

Asp Gly  Thr Ala Trp Lys Asp  Val Glu Asn Leu Thr  Gln Pro Ser
1100             1105             1110

Pro Tyr  Val Val Glu Lys Asn  Glu Leu Thr Phe Asp  Ala Val Ala
1115             1120             1125

Thr Glu  Lys Leu Lys Phe His  Leu Thr Pro Ser Val  Lys Gly Lys
1130             1135             1140

Phe Leu  Ala Leu Thr Glu Ala  Glu Val Tyr Ala Asp  Gln Ile Val
1145             1150             1155

Met Gly  Glu Thr Ala Lys Leu  Gln Ser Ile Thr Val  Asn Gly Lys
1160             1165             1170

Ala Leu  Glu Gly Phe Asp His  Ala Lys Lys Asn Tyr  Glu Leu Val
1175             1180             1185
```

Leu Pro Tyr Gly Ser Glu Leu Pro Lys Ile Glu Ala Ala Ala Ala
        1190                1195                1200

Asp Asn Ala Thr Val Thr Ile Leu Pro Ala Phe Ser Tyr Pro Gly
        1205                1210                1215

Thr Ala Lys Leu Phe Val Thr Ser Glu Asp Gly Lys Val Thr Thr
        1220                1225                1230

Glu Tyr Ser Ile Gly Val Ser Thr Glu Glu Pro Lys Leu Val Ser
        1235                1240                1245

Ala Glu Leu Ser Ala Asp Lys Thr Asn Val Met Glu Asp Asp Ile
        1250                1255                1260

Ile Asp Leu Lys Val Ile Gly Leu Phe Glu Ser Lys Glu Lys Ile
        1265                1270                1275

Asp Val Thr Asp Ser Gln Pro Thr Tyr Glu Phe Asp Gln Gln Ile
        1280                1285                1290

Ile Lys Ile Glu Gly Asn Lys Leu Tyr Ala Leu Glu Thr Gly Asn
        1295                1300                1305

Val Lys Val Lys Val Thr Val Thr Tyr Lys Gly Val Ser Val Thr
        1310                1315                1320

Thr Pro Ala Leu Glu Phe Thr Ile Ala Lys Asn Pro Ala Pro Lys
        1325                1330                1335

Tyr Ile Thr Ser Leu Glu Pro Val Thr Val Val Lys Lys Gly
        1340                1345                1350

Glu Ala Pro Glu Leu Pro Ala Thr Val Val Ala His Tyr Asn Arg
        1355                1360                1365

Gly Ile Pro Arg Asp Val Lys Val Lys Trp Glu Arg Ile Asn Pro
        1370                1375                1380

Ser Lys Tyr Gln Gln Leu Gly Glu Phe Thr Val Ser Gly Met Val
        1385                1390                1395

Glu Gly Thr Asp Ile Lys Ala Gln Ala Lys Val Ile Val Lys Gly
        1400                1405                1410

Ala Val Ala Val Glu Asp Ile Arg Met
        1415                1420

<210> SEQ ID NO 3
<211> LENGTH: 1249
<212> TYPE: PRT
<213> ORGANISM: Bacillus circulans

<400> SEQUENCE: 3

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Gly Ile Gly Trp Tyr Arg
            100                 105                 110

Lys Thr Phe Thr Ile Pro Glu Ser Met Lys Gly Lys Arg Ile Ser Leu

-continued

```
            115                 120                 125
Asp Phe Asp Gly Val Tyr Met Asn Ser Thr Thr Tyr Leu Asn Gly Glu
130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
                180                 185                 190

Tyr Arg Asn Val Tyr Leu Thr Val Thr Asp Pro Ile His Val Ala Arg
                195                 200                 205

Tyr Gly Thr Phe Val Thr Thr Pro Asn Leu Glu Lys Ser Ile Lys Glu
                210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Glu Lys Thr Ala Ala Ala Gly
                260                 265                 270

Thr Val Thr Pro Phe Glu Gln Asn Thr Val Ile Lys Gln Pro Lys Leu
                275                 280                 285

Trp Ser Ile Asp Lys Pro Tyr Arg Tyr Asn Leu Val Thr Glu Val Ile
290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
                340                 345                 350

Ala Ala Thr Asn Ala Arg Gly Val Glu Arg Gln Met Gln Ile Met Lys
                355                 360                 365

Asp Met Gly Val Asn Ala Ile Arg Val Thr His Asn Pro Ala Ser Pro
370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
                420                 425                 430

Gly Lys Asn Glu Pro Ala Ile Ile Met Trp Ser Ile Gly Asn Glu Ile
                435                 440                 445

Tyr Asp Thr Thr Asn Ala Ala Gly Val Glu Thr Ala Arg Asn Leu Val
                450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
                500                 505                 510

Glu Asn Asn Tyr Asp Gly Tyr His Lys Gln Asn Pro Ser Trp Lys Leu
                515                 520                 525

Tyr Gly Ser Glu Thr Ser Ser Ala Thr Arg Ser Arg Gly Val Tyr Thr
                530                 535                 540
```

```
His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
            565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
            820                 825                 830

Ala Gly Leu Ser Ser Asp Ser Thr Ser Val Phe Thr Val Thr Pro Ala
        835                 840                 845

Asp His Asp Lys Lys Ile Val Ala Gly Ile Asp Asp Val Asn Leu Thr
    850                 855                 860

Val Asp Val Asn Glu Ala Pro Lys Leu Pro Ser Glu Ile Lys Val Tyr
865                 870                 875                 880

Tyr Ser Asp Glu Ser Ala Ala Ala Lys Asn Val Thr Trp Asp Glu Val
                885                 890                 895

Asp Pro Lys Gln Tyr Ser Thr Val Gly Glu Phe Thr Val Glu Gly Ser
            900                 905                 910

Val Glu Gly Thr Ser Leu Lys Ala Lys Ala Phe Val Ile Val Lys Gly
        915                 920                 925

Ile Val Ala Val Lys Pro Tyr Ser Thr Ala Thr Lys Val Gly Val Gln
    930                 935                 940

Pro Val Leu Pro Glu Lys Ala Thr Leu Leu Tyr Ser Asp Gly Thr Thr
945                 950                 955                 960
```

Lys Gly Ala Thr Val Thr Trp Asp Glu Ile Pro Glu Asp Lys Leu Ala
            965                 970                 975

Lys Glu Gly Arg Phe Thr Val Glu Gly Ser Val Glu Gly Thr Asp Leu
        980                 985                 990

Lys Ala Asn Val Tyr Val Arg Val Thr Asn Glu Val Lys Ser Val Asn
        995                 1000                1005

Ile Met Leu Gln Glu Gln Gly Ser Ala Tyr Pro Lys Leu Glu Ala
    1010                1015                1020

Thr Phe Thr Asn Pro Ala Asp Asn Leu Gln His Leu Asn Asp Gly
    1025                1030                1035

Ile Lys Ser Tyr Thr Asn Asn Pro Val Asn Arg Trp Thr Asn Trp
    1040                1045                1050

Thr Arg Thr Pro Arg Asp Ala Gly Asp Ser Ile Thr Val Asn Phe
    1055                1060                1065

Gly Lys Lys His Val Ile Asn Asn Leu Asp Leu Phe Val Phe Thr
    1070                1075                1080

Asp Ser Gly Thr Val Val Pro Glu Lys Ala Glu Val Gln Tyr Trp
    1085                1090                1095

Asp Gly Thr Ala Trp Lys Asp Val Glu Asn Leu Thr Gln Pro Ser
    1100                1105                1110

Pro Tyr Val Val Glu Lys Asn Glu Leu Thr Phe Asp Ala Val Ala
    1115                1120                1125

Thr Glu Lys Leu Lys Phe His Leu Thr Pro Ser Val Lys Gly Lys
    1130                1135                1140

Phe Leu Ala Leu Thr Glu Glu Val Tyr Ala Asp Gln Ile Val
    1145                1150                1155

Met Gly Glu Thr Ala Lys Leu Gln Ser Ile Thr Val Asn Gly Lys
    1160                1165                1170

Ala Leu Glu Gly Phe Asp His Ala Lys Lys Asn Tyr Glu Leu Val
    1175                1180                1185

Leu Pro Tyr Gly Ser Glu Leu Pro Lys Ile Glu Ala Ala Ala Ala
    1190                1195                1200

Asp Asn Ala Thr Val Thr Ile Leu Pro Ala Phe Ser Tyr Pro Gly
    1205                1210                1215

Thr Ala Lys Leu Phe Val Thr Ser Glu Asp Gly Lys Val Thr Thr
    1220                1225                1230

Glu Tyr Ser Ile Gly Val Ser Thr Glu Glu Pro Lys Leu Val Ser
    1235                1240                1245

Ala

<210> SEQ ID NO 4
<211> LENGTH: 847
<212> TYPE: PRT
<213> ORGANISM: Bacillus circulans

<400> SEQUENCE: 4

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

```
Gly Ala Gln Asn Pro Gly Phe Asp Asp Ser Ser Trp Arg Lys Leu Asn
 65                  70                  75                  80

Leu Pro His Asp Trp Ser Ile Glu Leu Asp Phe Asn Lys Asn Ser Leu
             85                  90                  95

Ala Thr His Glu Gly Gly Tyr Leu Asp Gly Ile Gly Trp Tyr Arg
        100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
        130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
            165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
        210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
        290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
        370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
        450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
```

```
            485                 490                 495
Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
            820                 825                 830

Ala Gly Leu Ser Ser Asp Ser Thr Ser Val Phe Thr Val Thr Pro
        835                 840                 845

<210> SEQ ID NO 5
<211> LENGTH: 5214
<212> TYPE: DNA
<213> ORGANISM: Bacillus circulans

<400> SEQUENCE: 5
gtgaaaaaag cgattagctg cgttttttta atttcagcac tgattctatc aagctttcaa        60
gtccctgtac agggacaagc catgtcaaaa acgacatcgg cagcaggaaa cagtgtgagc       120
```

```
tatgatggag agagacgagt gaattttaac gagaattggc gatttcaacg agaaaccaat      180
ggaagtattg ccggagcaca gaatcctggc tttgacgatt cctcctggcg gaaattaaat      240
ctgccgcatg actggagtat tgaattagat tttaataaaa attctcttgc cacacatgaa      300
ggcggttatt tggacggcgg aatcggctgg taccgaaaaa cctttacaat cccggaatcg      360
atgaagggaa aacgaatttc gcttgatttt gatggcgttt acatgaacag caccacctat      420
ctaaacgggg aagtgctcgg gacctatccg tttggttata atgccttttc ctatgatatt      480
tccgacaaac tttataaaga tggcagggcg aatgtccttg ttgtcaaagt caataacacc      540
cagccgagca gccgctggta ttcggggagc gggatctacc ggaatgtcta tctcactgtg      600
accgatccca tccatgtggc tcgctacgga acatttgtga caacacccaa tttagagaaa      660
tcgataaaag aagacagggc tgatgtgaac atcaagacga aaatcagtaa cgatgctgct      720
gaggcgaaac aggtaaagat taaatcaacc atctacgatg gggctgggaa caccgtacag      780
acagtggaaa cggaggaaaa aacagctgcc gccggcacgg tgactccgtt cgaacaaaac      840
acagtcatca agcagccgaa gctttggagc attgacaagc cttatcgata taaccttgtt      900
acagaagtca tcgttggcgg gcaaacggtg gatacgtatg aaacaaaatt tggtgtcagg      960
tatttcaaat ttgatgaaaa cgaaggcttt tccttaaatg gagagtatat gaagctgcac     1020
ggcgtttcga tgcaccatga tttagggcgc cttggggcgg caacgaatgc acgcggcgtg     1080
gaaagacaaa tgcagattat gaaggatatg ggggtcaatg ccatcagggt tacccacaac     1140
ccggcatcac cggaactgct ggaggcagct aataaaattag gctattcat catcgaggag     1200 gcatttgaca gctgggccca gtcaaagaaa ccctatgact atggccgttt tttcaatgca     1260
tgggctgagc acgacattaa ggaaatggtc gatcggggca aaaacgaacc agctattatc     1320
atgtggtcga tcggaaatga aatatatgat acgaccaatg ccgctggtgt ggaaacagca     1380
cgaaatttag tgggttgggt aaaagaaatt gacaccacaa ggccgacaac gatcggcgag     1440
gataaaaccc gcgagacaa agtaaatgtt acacctatca acagctacat caaggagatt     1500
tttaatattg tcgatgtggt cggactgaac tacagcgaga caactatga tggctaccac     1560 aagcagaatc cgtcatggaa gctgtacggc tcggagacgt cctcggcaac ccgttcgcgt     1620
ggtgtctaca cgcatccgta ccagtataac caaagcacaa agtatgctga tttacagcaa     1680
tcctcttatg acaatgacta tgtcggctgg ggacgaactg cagaagatgc atggaaatat     1740
gaccgcgacc tgaagcatat tgcagggcaa tttatctgga ccggctttga ttatattggc     1800
gagccgacgc catattataa ttcctatcct gcaaaaagct cctatttggg tgctgtggat     1860
acggctggtt ttccaaagga tattttctac tattaccaaa gccaatggaa aaaggagcct     1920
atggtccacc tgctgccgca ttggaactgg aaggaagggg aaaaggtccg cgtcttagct     1980
tataccaatg caagtaaggt tgaacttgtt ctaaatggtg aatcgttagg ggagaagaac     2040
tatgacaaca aacaaacctc ctggggagca ccatacaaag aaacaaagga tggaaaaacc     2100
tatttggagt gggccgtacc atttaaaccg ggcaaattag aagccgtcgc caaggatgaa     2160
aacggcaaag tgatcgcccg cgatcaggta gtgaccgctg gtgagccagc ctctgtcaga     2220
ttaacggctg atcgtaaggt ggtcaaggcg gacggtacga atctgtcgtt tattacagca     2280
gacattgttg atagtaaagg gattgttgtc ccggatgccg atcatctgat tacatttaac     2340
gtaacgggcc aaggggaatt ggccgggggtt gataacggaa acgcgtccag tgtggagcgt     2400
tacaaggaca acaagcgcaa ggctttcagc gggaaagcat tggcgattgt tcaatcaagt     2460
```

```
aagctttctg gaaaaattac ggtccatgcg tcagtggcag ggctttcgag cgattccacg   2520
agcgtattta cggtaacgcc agctgaccat gacaaaaaga ttgtagctgg gattgatgat   2580
gttaacctta ctgtcgatgt caatgaagca ccaaagcttc cttcagaaat caaggtttat   2640
tacagtgatg agagtgcagc tgcgaagaat gtgacttggg atgaggtgga tccaaagcag   2700
tacagcactg ttggtgaatt cacagtggaa ggcagtgtcg agggaacttc gctgaaggca   2760
aaggcatttt ttattgtcaa aggaattgtc gccgtcaagc cttattcaac ggcaacaaag   2820
gttggtgtac agccggtgct gcctgaaaaa gcaacccttc tttacagtga tggaacaacc   2880
aagggagcaa ctgtcacgtg ggatgagatc cctgaggaca agctggcaaa gagggccgg   2940 tttaccgtcg agggcagtgt ggagggaaca gacctcaagg ctaatgtcta tgtcagggtg   3000
acaaatgaag taaaatcagt gaatattatg cttcaggagc agggttcagc ttatccaaag   3060
ctcgaagcta cttttaccaa tccagctgac aatcttcagc atttgaacga tggcatcaag   3120
agctatacca ataaccccggt caaccgctgg acgaactgga caagaacacc gcgtgatgct   3180
ggtgactcga ttacagttaa ttttggcaag aagcatgtga ttaataatct agatttattt   3240 gttttaccg acagcggcac ggtggttcca gaaaaggcag aggtccaata ttgggatgga   3300
acggcgtgga aggatgtcga aaatctaaca cagccatcgc catatgtggt agagaaaaat   3360
gaacttacat ttgatgcggt cgcgacagaa aagctgaaat tccatttgac accatctgtg   3420
aaagggaaat tcctagctct aacgaagca gaggtgtacg ccgatcagat tgtgatgggt   3480
gaaacagcaa aacttcaaag tattacggtg aatgggaaag cattagaagg ctttgatcac   3540
gctaaaaaga attatgaact tgtacttcca tatggaagcg agcttcctaa gattgaggcg   3600
gctgctgccg acaatgcaac tgtcaccatt ttaccggcat tctcctatcc gggaacagca   3660
aaactatttg tcacttcaga ggatgggaag gtaactactg agtacagtat tggtgtttct   3720
acagaagagc caaagctcgt ctccgcagag ttatccgcgg acaagacgaa tgtcatggag   3780
gacgatatca tcgatctgaa ggtaattggt ctcttcgaaa gcaaggaaaa gattgatgtg   3840
accgacagcc agccgacata tgaatttgac cagcagatta ttaaaattga aggcaataag   3900
ctgtatgcgc tggaaacagg aaatgtcaag gtgaaagtga cggtgacata aagggtgtg   3960 agtgtcacaa cacctgcgct tgagtttacg atcgcgaaaa accctgctcc aaaatacatt   4020
acgagcttag agcctgtcac ggttgttgtt aaaaaaggag aagcgccgga gcttccagca   4080
acggttgtgg cccattataa ccgaggaatc ccgcgggatg ttaaggtgaa gtgggaaaga   4140
atcaatccgt ctaagtacca gcagctaggc gagtttaccg tatctggcat ggtgaaaggg   4200
accgatataa aagcccaagc aaaagtgatt gtaaaagggg ctgttgcggt cgaggatatt   4260
agaatggctg tgctgttaaa gcaaatgcca cagctgccgg gcaaggttac agtctattat   4320
agtgacggag cggaagaaca aagagcggtc aagtgggagg aaatcccgca ggaggaactc   4380
gagaatgtcg gtgaatttaa ggttaaaggt gatgttaatg gagtgaagct gaaagcaaca   4440
gccactattc gagtaaccga tgaagtcggc ggcgagcaga atatcagccg ggctaaaaat   4500
ggttatgaat acccgaaggc tgaagcttcc tttaccaaca atggccctgg atcaagcgat   4560
cgaatcgagg ccatcaatga tgacgtgatc tcctacgagg ctaatccgca taatcgctgg   4620
acgaattggc agccggtacc gcgtgcaggg gactgggttt ctatcaccctt tggagactat   4680 gagcctacgg aatatgatgt tgatagcatg gagatccact ggttcgcgga tcatgggacc   4740
tcgtatccag agcgtttcca aatcgaatat aaatccggtg atagctggaa ggaagtcacc   4800
agcctgaaaa gcgatccagc ctctccggcc ttgggtaagg caaatgtcta tagctttgat   4860
```

-continued

| | |
|---|---|
| cgagtaaaaa catcggctat acgagtgaaa atgacagcac aagccggcaa aagcttagcc | 4920 |
| attaccgagc tgaaagtatt ttcaaaatgg ccaaaggcag gtaccgaacc agaggtgacc | 4980 |
| gatattaagg tcggaggaaa atcgattctg gaggactttg aacaaaaagg cgatcactat | 5040 |
| gaagtaacga ttgatgcagg agatgcgaat gtaatgccga aaatcaatgt aaaggctaag | 5100 |
| gaccagacga gtattacgat tgtgccagca gttacctctc catccacggc aaaggtaatt | 5160 |
| gctaaatccg aggatggcaa gaaagtgaag gtctatagca ttcactataa ataa | 5214 |

<210> SEQ ID NO 6
<211> LENGTH: 4266
<212> TYPE: DNA
<213> ORGANISM: Bacillus circulans

<400> SEQUENCE: 6

| | |
|---|---|
| gtgaaaaaag cgattagctg cgttttttta atttcagcac tgattctatc aagctttcaa | 60 |
| gtccctgtac agggacaagc catgtcaaaa acgacatcgg cagcaggaaa cagtgtgagc | 120 |
| tatgatggag agagacgagt gaattttaac gagaattggc gatttcaacg agaaaccaat | 180 |
| ggaagtattg ccgagcaca gaatcctggc tttgacgatt cctcctggcg gaaattaaat | 240 |
| ctgccgcatg actggagtat tgaattagat tttaataaaa attctcttgc cacacatgaa | 300 |
| ggcggttatt tggacggcgg aatcggctgg taccgaaaaa cctttacaat cccggaatcg | 360 |
| atgaagggaa aacgaatttc gcttgatttt gatggcgttt acatgaacag caccacctat | 420 |
| ctaaacgggg aagtgctcgg gacctatccg tttggttata tgcctttttc ctatgatatt | 480 |
| tccgacaaac tttataaaga tggcagggcg aatgtccttg ttgtcaaagt caataacacc | 540 |
| cagccgagca gccgctggta ttcggggagc gggatctacc ggaatgtcta tctcactgtg | 600 |
| accgatccca tccatgtggc tcgctacgga acatttgtga caacacccaa tttagagaaa | 660 |
| tcgataaaag aagacagggc tgatgtgaac atcaagacga aatcagtaa cgatgctgct | 720 |
| gaggcgaaac aggtaaagat taaatcaacc atctacgatg gggctgggaa caccgtacag | 780 |
| acagtggaaa cggaggaaaa aacagctgcc gccggcacgg tgactccgtt cgaacaaaac | 840 |
| acagtcatca agcagccgaa gctttggagc attgacaagc cttatcgata taaccttgtt | 900 |
| acagaagtca tcgttggcgg gcaaacggtg gatacgtatg aaacaaaatt tggtgtcagg | 960 |
| tatttcaaat ttgatgaaaa cgaaggcttt tccttaaatg gagagtatat gaagctgcac | 1020 |
| ggcgtttcga tgcaccatga tttagggcg cttgggcgg caacgaatgc acgcggcgtg | 1080 |
| gaaagacaaa tgcagattat gaaggatatg ggggtcaatg ccatcagggt tacccacaac | 1140 |
| ccggcatcac cggaactgct ggaggcagct aataaattag gctattcat catcgaggag | 1200 |
| gcatttgaca gctgggccca gtcaaagaaa ccctatgact atggccgttt tttcaatgca | 1260 |
| tgggctgagc acgacattaa ggaaatggtc gatcggggca aaaacgaacc agctattatc | 1320 |
| atgtggtcga tcggaaatga aatatatgat acgaccaatg ccgctggtgt ggaaacagca | 1380 |
| cgaaatttag tgggttgggt aaaagaaatt gacaccacaa ggccgacaac gatcggcgag | 1440 |
| gataaaaccc gcggagacaa agtaaatgtt acacctatca acagctacat caaggagatt | 1500 |
| tttaatattg tcgatgtggt cggactgaac tacagcgaga caactatga tggctaccac | 1560 |
| aagcagaatc cgtcatggaa gctgtacggc tcggagacgt cctcggcaac ccgttcgcgt | 1620 |
| ggtgtctaca cgcatcccgta ccagtataac caaagcacaa agtatgctga tttacagcaa | 1680 |
| tcctcttatg acaatgacta tgtcggctgg ggacgaactg cagaagatgc atggaaatat | 1740 |

```
gaccgcgacc tgaagcatat tgcagggcaa tttatctgga ccggctttga ttatattggc   1800
gagccgacgc catattataa ttcctatcct gcaaaaagct cctattttgg tgctgtggat   1860
acggctggtt ttccaaagga tattttctac tattaccaaa gccaatggaa aaaggagcct   1920
atggtccacc tgctgccgca ttggaactgg aaggaagggg aaaaggtccg cgtcttagct   1980
tataccaatg caagtaaggt tgaacttgtt ctaaatggtg aatcgttagg ggagaagaac   2040
tatgacaaca acaaacctc ctggggagca ccatacaaag aaacaaagga tggaaaaacc   2100
tatttggagt gggccgtacc atttaaaccg gcaaattag aagccgtcgc caaggatgaa   2160
aacggcaaag tgatcgcccg cgatcaggta gtgaccgctg gtgagccagc ctctgtcaga   2220
ttaacggctg atcgtaaggt ggtcaaggcg gacggtacgg atctgtcgtt tattacagca   2280
gacattgttg atagtaaagg gattgttgtc ccggatgccg atcatctgat tacatttaac   2340
gtaacgggcc aaggggaatt ggccgggstt gataacggaa acgcgtccag tgtggagcgt   2400
tacaaggaca caagcgcaa ggctttcagc gggaaagcat tggcgattgt tcaatcaagt   2460
aagctttctg gaaaaattac ggtccatgcg tcagtggcag ggctttcgag cgattccacg   2520
agcgtattta cggtaacgcc agctgaccat gacaaaaaga ttgtagctgg gattgatgat   2580
gttaacctta ctgtcgatgt caatgaagca ccaaagcttc cttcagaaat caaggtttat   2640
tacagtgatg agagtgcagc tgcgaagaat gtgacttggg atgaggtgga tccaaagcag   2700
tacagcactg ttggtgaatt cacagtggaa ggcagtgtcg agggaacttc gctgaaggca   2760
aaggcatttg ttattgtcaa aggaattgtc gccgtcaagc cttattcaac ggcaacaaag   2820
gttggtgtac agccggtgct gcctgaaaaa gcaacccttc tttacagtga tggaacaacc   2880
aagggagcaa ctgtcacgtg ggatgagatc cctgaggaca agctggcaaa agagggccgg   2940
tttaccgtcg agggcagtgt ggagggaaca gacctcaagg ctaatgtcta tgtcaggggtg   3000 acaaatgaag taaaatcagt gaatattatg cttcaggagc agggttcagc ttatccaaag   3060
ctcgaagcta cttttaccaa tccagctgac aatcttcagc atttgaacga tggcatcaag   3120
agctatacca ataacccggt caaccgctgg acgaactgga caagaacacc gcgtgatgct   3180
ggtgactcga ttcagttaa ttttggcaag aagcatgtga ttaataatct agatttattt   3240 gttttttaccg acagcggcac ggtggttcca gaaaaggcag aggtccaata ttgggatgga   3300
acggcgtgga aggatgtcga aaatctaaca cagccatcgc catatgtggt agagaaaaat   3360
gaacttacat ttgatgcggt cgcgacagaa aagctgaaat tccatttgac accatctgtg   3420
aaagggaaat tcctagctct aacggaagca gaggtgtacg ccgatcagat tgtgatgggt   3480
gaaacagcaa aacttcaaag tattacggtg aatgggaaag cattagaagg ctttgatcac   3540
gctaaaaaga attatgaact tgtacttcca tatggaagcg agcttcctaa gattgaggcg   3600
gctgctgccg acaatgcaac tgtcaccatt ttaccggcat tctcctatcc gggaacagca   3660
aaactatttg tcacttcaga ggatgggaag gtaactactg agtacagtat tggtgtttct   3720
acagaagagc caaagctcgt ctccgcagag ttatccgcgg acaagacgaa tgtcatggag   3780
gacgatatca tcgatctgaa ggtaattggt ctcttcgaaa gcaaggaaaa gattgatgtg   3840
accgacagcc agccgacata tgaatttgac cagcagatta ttaaaattga aggcaataag   3900
ctgtatgcgc tggaaacagg aaatgtcaag gtgaaagtga cggtgacata aagggtgtg   3960 agtgtcacaa cacctgcgct tgagtttacg atcgcgaaaa accctgctcc aaaatacatt   4020
acgagcttag agcctgtcac ggttgttgtt aaaaaaggag aagcgccgga gcttccagca   4080
acggttgtgg cccattataa ccgaggaatc ccgcgggatg ttaaggtgaa gtgggaaaga   4140
```

```
atcaatccgt ctaagtacca gcagctaggc gagtttaccg tatctggcat ggtggaaggg   4200
accgatataa aagcccaagc aaaagtgatt gtaaaagggg ctgttgcggt cgaggatatt   4260
agaatg                                                              4266

<210> SEQ ID NO 7
<211> LENGTH: 3747
<212> TYPE: DNA
<213> ORGANISM: Bacillus circulans

<400> SEQUENCE: 7
gtgaaaaaag cgattagctg cgttttttta atttcagcac tgattctatc aagctttcaa     60
gtccctgtac agggacaagc catgtcaaaa acgacatcgg cagcaggaaa cagtgtgagc    120
tatgatggag agagacagt gaattttaac gagaattggc gatttcaacg agaaaccaat    180
ggaagtattg ccggagcaca gaatcctggc tttgacgatt cctcctggcg gaaattaaat    240
ctgccgcatg actggagtat tgaattagat tttaataaaa attctcttgc cacacatgaa    300
ggcggttatt tggacggcgg aatcggctgg taccgaaaaa cctttacaat cccggaatcg    360
atgaagggaa aacgaatttc gcttgatttt gatggcgttt acatgaacag caccaccctat   420 ctaaacgggg aagtgctcgg gacctatccg tttggttata atgccttttc ctatgatatt    480
tccgacaaac tttataaaga tggcagggcg aatgtccttg ttgtcaaagt caataacacc    540
cagccgagca gccgctggta ttcggggagc gggatctacc ggaatgtcta tctcactgtg    600
accgatccca tccatgtggc tcgctacgga acatttgtga caacacccaa tttagagaaa    660
tcgataaaag aagacagggc tgatgtgaac atcaagacga aaatcagtaa cgatgctgct    720
gaggcgaaac aggtaaagat taaatcaacc atctacgatg gggctgggaa caccgtacag    780
acagtggaaa cggaggaaaa aacagctgcc gccggcacgg tgactccgtt cgaacaaaac    840
acagtcatca gcagccgaa gctttggagc attgacaagc cttatcgata taaccttgtt    900
acagaagtca tcgttggcgg gcaaacggtg gatacgtatg aaacaaaatt tggtgtcagg    960
tatttcaaat ttgatgaaaa cgaaggcttt tccttaaatg gagagtatat gaagctgcac   1020
ggcgtttcga tgcaccatga tttaggggcg cttggggcgg caacgaatgc acgcggcgtg   1080
gaaagacaaa tgcagattat gaaggatatg ggggtcaatg ccatcagggt tacccacaac   1140
ccggcatcac cggaactgct ggaggcagct aataaattag gctattcat catcgaggag   1200 gcatttgaca gctgggccca gtcaaagaaa ccctatgact atggccgttt tttcaatgca   1260
tgggctgagc acgacattaa ggaaatggtc gatcggggca aaaacgaacc agctattatc   1320
atgtggtcga tcggaaatga aatatatgat acgaccaatg ccgctggtgt ggaaacagca   1380
cgaaatttag tgggttgggt aaaagaaatt gacaccacaa ggccgacaac gatcggcgag   1440
gataaaaccc gcggagacaa agtaaatgtt acacctatca acagctacat caaggagatt   1500
tttaatattg tcgatgtggt cggactgaac tacagcgaga caactatga tggctaccac   1560 aagcagaatc cgtcatggaa gctgtacggc tcggagacgt cctcggcaac ccgttcgcgt   1620
ggtgtctaca cgcatccgta ccagtataac caaagcacaa agtatgctga tttacagcaa   1680
tcctcttatg acaatgacta tgtcggctgg ggacgaactg cagaagatgc atggaaatat   1740
gaccgcgacc tgaagcatat tgcagggcaa tttatctgga ccggctttga ttatattggc   1800
gagccgacgc catattataa ttcctatcct gcaaaaagct cctatttggg tgctgtggat   1860
acggctggtt ttccaaagga tatttctac tattaccaaa gccaatggaa aaaggagcct   1920
```

```
atggtccacc tgctgccgca ttggaactgg aaggaagggg aaaaggtccg cgtcttagct    1980
tataccaatg caagtaaggt tgaacttgtt ctaaatggtg aatcgttagg ggagaagaac    2040
tatgacaaca acaaacctc ctggggagca ccatacaaag aaacaaagga tggaaaaacc     2100
tatttggagt gggccgtacc atttaaaccg ggcaaattag aagccgtcgc caaggatgaa    2160
aacggcaaag tgatcgcccg cgatcaggta gtgaccgctg gtgagccagc ctctgtcaga    2220
ttaacggctg atcgtaaggt ggtcaaggcg acggtacgg atctgtcgtt tattacagca     2280
gacattgttg atagtaaagg gattgttgtc ccggatgccg atcatctgat tacatttaac    2340
gtaacgggcc aaggggaatt ggccggggtt gataacggaa acgcgtccag tgtggagcgt    2400
tacaaggaca acaagcgcaa ggcttttcagc gggaaagcat ggcgattgt tcaatcaagt    2460
aagctttctg gaaaaattac ggtccatgcg tcagtggcag ggctttcgag cgattccacg    2520
agcgtattta cggtaacgcc agctgaccat gacaaaaaga ttgtagctgg gattgatgat    2580
gttaaccta ctgtcgatgt caatgaagca ccaaagcttc cttcagaaat caaggtttat    2640
tacagtgatg agagtgcagc tgcgaagaat gtgacttggg atgaggtgga tccaaagcag    2700
tacagcactg ttggtgaatt cacagtggaa ggcagtgtcg agggaacttc gctgaaggca    2760
aaggcatttg ttattgtcaa aggaattgtc gccgtcaagc cttattcaac ggcaacaaag    2820
gttggtgtac agccggtgct gcctgaaaaa gcaacccttc tttacagtga tggaacaacc    2880
aagggagcaa ctgtcacgtg ggatgagatc cctgaggaca agctggcaaa agagggccgg    2940
tttaccgtcg agggcagtgt ggagggaaca gacctcaagg ctaatgtcta tgtcagggtg    3000
acaaatgaag taaaatcagt gaatattatg cttcaggagc agggttcagc ttatccaaag    3060
ctcgaagcta cttttaccaa tccagctgac aatcttcagc atttgaacga tggcatcaag    3120
agctatacca ataaccccggt caaccgctgg acgaactgga caagaacacc gcgtgatgct    3180
ggtgactcga ttacagttaa ttttggcaag aagcatgtga ttaataatct agatttatt     3240
gtttttaccg acagcggcac ggtggttcca gaaaaggcag aggtccaata ttgggatgga    3300
acggcgtgga aggatgtcga aaatctaaca cagccatcgc catatgtggt agagaaaaat    3360
gaacttacat ttgatgcggt cgcgacagaa aagctgaaat tccatttgac accatctgtg    3420
aaagggaaat tcctagctct aacggaagca gaggtgtacg ccgatcagat tgtgatgggt    3480
gaaacagcaa aacttcaaag tattacggtg aatgggaaag cattagaagg cttttgatcac   3540
gctaaaaaga attatgaact tgtacttcca tatggaagcg agcttcctaa gattgaggcg    3600
gctgctgccg acaatgcaac tgtcaccatt ttaccggcat tctcctatcc gggaacagca    3660
aaactatttg tcacttcaga ggatgggaag gtaactactg agtacagtat tggtgtttct    3720
acagaagagc aaagctcgt ctccgca                                          3747
```

<210> SEQ ID NO 8
<211> LENGTH: 2541
<212> TYPE: DNA
<213> ORGANISM: Bacillus circulans

<400> SEQUENCE: 8

```
gtgaaaaaag cgattagctg cgttttttta atttcagcac tgattctatc aagctttcaa      60
gtccctgtac agggacaagc catgtcaaaa acgacatcgg cagcaggaaa cagtgtgagc     120
tatgatggag agagacgagt gaattttaac gagaattggc gatttcaacg agaaaccaat    180
ggaagtattg ccggagcaca gaatcctggc tttgacgatt cctcctggcg gaaattaaat    240
ctgccgcatg actggagtat tgaattagat tttaataaaa attctcttgc cacacatgaa    300
```

-continued

```
ggcggttatt tggacggcgg aatcggctgg taccgaaaaa cctttacaat cccggaatcg      360
atgaagggaa aacgaatttc gcttgatttt gatggcgttt acatgaacag caccacctat      420
ctaaacgggg aagtgctcgg gacctatccg tttggttata atgccttttc ctatgatatt      480
tccgacaaac tttataaaga tggcagggcg aatgtccttg ttgtcaaagt caataacacc      540
cagccgagca gccgctggta ttcggggagc gggatctacc ggaatgtcta tctcactgtg      600
accgatccca tccatgtggc tcgctacgga acatttgtga caacacccaa tttagagaaa      660
tcgataaaag aagacagggc tgatgtgaac atcaagacga aaatcagtaa cgatgctgct      720
gaggcgaaac aggtaaagat taaatcaacc atctacgatg gggctgggaa caccgtacag      780
acagtggaaa cggaggaaaa aacagctgcc gccggcacgg tgactccgtt cgaacaaaac      840
acagtcatca agcagccgaa gctttggagc attgacaagc cttatcgata taaccttgtt      900
acagaagtca tcgttggcgg gcaaacggtg gatacgtatg aaacaaaatt tggtgtcagg      960
tatttcaaat ttgatgaaaa cgaaggcttt tccttaaatg gagagtatat gaagctgcac     1020
ggcgtttcga tgcaccatga tttaggggcg cttggggcgg caacgaatgc acgcggcgtg     1080
gaaagacaaa tgcagattat gaaggatatg ggggtcaatg ccatcagggt tacccacaac     1140
ccggcatcac cggaactgct ggaggcagct aataaattag gctattcat catcgaggag     1200 gcatttgaca gctgggccca gtcaaagaaa ccctatgact atggccgttt tttcaatgca     1260
tgggctgagc acgacattaa ggaaatggtc gatcggggca aaacgaacc agctattatc     1320 atgtggtcga tcggaaatga aatatatgat acgaccaatg ccgctggtgt ggaaacagca     1380
cgaaatttag tgggttgggt aaaagaaatt gacaccacaa ggccgacaac gatcggcgag     1440
gataaaaccc gcggagacaa agtaaatgtt acacctatca acagctacat caaggagatt     1500
tttaatattg tcgatgtggt cggactgaac tacagcgaga caactatga tggctaccac     1560 aagcagaatc cgtcatggaa gctgtacggc tcggagacgt cctcggcaac ccgttcgcgt     1620
ggtgtctaca cgcatccgta ccagtataac caaagcacaa gtatgctga tttacagcaa     1680 tcctcttatg acaatgacta tgtcggctgg ggacgaactg cagaagatgc atggaaatat     1740
gaccgcgacc tgaagcatat tgcagggcaa tttatctgga ccggctttga ttatattggc     1800
gagccgacgc catattataa ttcctatcct gcaaaaagct cctatttggg tgctgtggat     1860
acggctggtt ttccaaagga tattttctac tattaccaaa gccaatggaa aaaggagcct     1920
atggtccacc tgctgccgca ttggaactgg aaggaagggg aaaaggtccg cgtcttagct     1980
tataccaatg caagtaaggt tgaacttgtt ctaaatggtg aatcgttagg ggagaagaac     2040
tatgacaaca aacaaacctc ctggggagca ccatacaaag aaacaaagga tggaaaaacc     2100
tatttggagt gggccgtacc atttaaaccg gcaaattag aagccgtcgc caaggatgaa     2160
aacggcaaag tgatcgcccg cgatcaggta gtgaccgctg gtgagccagc ctctgtcaga     2220
ttaacggctg atcgtaaggt ggtcaaggcg gacggtacgg atctgtcgtt tattacagca     2280
gacattgttg atagtaaagg gattgttgtc ccggatgccg atcatctgat tacatttaac     2340
gtaacgggcc aagggaatt ggccggggtt gataacggaa acgcgtccag tgtggagcgt     2400
tacaaggaca acaagcgcaa ggctttcagc gggaaagcat ggcgattgt tcaatcaagt     2460 aagctttctg gaaaaattac ggtccatgcg tcagtggcag ggctttcgag cgattccacg     2520
agcgtattta cggtaacgcc a                                                2541
```

MODIFIED β-GALACTOSIDASE

This Application is a Division of application Ser. No. 15/022,685, filed on Mar. 17, 2016, which is a National Stage Entry of PCT Application No. PCT/JP2014/075575, filed on Sep. 26, 2014, which claims priority from Application 2013-205097 filed on Sep. 30, 2013 in Japan. The entire contents of these applications are incorporated herein by reference in their entirety.

TECHNICAL FIELD

The present invention relates to a β-galactosidase. Specifically, the present invention relates to modifications of a β-galactosidase derived from *Bacillus circulans*, uses of modified enzymes thereof, and others. The present application claims priority to Japanese Patent Application No. 2013-205097, filed on Sep. 30, 2013, the entire content of which is incorporated herein by reference.

BACKGROUND ART

β-galactosidase (EC 3.2.1.23) is an enzyme which hydrolyzes a β-D-galactoside linkage to release D-galactose, and β-galactosidase isozymes are generally found in a wide range of microorganisms and plants. β-galactosidase is otherwise referred to as lactase. β-galactosidase is also capable of transferring a galactoside linkage, and there are known methods in which this capability is used to produce galacto-oligosaccharides (oligosaccharides having galactose residues).

Galacto-oligosaccharides, which are linear or branched polymers of galactose, are composed of galactose except that they terminate in a glucose unit. Galacto-oligosaccharides are contained in mother's milk, which is reported to be a mixture of a variety of galacto-oligosaccharides (Non Patent Literature 1).

CITATIONS LIST

Patent Literature

Patent Literature 1: WO 2010/140435

Non Patent Literatures

Non Patent Literature 1: Urashima et al., *KAGAKU TO SEIBUTSU* [Chemistry and Biology], 50, 7 (2012)
Non Patent Literature 2: Song et al., *Biosci. Biotechnol. Biochem.*, 77, 73-79 (2013)

SUMMARY OF INVENTION

Technical Problems

Various β-galactosidases are known to be produced by a koji mold *Aspergillus oryzae*, yeasts *Kluyveromyces lactis* and *Kluyveromyces marxinus*, a bacterium *Bacillus circulans*, and others. Among β-galactosidase enzymes produced by these microorganisms, the β-galactosidase derived from *Bacillus circulans*, which is a mixture of β-galactosidase isozymes, is an enzyme allowing the production of galacto-oligosaccharides from lactose, and is an important enzyme in the industrial production of galacto-oligosaccharides (for example, a preparation of β-galactosidase isozymes is marketed under a trade name of "BIOLACTA"). The galacto-oligosaccharides produced using this enzyme preparation are highly uniform in composition, and it has been difficult that the composition (profile) of the galacto-oligosaccharides to be produced is altered even though modifications of production conditions and others have been made. Thus, the present invention mainly aims at providing a modified β-galactosidase of which the enzymatic specificity has been modified as desired in order to further enhance the usefulness of the β-galactosidase derived from *Bacillus circulans* and make it possible to that the enzyme is applied to new applications, for example, production of oligosaccharides which cannot be produced or are produced with low efficiency by the wild-type enzyme.

Solutions to Problems

In previous studies, it was difficult to obtain the steric structure information of β-galactosidase isozymes derived from *Bacillus circulans*, so that it has not been easy to identify amino acids responsible for functions of these enzymes. For this reason, the inventors attempted to use computer simulation for prediction of their steric structures, and at the same time, to select amino acid residues useful in altering their properties, taking note of characteristic domain structures of the enzymes. Various variant enzymes were designed by introducing mutations at the positions of selected amino acid residues and examined for their properties, with the result that variants with apparently altered enzymatic specificities were found, for example, ones with decreased or increased hydrolytic activities for a β-1,6-bond. Accordingly, the inventors were able to identify amino acid residues that are useful and important in modifying the enzymatic specificity and successfully obtained a plurality of variants (modified enzymes) having altered enzymatic specificities. In addition, variants were designed taking note of a previous report (Non Patent Literature 2) and investigated in detail for their properties, with the result that other amino acids residues were also found which were useful in altering enzymatic specificity.

As is often experienced, on the other hand, combinations of two amino acid substitutions that are effective are highly likely to bring about additive or synergistic effects. Therefore, it can be said that the positions for mutation that have been successfully identified are effective, not only each alone, but also in combination thereof, in altering enzymatic properties.

On the basis of the above-described results and speculations, the following inventions are provided:

[1] A modified β-galactosidase consisting of an amino acid sequence in which one or more amino acids selected from the group consisting of proline at position 182 (P182), tyrosine at position 187 (Y187), serine at position 188 (S188), tryptophan at position 405 (W405), alanine at position 406 (A406), glutamine at position 407 (Q407), tyrosine at position 449 (Y449), threonine at position 483 (T483), serine at position 512 (S512), serine at position 531 (S531), threonine at position 533 (T533), serine at position 534 (S534), asparagine at position 550 (N550), glutamine at position 551 (Q551), tryptophan at position 593 (W593), tyrosine at position 598 (Y598), proline at position 602 (P602), proline at position 604 (P604), tyrosine at position 609 (Y609), lysine at position 612 (K612), and tyrosine at position 615 (Y615), or an amino acid(s) corresponding thereto, has/have been substituted by other amino acid in a β-galactosidase consisting of the amino acid sequence of any of SEQ ID NOs. 1 to 4 or an amino acid sequence having 90% or more identity to the amino acid sequence set forth in any of SEQ ID NOs. 1 to 4.

[2] The modified β-galactosidase according to [1], wherein the one or more amino acids to be substituted are selected from the group consisting of tyrosine at position 449 (Y449), serine at position 531 (S531), tryptophan at position 593 (W593), proline at position 602 (P602), proline at position 604 (P604), and lysine at position 612 (K612).

[3] The modified β-galactosidase according to [1], wherein the one or more amino acids to be substituted are selected from the group consisting of tyrosine at position 187 (Y187), serine at position 188 (S188), threonine at position 533 (T533), proline at position 602 (P602), and lysine at position 612 (K612).

[4] The modified β-galactosidase according to [1], wherein the one or more amino acids to be substituted are selected from the group consisting of proline at position 182 (P182), tyrosine at position 187 (Y187), serine at position 188 (S188), tryptophan at position 405 (W405), glutamine at position 407 (Q407), tyrosine at position 449 (Y449), threonine at position 483 (T483), serine at position 512 (S512), serine at position 531 (S531), asparagine at position 550 (N550), proline at position 602 (P602), and proline at position 604 (P604).

[5] The modified β-galactosidase according to [1], wherein the one or more amino acids to be substituted are selected from the group consisting of threonine at position 483 (T483), serine at position 512 (S512), glutamine at position 551 (Q551), tyrosine at position 598 (Y598), and tyrosine at position 615 (Y615).

[6] The modified β-galactosidase according to [1], wherein the one or more amino acids to be substituted are selected from the group consisting of tryptophan at position 405 (W405), threonine at position 483 (T483), serine at position 531 (S531), asparagine at position 550 (N550), and tyrosine at position 598 (Y598).

[7] The modified β-galactosidase according to [1], wherein the one or more amino acids to be substituted are selected from the group consisting of proline at position 182 (P182), tyrosine at position 187 (Y187), serine at position 188 (S188), tryptophan at position 405 (W405), alanine at position 406 (A406), glutamine at position 407 (Q407), tyrosine at position 449 (Y449), threonine at position 483 (T483), serine at position 512 (S512), serine at position 534 (S534), asparagine at position 550 (N550), glutamine at position 551 (Q551), proline at position 602 (P602), tyrosine at position 609 (Y609), lysine at position 612 (K612), and tyrosine at position 615 (Y615).

[8] The modified β-galactosidase according to [2], wherein the amino acid that has been substituted for tyrosine at position 449 (Y449) is aspartic acid, glutamic acid, asparagine, or tryptophan; the amino acid that has been substituted for serine at position 531 (S531) is alanine, aspartic acid, glutamic acid, phenylalanine, glycine, isoleucine, methionine, asparagine, or glutamine; the amino acid that has been substituted for tryptophan at position 593 (W593) is phenylalanine; the amino acid that has been substituted for proline at position 602 (P602) is glutamic acid or glycine; the amino acid that has been substituted for proline at position 604 (P604) is alanine, glycine, histidine, isoleucine, methionine, serine, threonine, valine, tryptophan, or tyrosine; and the amino acid that has been substituted for lysine at position 612 (K612) is methionine.

[9] The modified β-galactosidase according to [3], wherein the amino acid that has been substituted for tyrosine at position 187 (Y187) is aspartic acid, glutamic acid, or glycine; the amino acid that has been substituted for serine at position 188 (S188) is proline or threonine; the amino acid that has been substituted for threonine at position 533 (T533) is methionine or glutamine; the amino acid that has been substituted for proline at position 602 (P602) is cysteine, isoleucine, asparagine, serine, threonine, or valine; and the amino acid that has been substituted for lysine at position 612 (K612) is phenylalanine.

[10] The modified β-galactosidase according to [4], wherein the amino acid that has been substituted for proline at position 182 (P182) is leucine; the amino acid that has been substituted for tyrosine at position 187 (Y187) is aspartic acid or leucine; the amino acid that has been substituted for serine at position 188 (S188) is isoleucine; the amino acid that has been substituted for tryptophan at position 405 (W405) is alanine, aspartic acid, glutamic acid, glycine, histidine, leucine, asparagine, serine, or threonine; the amino acid that has been substituted for glutamine at position 407 (Q407) is glycine or arginine; the amino acid that has been substituted for tyrosine at position 449 (Y449) is glutamic acid, isoleucine, glutamine, arginine, or serine; the amino acid that has been substituted for threonine at position 483 (T483) is glutamine; the amino acid that has been substituted for serine at position 512 (S512) is phenylalanine, threonine, or valine; the amino acid that has been substituted for serine at position 531 (S531) is proline; the amino acid that has been substituted for asparagine at position 550 (N550) is leucine, arginine, or serine; the amino acid that has been substituted for proline at position 602 (P602) is leucine, asparagine, or glutamine; and the amino acid that has been substituted for proline at position 604 (P604) is isoleucine or methionine.

[11] The modified β-galactosidase according to [5], wherein the amino acid that has been substituted for threonine at position 483 (T483) is lysine, methionine, or arginine; the amino acid that has been substituted for serine at position 512 (S512) is glycine or lysine; the amino acid that has been substituted for glutamine at position 551 (Q551) is asparagine; the amino acid that has been substituted for tyrosine at position 598 (Y598) is asparagine; and the amino acid that has been substituted for tyrosine at position 615 (Y615) is threonine.

[12] The modified β-galactosidase according to [6], wherein the amino acid that has been substituted for tryptophan at position 405 (W405) is alanine, aspartic acid, serine, or threonine; the amino acid that has been substituted for threonine at position 483 (T483) is methionine; the amino acid that has been substituted for serine at position 531 (S531) is aspartic acid, phenylalanine, glycine, leucine, lysine, or methionine; the amino acid that has been substituted for asparagine at position 550 (N550) is phenylalanine; and the amino acid that has been substituted for tyrosine at position 598 (Y598) is phenylalanine or histidine.

[13] The modified β-galactosidase according to [7], wherein the amino acid that has been substituted for proline at position 182 (P182) is leucine or serine; the amino acid that has been substituted for tyrosine at position 187 (Y187) is aspartic acid, glutamic acid, or asparagine; the amino acid that has been substituted for serine at position 188 (S188) is glutamic acid, glycine, isoleucine, or asparagine; the amino acid that has been substituted for tryptophan at position 405 (W405) is histidine; the amino acid that has been substituted for alanine at position 406 (A406) is proline; the amino acid that has been substituted for glutamine at position 407 (Q407) is alanine, phenylalanine, glycine, lysine, or arginine; the amino acid that has been substituted for tyrosine at position 449 (Y449) is glutamic acid or arginine; the amino acid that has been substituted for threonine at position 483 (T483) is serine or glutamine; the amino acid that has been substituted for serine at position 512 (S512) is glycine, threonine, or valine; the amino acid that has been substituted for serine at position 534 (S534) is lysine or glutamine; the amino acid that has been substituted for asparagine at position 550 (N550) is alanine, glycine, lysine, leucine, methionine, arginine, or serine; the amino acid that has been substituted for glutamine at position 551 (Q551) is lysine or histidine; the amino acid that has been substituted for proline at position 602 (P602) is cysteine, aspartic acid, or asparagine; the amino acid that has been substituted for tyrosine at position 609 (Y609) is aspartic acid, glutamine, or threonine; the amino acid that has been substituted for lysine at position 612 (K612) is phenylalanine or isoleucine; and the amino acid that has been substituted for tyrosine at position 615 (Y615) is glutamic acid, isoleucine, or threonine.

[14] The modified β-galactosidase according to any one of [1] to [13], wherein the β-galactosidase consists of the amino acid sequence of SEQ ID NO. 1, and the modified β-galactosidase consists of an amino acid sequence in which in addition to the substitution, the tryptophan at position 1540 (W1540) is substituted with othe amino acid.

[15] A modified β-galactosidase consisting of an amino acid sequence in which one or more amino acids selected from the group consisting of tryptophan at position 85 (W85), phenylalanine at position 91 (F91), tyrosine at position 103 (Y103), tyrosine at position 134 (Y134), tyrosine at position 153 (Y153), proline at position 182 (P182), tryptophan at position 186 (W186), tyrosine at position 192 (Y192), tyrosine at position 295 (Y295), histidine at position 345 (H345), glycine at position 349 (G349), phenylalanine at position 402 (F402), glutamine at position 407 (Q407), glycine at position 479 (G479), glutamic acid at position 480 (E480), lysine at position 482 (K482), threonine at position 483 (T483), arginine at position 484 (R484), glycine at position 485 (G485), aspartic acid at position 486 (D486), lysine at position 487 (K487), valine at position 488 (V488), tyrosine at position 496 (Y496), serine at position 512 (S512), glutamic acid at position 513 (E513), asparagine at position 514 (N514), asparagine at position 515 (N515), tyrosine at position 516 (Y516), aspartic acid at position 517 (D517), tyrosine at position 519 (Y519), threonine at position 533 (T533), tyrosine at position 547 (Y547), tyrosine at position 549 (Y549), tyrosine at position 555 (Y555), arginine at position 572 (R572), threonine at position 573 (T573), tyrosine at position 598 (Y598), tyrosine at position 605 (Y605), tyrosine at position 606 (Y606), tyrosine at position 609 (Y609), phenylalanine at position 616 (F616), phenylalanine at position 624 (F624), tryptophan at position 648 (W648), and tryptophan at position 650 (W650), or an amino acid(s) corresponding thereto, has/have been substituted by other amino acid in a β-galactosidase consisting of the amino acid sequence of any of SEQ ID NOs. 1 to 4 or an amino acid sequence having 90% or more identity to the amino acid sequence set forth in any of SEQ ID NOs. 1 to 4.

[16] The modified β-galactosidase according to [15], wherein the amino acid that has been substituted for tryptophan at position 85 (W85) is glycine; the amino acid that has been substituted for phenylalanine at position 91 (F91) is alanine or isoleucine; the amino acid that has been substituted for tyrosine at position 103 (Y103) is glycine; the amino acid that has been substituted for tyrosine at position 134 (Y134) is glycine; the amino acid that has been substituted for tyrosine at position 153 (Y153) is glycine; the amino acid that has been substituted for proline at position 182 (P182) is tryptophan or tyrosine; the amino acid that has been substituted for tryptophan at position 186 (W186) is methionine; the amino acid that has been substituted for tyrosine at position 192 (Y192) is glycine; the amino acid that has been substituted for tyrosine at position 295 (Y295) is glycine; the amino acid that has been substituted for histidine at position 345 (H345) is glycine; the amino acid that has been substituted for glycine at position 349 (G349) is tryptophan; the amino acid that has been substituted for phenylalanine at position 402 (F402) is glycine; the amino acid that has been substituted for glutamine at position 407 (Q407) is isoleucine, leucine, methionine, valine, or tyrosine; the amino acid that has been substituted for glycine at position 479 (G479) is leucine, proline, or glutamine; the amino acid that has been substituted for glutamic acid at position 480 (E480) is asparagine; the amino acid that has been substituted for lysine at position 482 (K482) is methionine or valine; the amino acid that has been substituted for threonine at position 483 (T483) is glycine or serine; the amino acid that has been substituted for arginine at position 484 (R484) is phenylalanine, isoleucine, methionine, asparagine, or glutamine; the amino acid that has been substituted for glycine at position 485 (G485) is aspartic acid, asparagine, glutamine, or threonine; the amino acid that has been substituted for aspartic acid at position 486 (D486) is alanine, glutamic acid, phenylalanine, isoleucine, lysine, leucine, methionine, proline, glutamine, arginine, threonine, tryptophan, or tyrosine; the amino acid that has been substituted for lysine at position 487 (K487) is cysteine, glutamic acid, phenylalanine, histidine, isoleucine, leucine, asparagine, glutamine, arginine, threonine, valine, tryptophan, or tyrosine; the amino acid that has been substituted for valine at position 488 (V488) is glycine, isoleucine, leucine, arginine, serine, threonine, tryptophan, or tyrosine; the amino acid that has been substituted for tyrosine at position 496 (Y496) is glycine; the amino acid that has been substituted for serine at position 512 (S512) is cysteine, aspartic acid, glutamic acid, asparagine, proline, glutamine, or tryptophan; the amino acid that has been substituted for glutamic acid at position 513 (E513) is alanine, cysteine, aspartic acid, phenylalanine, glycine, histidine, lysine, leucine, methionine, asparagine, proline, glutamine, arginine, serine, threonine, or valine; the amino acid that has been substituted for asparagine at position 514 (N514) is glutamic acid, leucine, or lysine; the amino acid that has been substituted for asparagine at position 515 (N515) is alanine, aspartic acid, glutamic acid, glycine, isoleucine, leucine, proline, or valine; the amino acid that has been substituted for tyrosine at position 516 (Y516) is tryptophan; the amino acid that has been substituted for aspartic acid at position 517 (D517) is lysine or tryptophan; the amino acid that has been substituted for tyrosine at position 519 (Y519) is glycine; the amino acid that has been substituted for threonine at position 533 (T533) is glutamic acid; the amino acid that has been substituted for tyrosine at position 547 (Y547) is glycine; the amino acid that has been substituted for tyrosine at position 549 (Y549) is glycine; the amino acid that has been substituted for tyrosine at position 555 (Y555) is glycine; the amino acid that has been substituted for arginine at position 572 (R572) is cysteine, leucine, methionine, threonine, tryptophan, or tyrosine; the amino acid that has been substituted for threonine at position 573 (T573) is glutamic acid; the amino acid that has been substituted for tyrosine at position 598 (Y598) is histidine or asparagine; the amino acid that has been substituted for tyrosine at position 605 (Y605) is cysteine, aspartic acid, histidine, isoleucine, lysine, proline, arginine, or threonine; the amino acid that has been substituted for tyrosine at position 606 (Y606) is alanine, cysteine, aspartic acid, glutamic acid, phenylalanine, glycine, histidine, isoleucine, lysine, leucine, methionine, or serine; the amino acid that has been substituted for tyrosine at position 609 (Y609) is glutamic acid, asparagine, or serine; the amino acid that has been substituted for phenylalanine at position 616 (F616) is glycine; the amino acid that has been substituted for phenylalanine at position 624 (F624) is glycine; the amino acid that has been substituted for tryptophan at position 648 (W648) is glycine; and the amino acid that has been substituted for tryptophan at position 650 (W650) is glycine.

[17] A modified β-galactosidase consisting of an amino acid sequence in which one or more amino acids selected from the group consisting of tryptophan at position 76 (W76), glutamic acid at position 480 (E480), threonine at position 483 (T483), glycine at position 485 (G485), arginine at position 484 (R484), lysine at position 487 (K487), valine at position 488 (V488), serine at position 512 (S512), asparagine at position 514 (N514), asparagine at position 515 (N515), glycine at position 569 (G569), and phenylalanine at position 596 (F596), or an amino acid(s) corresponding thereto, has/have been substituted by other amino acid in a β-galactosidase consisting of the amino acid sequence of any of SEQ ID NOs. 1 to 4 or an amino acid sequence having 90% or more identity to the amino acid sequence set forth in any of SEQ ID NOs. 1 to 4.

[18] The modified β-galactosidase according to [17], wherein the amino acid that has been substituted for tryptophan at position 76 (W76) is glycine; the amino acid that has been substituted for glutamic acid at position 480 (E480) is glutamine; the amino acid that has been substituted for threonine at position 483 (T483) is tryptophan; the amino acid that has been substituted for glycine at position 485 (G485) is proline or threonine; the amino acid that has been substituted for arginine at position 484 (R484) is alanine, cysteine, aspartic acid, glycine, proline, serine, tyrosine, or lysine; the amino acid that has been substituted for lysine at position 487 (K487) is glycine or proline; the amino acid that has been substituted for valine at position 488 (V488) is proline; the amino acid that has been substituted for serine at position 512 (S512) is leucine or methionine; the amino acid that has been substituted for asparagine at position 514 (N514) is aspartic acid; the amino acid that has been substituted for asparagine at position 515 (N515) is phenylalanine, arginine, tryptophan, tyrosine, or lysine; the amino acid that has been substituted for glycine at position 569 (G569) is lysine, proline, or valine; and the amino acid that has been substituted for phenylalanine at position 596 (F596) is glycine.

[19] A modified β-galactosidase, wherein the modified β-galactosidase has undergone any of the following modifications in a β-galactosidase consisting of the amino acid sequence of any of SEQ ID NOs. 1 to 4 or an amino acid sequence having 90% or more identity to the amino acid sequence set forth in any of SEQ ID NOs. 1 to 4:

a double substitution in which the serine at position 188 or an amino acid corresponding thereto is substituted with isoleucine and the asparagine at position 550 or an amino acid corresponding thereto is substituted with phenylalanine (S188I_N550F);

a double substitution in which the glutamine at position 407 or an amino acid corresponding thereto is substituted with arginine and the asparagine at position 550 or an amino acid corresponding thereto is substituted with phenylalanine (Q407R_N550F);

a double substitution in which the tyrosine at position 449 or an amino acid corresponding thereto is substituted with glutamine and the tyrosine at position 598 or an amino acid corresponding thereto is substituted with histidine (Y449Q_Y598H);

a double substitution in which the asparagine at position 550 or an amino acid corresponding thereto is substituted with phenylalanine and the proline at position 602 or an amino acid corresponding thereto is substituted with glutamine (N550F_P602Q);

a double substitution in which the glutamine at position 407 or an amino acid corresponding thereto is substituted with arginine and the tyrosine at position 449 or an amino acid corresponding thereto is substituted with glutamic acid (Q407R_Y449E);

a double substitution in which the asparagine at position 550 or an amino acid corresponding thereto is substituted with phenylalanine and the tyrosine at position 598 or an amino acid corresponding thereto is substituted with asparagine (N550F_Y598N);

a double substitution in which the proline at position 182 or an amino acid corresponding thereto is substituted with leucine and the tyrosine at position 449 or an amino acid corresponding thereto is substituted with glutamic acid (P182L_Y449E);

a double substitution in which the proline at position 182 or an amino acid corresponding thereto is substituted with leucine and the tyrosine at position 449 or an amino acid corresponding thereto is substituted with glutamine (P182L_Y449Q);

a double substitution in which the tyrosine at position 187 or an amino acid corresponding thereto is substituted with leucine and the glutamine at position 407 or an amino acid corresponding thereto is substituted with arginine (Y187L_Q407R);

a double substitution in which the tyrosine at position 187 or an amino acid corresponding thereto is substituted with leucine and the tyrosine at position 449 or an amino acid corresponding thereto is substituted with glutamic acid (Y187L_Y449E);

a double substitution in which the tyrosine at position 187 or an amino acid corresponding thereto is substituted with leucine and the tyrosine at position 449 or an amino acid corresponding thereto is substituted with glutamine (Y187L_Y449Q);

a double substitution in which the tyrosine at position 187 or an amino acid corresponding thereto is substituted with leucine and the serine at position 512 or an amino acid corresponding thereto is substituted with cysteine (Y187L_S512C);

a double substitution in which the tyrosine at position 187 or an amino acid corresponding thereto is substituted with leucine and the serine at position 512 or an amino acid corresponding thereto is substituted with asparagine (Y187L_S512N);

a double substitution in which the tyrosine at position 187 or an amino acid corresponding thereto is substituted with leucine and the serine at position 512 or an amino acid corresponding thereto is substituted with threonine (Y187L_S512T);

a double substitution in which the serine at position 188 or an amino acid corresponding thereto is substituted with isoleucine and the glutamine at position 407 or an amino acid corresponding thereto is substituted with arginine (S188I_Q407R);

a double substitution in which the serine at position 188 or an amino acid corresponding thereto is substituted with isoleucine and the tyrosine at position 449 or an amino acid corresponding thereto is substituted with glutamine (S188I_Y449Q);

a double substitution in which the serine at position 188 or an amino acid corresponding thereto is substituted with isoleucine and the threonine at position 483 or an amino acid corresponding thereto is substituted with glutamic acid (S188I_T483E);

a double substitution in which the glutamine at position 407 or an amino acid corresponding thereto is substituted with leucine and the serine at position 512 or an amino acid corresponding thereto is substituted with valine (Q407L_S512V);

a double substitution in which the glutamine at position 407 or an amino acid corresponding thereto is substituted with arginine and the threonine at position 483 or an amino acid corresponding thereto is substituted with glycine (Q407R_T483G);

a double substitution in which the glutamine at position 407 or an amino acid corresponding thereto is substituted with arginine and the tyrosine at position 449 or an amino acid corresponding thereto is substituted with glutamine (Q407R_Y449Q);

a double substitution in which the glutamine at position 407 or an amino acid corresponding thereto is substituted with arginine and the asparagine at position 550 or an amino acid corresponding thereto is substituted with serine (Q407R_N550S);

a double substitution in which the tyrosine at position 449 or an amino acid corresponding thereto is substituted with glutamine and the asparagine at position 550 or an amino acid corresponding thereto is substituted with serine (Y449Q_N550S);

a double substitution in which the lysine at position 487 or an amino acid corresponding thereto is substituted with tryptophan and the serine at position 512 or an amino acid corresponding thereto is substituted with threonine (K487W_S512T);

a double substitution in which the lysine at position 487 or an amino acid corresponding thereto is substituted with tryptophan and the aspartic acid at position 517 or an amino acid corresponding thereto is substituted with lysine (K487W_D517K);

a double substitution in which the lysine at position 487 or an amino acid corresponding thereto is substituted with tryptophan and the asparagine at position 515 or an amino acid corresponding thereto is substituted with glycine (K487W_N515G);

a double substitution in which the lysine at position 487 or an amino acid corresponding thereto is substituted with tryptophan and the aspartic acid at position 517 or an amino acid corresponding thereto is substituted with tryptophan (K487W_D517W);

a double substitution in which the lysine at position 487 or an amino acid corresponding thereto is substituted with proline and the asparagine at position 515 or an amino acid corresponding thereto is substituted with arginine (K487P_N515R);

a double substitution in which the phenylalanine at position 91 or an amino acid corresponding thereto is substituted with serine and the glutamine at position 407 or an amino acid corresponding thereto is substituted with methionine (F91S_Q407M);

a double substitution in which the threonine at position 180 or an amino acid corresponding thereto is substituted with valine and the tyrosine at position 187 or an amino acid corresponding thereto is substituted with leucine (T180V_Y187L);

a double substitution in which the threonine at position 180 or an amino acid corresponding thereto is substituted with valine and the serine at position 188 or an amino acid corresponding thereto is substituted with isoleucine (T180V_S188I);

a double substitution in which the threonine at position 180 or an amino acid corresponding thereto is substituted with valine and the glutamine at position 407 or an amino acid corresponding thereto is substituted with arginine (T180V_Q407R);

a double substitution in which the threonine at position 180 or an amino acid corresponding thereto is substituted with valine and the tyrosine at position 449 or an amino acid corresponding thereto is substituted with glutamic acid (T180V_Y449E);

a double substitution in which the threonine at position 180 or an amino acid corresponding thereto is substituted with valine and the threonine at position 483 or an amino acid corresponding thereto is substituted with glycine (T180V_T483G);

a double substitution in which the threonine at position 180 or an amino acid corresponding thereto is substituted with valine and the serine at position 512 or an amino acid corresponding thereto is substituted with valine (T180V_S512V);

a double substitution in which the threonine at position 180 or an amino acid corresponding thereto is substituted with valine and the asparagine at position 550 or an amino acid corresponding thereto is substituted with phenylalanine (T180V_N550F);

a double substitution in which the threonine at position 180 or an amino acid corresponding thereto is substituted with valine and the tyrosine at position 615 or an amino acid corresponding thereto is substituted with proline (T180V_Y615P);

a double substitution in which the proline at position 182 or an amino acid corresponding thereto is substituted with leucine and the arginine at position 376 or an amino acid corresponding thereto is substituted with proline (P182L_R376P);

a double substitution in which the proline at position 182 or an amino acid corresponding thereto is substituted with tryptophan and the tyrosine at position 449 or an amino acid corresponding thereto is substituted with glutamine (P182W_Y449Q);

a double substitution in which the tyrosine at position 187 or an amino acid corresponding thereto is substituted with leucine and the lysine at position 487 or an amino acid corresponding thereto is substituted with alanine (Y187L_K487A);

a double substitution in which the tyrosine at position 187 or an amino acid corresponding thereto is substituted with leucine and the serine at position 512 or an amino acid corresponding thereto is substituted with alanine (Y187L_S512A);

a double substitution in which the tyrosine at position 187 or an amino acid corresponding thereto is substituted with leucine and the threonine at position 533 or an amino acid corresponding thereto is substituted with asparagine (Y187L_T533N);

a double substitution in which the arginine at position 376 or an amino acid corresponding thereto is substituted with proline and the glutamine at position 407 or an amino acid corresponding thereto is substituted with leucine (R376P_Q407L);

a double substitution in which the arginine at position 376 or an amino acid corresponding thereto is substituted with proline and the tyrosine at position 449 or an amino acid corresponding thereto is substituted with glutamine (R376P_Y449Q);

a double substitution in which the arginine at position 376 or an amino acid corresponding thereto is substituted with proline and the serine at position 512 or an amino acid corresponding thereto is substituted with valine (R376P_S512V);

a double substitution in which the arginine at position 376 or an amino acid corresponding thereto is substituted with proline and the asparagine at position 550 or an amino acid corresponding thereto is substituted with tryptophan (R376P_N550W);

a double substitution in which the arginine at position 376 or an amino acid corresponding thereto is substituted with proline and the asparagine at position 550 or an amino acid corresponding thereto is substituted with tyrosine (R376P_N550Y);

a double substitution in which the glutamine at position 407 or an amino acid corresponding thereto is substituted with leucine and the threonine at position 533 or an amino acid corresponding thereto is substituted with glutamic acid (Q407L_T533E);

a double substitution in which the glutamine at position 407 or an amino acid corresponding thereto is substituted with leucine and the tryptophan at position 570 or an amino acid corresponding thereto is substituted with tyrosine (Q407L_W570Y);

a double substitution in which the glutamine at position 407 or an amino acid corresponding thereto is substituted with leucine and the tyrosine at position 615 or an amino acid corresponding thereto is substituted with leucine (Q407L_Y615L);

a double substitution in which the glutamine at position 407 or an amino acid corresponding thereto is substituted with arginine and the tyrosine at position 615 or an amino acid corresponding thereto is substituted with leucine (Q407R_Y615L);

a double substitution in which the glutamine at position 407 or an amino acid corresponding thereto is substituted with arginine and the tyrosine at position 615 or an amino acid corresponding thereto is substituted with proline (Q407R_Y615P);

a double substitution in which the tyrosine at position 449 or an amino acid corresponding thereto is substituted with aspartic acid and the tyrosine at position 598 or an amino acid corresponding thereto is substituted with phenylalanine (Y449D_Y598F);

a double substitution in which the tyrosine at position 449 or an amino acid corresponding thereto is substituted with glutamine and the threonine at position 533 or an amino acid corresponding thereto is substituted with glutamic acid (Y449Q_T533E);

a double substitution in which the tyrosine at position 449 or an amino acid corresponding thereto is substituted with glutamine and the tyrosine at position 615 or an amino acid corresponding thereto is substituted with glycine (Y449Q_Y615G);

a double substitution in which the tyrosine at position 449 or an amino acid corresponding thereto is substituted with glutamine and the tyrosine at position 615 or an amino acid corresponding thereto is substituted with proline (Y449Q_Y615P);

a double substitution in which the threonine at position 483 or an amino acid corresponding thereto is substituted with glycine and the serine at position 512 or an amino acid corresponding thereto is substituted with valine (T483G_S512V);

a double substitution in which the threonine at position 483 or an amino acid corresponding thereto is substituted with glycine and the asparagine at position 550 or an amino acid corresponding thereto is substituted with serine (T483G_N550S);

a double substitution in which the threonine at position 483 or an amino acid corresponding thereto is substituted with glycine and the tyrosine at position 615 or an amino acid corresponding thereto is substituted with leucine (T483G_Y615L);

a double substitution in which the threonine at position 483 or an amino acid corresponding thereto is substituted with glutamine and the proline at position 602 or an amino acid corresponding thereto is substituted with glutamine (T483Q_P602Q);

a double substitution in which the arginine at position 484 or an amino acid corresponding thereto is substituted with histidine and the lysine at position 487 or an amino acid corresponding thereto is substituted with histidine (R484H_K487H);

a double substitution in which the arginine at position 484 or an amino acid corresponding thereto is substituted with tryptophan and the lysine at position 487 or an amino acid corresponding thereto is substituted with aspartic acid (R484W_K487D);

a double substitution in which the arginine at position 484 or an amino acid corresponding thereto is substituted with tryptophan and the threonine at position 575 or an amino acid corresponding thereto is substituted with tryptophan (R484W_T575W);

a double substitution in which the glycine at position 485 or an amino acid corresponding thereto is substituted with lysine and the valine at position 488 or an amino acid corresponding thereto is substituted with tryptophan (G485K_V488W);

a double substitution in which the glycine at position 485 or an amino acid corresponding thereto is substituted with lysine and the tyrosine at position 516 or an amino acid corresponding thereto is substituted with tryptophan (G485K_Y516W);

a double substitution in which the glycine at position 485 or an amino acid corresponding thereto is substituted with lysine and the aspartic acid at position 517 or an amino acid corresponding thereto is substituted with lysine (G485K_D517K);

a double substitution in which the glycine at position 485 or an amino acid corresponding thereto is substituted with lysine and the aspartic acid at position 517 or an amino acid corresponding thereto is substituted with tryptophan (G485K_D517W);

a double substitution in which the glycine at position 485 or an amino acid corresponding thereto is substituted with lysine and the glycine at position 569 or an amino acid corresponding thereto is substituted with tryptophan (G485K_G569W);

a double substitution in which the glycine at position 485 or an amino acid corresponding thereto is substituted with lysine and the glycine at position 571 or an amino acid corresponding thereto is substituted with lysine (G485K_G571K);

a double substitution in which the glycine at position 485 or an amino acid corresponding thereto is substituted with lysine and the arginine at position 572 or an amino acid corresponding thereto is substituted with tryptophan (G485K_R572W);

a double substitution in which the glycine at position 485 or an amino acid corresponding thereto is substituted with lysine and the threonine at position 573 or an amino acid corresponding thereto is substituted with tryptophan (G485K_T573W);

a double substitution in which the glycine at position 485 or an amino acid corresponding thereto is substituted with tryptophan and the tyrosine at position 516 or an amino acid corresponding thereto is substituted with tryptophan (G485W_Y516W);

a double substitution in which the glycine at position 485 or an amino acid corresponding thereto is substituted with tryptophan and the aspartic acid at position 517 or an amino acid corresponding thereto is substituted with tryptophan (G485W_D517W);

a double substitution in which the glycine at position 485 or an amino acid corresponding thereto is substituted with tryptophan and the threonine at position 573 or an amino acid corresponding thereto is substituted with lysine (G485W_T573K);

a double substitution in which the glycine at position 485 or an amino acid corresponding thereto is substituted with tryptophan and the threonine at position 573 or an amino acid corresponding thereto is substituted with tryptophan (G485W_T573W);

a double substitution in which the lysine at position 487 or an amino acid corresponding thereto is substituted with alanine and the serine at position 512 or an amino acid corresponding thereto is substituted with valine (K487A_S512V);

a double substitution in which the lysine at position 487 or an amino acid corresponding thereto is substituted with glycine and the asparagine at position 515 or an amino acid corresponding thereto is substituted with glutamine (K487G_N515Q);

a double substitution in which the lysine at position 487 or an amino acid corresponding thereto is substituted with tryptophan and the threonine at position 573 or an amino acid corresponding thereto is substituted with lysine (K487W_T573K);

a double substitution in which the lysine at position 487 or an amino acid corresponding thereto is substituted with tryptophan and the tryptophan at position 593 or an amino acid corresponding thereto is substituted with phenylalanine (K487W_W593F);

a double substitution in which the valine at position 488 or an amino acid corresponding thereto is substituted with lysine and the asparagine at position 514 or an amino acid corresponding thereto is substituted with lysine (V488K_N514K);

a double substitution in which the valine at position 488 or an amino acid corresponding thereto is substituted with lysine and the aspartic acid at position 517 or an amino acid corresponding thereto is substituted with lysine (V488K_D517K);

a double substitution in which the valine at position 488 or an amino acid corresponding thereto is substituted with lysine and the glycine at position 569 or an amino acid corresponding thereto is substituted with lysine (V488K_G569K);

a double substitution in which the valine at position 488 or an amino acid corresponding thereto is substituted with lysine and the glycine at position 569 or an amino acid corresponding thereto is substituted with tryptophan (V488K_G569W);

a double substitution in which the valine at position 488 or an amino acid corresponding thereto is substituted with lysine and the arginine at position 572 or an amino acid corresponding thereto is substituted with lysine (V488K_R572K);

a double substitution in which the valine at position 488 or an amino acid corresponding thereto is substituted with lysine and the threonine at position 573 or an amino acid corresponding thereto is substituted with lysine (V488K_T573K);

a double substitution in which the valine at position 488 or an amino acid corresponding thereto is substituted with lysine and the threonine at position 573 or an amino acid corresponding thereto is substituted with tryptophan (V488K_T573W);

a double substitution in which the valine at position 488 or an amino acid corresponding thereto is substituted with lysine and the tyrosine at position 516 or an amino acid corresponding thereto is substituted with lysine (V488K_Y516K);

a double substitution in which the valine at position 488 or an amino acid corresponding thereto is substituted with lysine and the tyrosine at position 516 or an amino acid corresponding thereto is substituted with tryptophan (V488K_Y516W);

a double substitution in which the valine at position 488 or an amino acid corresponding thereto is substituted with tryptophan and the asparagine at position 514 or an amino acid corresponding thereto is substituted with tryptophan (V488W_N514W);

a double substitution in which the valine at position 488 or an amino acid corresponding thereto is substituted with tryptophan and the threonine at position 573 or an amino acid corresponding thereto is substituted with tryptophan (V488W_T573W);

a double substitution in which the glutamic acid at position 500 or an amino acid corresponding thereto is substituted with alanine and the isoleucine at position 501 or an amino acid corresponding thereto is substituted with alanine (E500A_I501A);

a double substitution in which the serine at position 512 or an amino acid corresponding thereto is substituted with valine and the asparagine at position 550 or an amino acid corresponding thereto is substituted with serine (S512V_N550S);

a double substitution in which the threonine at position 533 or an amino acid corresponding thereto is substituted with glutamic acid and the asparagine at position 550 or an amino acid corresponding thereto is substituted with serine (T533E_N550S);

a double substitution in which the threonine at position 533 or an amino acid corresponding thereto is substituted with glutamic acid and the tyrosine at position 615 or an amino acid corresponding thereto is substituted with glycine (T533E_Y615G);

a double substitution in which the tryptophan at position 570 or an amino acid corresponding thereto is substituted with tyrosine and the tyrosine at position 615 or an amino acid corresponding thereto is substituted with leucine (W570Y_Y615L);

a double substitution in which the phenylalanine at position 91 or an amino acid corresponding thereto is substituted with valine and the glutamic acid at position 513 or an amino acid corresponding thereto is substituted with glycine (F91V_E513G);

a double substitution in which the threonine at position 180 or an amino acid corresponding thereto is substituted with valine and the threonine at position 483 or an amino acid corresponding thereto is substituted with lysine (T180V_T483K);

a double substitution in which the threonine at position 180 or an amino acid corresponding thereto is substituted with valine and the tyrosine at position 598 or an amino acid corresponding thereto is substituted with asparagine (T180V_Y598N);

a double substitution in which the threonine at position 180 or an amino acid corresponding thereto is substituted with valine and the tyrosine at position 615 or an amino acid corresponding thereto is substituted with glycine (T180V_Y615G);

a double substitution in which the proline at position 182 or an amino acid corresponding thereto is substituted with leucine and the tyrosine at position 615 or an amino acid corresponding thereto is substituted with leucine (P182L_Y615L);

a double substitution in which the arginine at position 376 or an amino acid corresponding thereto is substituted with proline and the tyrosine at position 598 or an amino acid corresponding thereto is substituted with asparagine (R376P_Y598N);

a double substitution in which the glutamine at position 407 or an amino acid corresponding thereto is substituted with leucine and the threonine at position 483 or an amino acid corresponding thereto is substituted with lysine (Q407L_T483K);

a double substitution in which the glutamine at position 407 or an amino acid corresponding thereto is substituted with leucine and the lysine at position 487 or an amino acid corresponding thereto is substituted with proline (Q407L_K487P);

a double substitution in which the glutamine at position 407 or an amino acid corresponding thereto is substituted with leucine and the tyrosine at position 615 or an amino acid corresponding thereto is substituted with glycine (Q407L_Y615G);

a double substitution in which the tyrosine at position 449 or an amino acid corresponding thereto is substituted with glutamic acid and the lysine at position 487 or an amino acid corresponding thereto is substituted with alanine (Y449E_K487A);

a double substitution in which the tyrosine at position 449 or an amino acid corresponding thereto is substituted with glutamic acid and the lysine at position 487 or an amino acid corresponding thereto is substituted with proline (Y449E_K487P);

a double substitution in which the threonine at position 483 or an amino acid corresponding thereto is substituted with glycine and the lysine at position 487 or an amino acid corresponding thereto is substituted with alanine (T483G_K487A);

a double substitution in which the threonine at position 483 or an amino acid corresponding thereto is substituted with glycine and the threonine at position 533 or an amino acid corresponding thereto is substituted with glutamic acid (T483G_T533E);

a double substitution in which the threonine at position 483 or an amino acid corresponding thereto is substituted with glycine and the tyrosine at position 615 or an amino acid corresponding thereto is substituted with glycine (T483G_Y615G);

a double substitution in which the threonine at position 483 or an amino acid corresponding thereto is substituted with methionine and the lysine at position 487 or an amino acid corresponding thereto is substituted with alanine (T483M_K487A);

a double substitution in which the threonine at position 483 or an amino acid corresponding thereto is substituted with methionine and the lysine at position 487 or an amino acid corresponding thereto is substituted with glycine (T483M_K487G);

a double substitution in which the threonine at position 483 or an amino acid corresponding thereto is substituted with methionine and the lysine at position 487 or an amino acid corresponding thereto is substituted with proline (T483M_K487P);

a double substitution in which the arginine at position 484 or an amino acid corresponding thereto is substituted with histidine and the lysine at position 487 or an amino acid corresponding thereto is substituted with aspartic acid (R484H_K487D);

a double substitution in which the arginine at position 484 or an amino acid corresponding thereto is substituted with lysine and the glutamic acid at position 513 or an amino acid corresponding thereto is substituted with tryptophan (R484K_E513W);

a double substitution in which the arginine at position 484 or an amino acid corresponding thereto is substituted with lysine and the asparagine at position 514 or an amino acid corresponding thereto is substituted with lysine (R484K_N514K);

a double substitution in which the arginine at position 484 or an amino acid corresponding thereto is substituted with lysine and the asparagine at position 514 or an amino acid corresponding thereto is substituted with tryptophan (R484K_N514W);

a double substitution in which the arginine at position 484 or an amino acid corresponding thereto is substituted with lysine and the asparagine at position 515 or an amino acid corresponding thereto is substituted with lysine (R484K_N515K);

a double substitution in which the arginine at position 484 or an amino acid corresponding thereto is substituted with lysine and the asparagine at position 515 or an amino acid corresponding thereto is substituted with tryptophan (R484K_N515W);

a double substitution in which the arginine at position 484 or an amino acid corresponding thereto is substituted with lysine and the aspartic acid at position 517 or an amino acid corresponding thereto is substituted with tryptophan (R484K_D517W);

a double substitution in which the arginine at position 484 or an amino acid corresponding thereto is substituted with lysine and the glycine at position 569 or an amino acid corresponding thereto is substituted with lysine (R484K_G569K);

a double substitution in which the arginine at position 484 or an amino acid corresponding thereto is substituted with lysine and the glycine at position 571 or an amino acid corresponding thereto is substituted with lysine (R484K_G571K);

a double substitution in which the arginine at position 484 or an amino acid corresponding thereto is substituted with lysine and the arginine at position 572 or an amino acid corresponding thereto is substituted with lysine (R484K_R572K);

a double substitution in which the arginine at position 484 or an amino acid corresponding thereto is substituted with lysine and the arginine at position 572 or an amino acid corresponding thereto is substituted with tryptophan (R484K_R572W);

a double substitution in which the arginine at position 484 or an amino acid corresponding thereto is substituted with lysine and the threonine at position 573 or an amino acid corresponding thereto is substituted with lysine (R484K_T573K);

a double substitution in which the arginine at position 484 or an amino acid corresponding thereto is substituted with lysine and the threonine at position 573 or an amino acid corresponding thereto is substituted with tryptophan (R484K_T573W);

a double substitution in which the arginine at position 484 or an amino acid corresponding thereto is substituted with lysine and the tyrosine at position 516 or an amino acid corresponding thereto is substituted with lysine (R484K_Y516K);

a double substitution in which the arginine at position 484 or an amino acid corresponding thereto is substituted with tryptophan and the asparagine at position 515 or an amino acid corresponding thereto is substituted with lysine (R484W_N515K);

a double substitution in which the glycine at position 485 or an amino acid corresponding thereto is substituted with aspartic acid and the lysine at position 487 or an amino acid corresponding thereto is substituted with histidine (G485D_K487H);

a double substitution in which the glycine at position 485 or an amino acid corresponding thereto is substituted with lysine and the lysine at position 487 or an amino acid corresponding thereto is substituted with histidine (G485K_K487H);

a double substitution in which the glycine at position 485 or an amino acid corresponding thereto is substituted with lysine and the glycine at position 569 or an amino acid corresponding thereto is substituted with lysine (G485K_G569K);

a double substitution in which the glycine at position 485 or an amino acid corresponding thereto is substituted with lysine and the asparagine at position 514 or an amino acid corresponding thereto is substituted with lysine (G485K_N514K);

a double substitution in which the glycine at position 485 or an amino acid corresponding thereto is substituted with lysine and the asparagine at position 515 or an amino acid corresponding thereto is substituted with lysine (G485K_N515K);

a double substitution in which the glycine at position 485 or an amino acid corresponding thereto is substituted with lysine and the asparagine at position 515 or an amino acid corresponding thereto is substituted with tryptophan (G485K_N515W);

a double substitution in which the glycine at position 485 or an amino acid corresponding thereto is substituted with arginine and the lysine at position 487 or an amino acid corresponding thereto is substituted with aspartic acid (G485R_K487D);

a double substitution in which the glycine at position 485 or an amino acid corresponding thereto is substituted with tryptophan and the glutamic acid at position 513 or an amino acid corresponding thereto is substituted with tryptophan (G485W_E513W);

a double substitution in which the glycine at position 485 or an amino acid corresponding thereto is substituted with tryptophan and the asparagine at position 515 or an amino acid corresponding thereto is substituted with lysine (G485W_N515K);

a double substitution in which the glycine at position 485 or an amino acid corresponding thereto is substituted with tryptophan and the asparagine at position 515 or an amino acid corresponding thereto is substituted with tryptophan (G485W_N515W);

a double substitution in which the lysine at position 487 or an amino acid corresponding thereto is substituted with alanine and the serine at position 531 or an amino acid corresponding thereto is substituted with alanine (K487A_S531A);

a double substitution in which the lysine at position 487 or an amino acid corresponding thereto is substituted with alanine and the tryptophan at position 593 or an amino acid corresponding thereto is substituted with phenylalanine (K487A_W593F);

a double substitution in which the lysine at position 487 or an amino acid corresponding thereto is substituted with alanine and the tyrosine at position 615 or an amino acid corresponding thereto is substituted with leucine (K487A_Y615L);

a double substitution in which the lysine at position 487 or an amino acid corresponding thereto is substituted with tryptophan and the asparagine at position 514 or an amino acid corresponding thereto is substituted with lysine (K487W_N514K);

a double substitution in which the lysine at position 487 or an amino acid corresponding thereto is substituted with tryptophan and the asparagine at position 514 or an amino acid corresponding thereto is substituted with tryptophan (K487W_N514W);

a double substitution in which the lysine at position 487 or an amino acid corresponding thereto is substituted with tryptophan and the tyrosine at position 516 or an amino acid corresponding thereto is substituted with tryptophan (K487W_Y516W);

a double substitution in which the lysine at position 487 or an amino acid corresponding thereto is substituted with tryptophan and the glycine at position 569 or an amino acid corresponding thereto is substituted with lysine (K487W_G569K);

a double substitution in which the lysine at position 487 or an amino acid corresponding thereto is substituted with tyrosine and the asparagine at position 515 or an amino acid corresponding thereto is substituted with phenylalanine (K487Y_N515F);

a double substitution in which the lysine at position 487 or an amino acid corresponding thereto is substituted with tyrosine and the asparagine at position 515 or an amino acid corresponding thereto is substituted with tryptophan (K487Y_N515W);

a double substitution in which the valine at position 488 or an amino acid corresponding thereto is substituted with lysine and the asparagine at position 515 or an amino acid corresponding thereto is substituted with lysine (V488K_N515K);

a double substitution in which the valine at position 488 or an amino acid corresponding thereto is substituted with lysine and the asparagine at position 515 or an amino acid corresponding thereto is substituted with tryptophan (V488K_N515W);

a double substitution in which the valine at position 488 or an amino acid corresponding thereto is substituted with tryptophan and the asparagine at position 515 or an amino acid corresponding thereto is substituted with lysine (V488W_N515K);

a double substitution in which the valine at position 488 or an amino acid corresponding thereto is substituted with tryptophan and the asparagine at position 515 or an amino acid corresponding thereto is substituted with tryptophan (V488W_N515W);

a double substitution in which the valine at position 488 or an amino acid corresponding thereto is substituted with tyrosine and the asparagine at position 515 or an amino acid corresponding thereto is substituted with tryptophan (V488Y_N515W);

a double substitution in which the asparagine at position 550 or an amino acid corresponding thereto is substituted with serine and the tyrosine at position 598 or an amino acid corresponding thereto is substituted with asparagine (N550S_Y598N);

a double substitution in which the asparagine at position 550 or an amino acid corresponding thereto is substituted with serine and the tyrosine at position 615 or an amino acid corresponding thereto is substituted with glycine (N550S_Y615G);

a double substitution in which the asparagine at position 550 or an amino acid corresponding thereto is substituted with serine and the tyrosine at position 615 or an amino acid corresponding thereto is substituted with leucine (N550S_Y615L);

a double substitution in which the asparagine at position 550 or an amino acid corresponding thereto is substituted with serine and the tyrosine at position 615 or an amino acid corresponding thereto is substituted with proline (N550S_Y615P);

a triple substitution in which the arginine at position 484 or an amino acid corresponding thereto is substituted with alanine, the glycine at position 485 or an amino acid corresponding thereto is substituted with alanine, and the lysine at position 487 or an amino acid corresponding thereto is substituted with aspartic acid (R484A_G485A_K487D);

a triple substitution in which the arginine at position 484 or an amino acid corresponding thereto is substituted with aspartic acid, the glycine at position 485 or an amino acid corresponding thereto is substituted with aspartic acid, and the lysine at position 487 or an amino acid corresponding thereto is substituted with aspartic acid (R484D_G485D_K487D);

a triple substitution in which the glycine at position 485 or an amino acid corresponding thereto is substituted with arginine, the aspartic acid at position 486 or an amino acid corresponding thereto is substituted with arginine, and the lysine at position 487 or an amino acid corresponding thereto is substituted with arginine (G485R_D486R_K487R);

a quadruple substitution in which the arginine at position 484 or an amino acid corresponding thereto is substituted with alanine, the glycine at position 485 or an amino acid corresponding thereto is substituted with alanine, the aspartic acid at position 486 or an amino acid corresponding thereto is substituted with alanine, and the lysine at position 487 or an amino acid corresponding thereto is substituted with alanine (R484A_G485A_D486A_K487A);

a quadruple substitution in which the arginine at position 484 or an amino acid corresponding thereto is substituted with alanine, the glycine at position 485 or an amino acid corresponding thereto is substituted with alanine, the aspartic acid at position 486 or an amino acid corresponding thereto is substituted with proline, and the lysine at position 487 or an amino acid corresponding thereto is substituted with proline (R484A_G485A_D486P_K487P);

a triple substitution in which the arginine at position 484 or an amino acid corresponding thereto is substituted with alanine, the glycine at position 485 or an amino acid corresponding thereto is substituted with alanine, and the lysine at position 487 or an amino acid corresponding thereto is substituted with aspartic acid (R484A_G485A_K487D);

a triple substitution in which the arginine at position 484 or an amino acid corresponding thereto is substituted with cysteine, the aspartic acid at position 486 or an amino acid corresponding thereto is substituted with histidine, and the lysine at position 487 or an amino acid corresponding thereto is substituted with arginine (R484C_D486H_K487R);

a triple substitution in which the glycine at position 485 or an amino acid corresponding thereto is substituted with arginine, the aspartic acid at position 486 or an amino acid corresponding thereto is substituted with tryptophan, and the lysine at position 487 or an amino acid corresponding thereto is substituted with tryptophan (G485R_D486W_K487W);

a triple substitution in which the glycine at position 485 or an amino acid corresponding thereto is substituted with arginine, the aspartic acid at position 486 or an amino acid corresponding thereto is substituted with alanine, and the lysine at position 487 or an amino acid corresponding thereto is substituted with alanine (G485R_D486A_K487A);

a triple substitution in which the glycine at position 485 or an amino acid corresponding thereto is substituted with arginine, the aspartic acid at position 486 or an amino acid corresponding thereto is substituted with proline, and the lysine at position 487 or an amino acid corresponding thereto is substituted with proline (G485R_D486P_K487P);

a quadruple substitution in which the arginine at position 484 or an amino acid corresponding thereto is substituted with alanine, the glycine at position 485 or an amino acid corresponding thereto is substituted with alanine, the aspartic acid at position 486 or an amino acid corresponding thereto is substituted with alanine, and the lysine at position 487 or an amino acid corresponding thereto is substituted with alanine (R484A_G485A_D486A_K487A);

a quadruple substitution in which the arginine at position 484 or an amino acid corresponding thereto is substituted with alanine, the glycine at position 485 or an amino acid corresponding thereto is substituted with alanine, the aspartic acid at position 486 or an amino acid corresponding thereto is substituted with arginine, and the lysine at position 487 or an amino acid corresponding thereto is substituted with arginine (R484A_G485A_D486R_K487R);

a quadruple substitution in which the arginine at position 484 or an amino acid corresponding thereto is substituted with aspartic acid, the glycine at position 485 or an amino acid corresponding thereto is substituted with aspartic acid, the aspartic acid at position 486 or an amino acid corresponding thereto is substituted with arginine, and the lysine at position 487 or an amino acid corresponding thereto is substituted with arginine (R484D_G485D_D486R_K487R);

a quadruple substitution in which the arginine at position 484 or an amino acid corresponding thereto is substituted with aspartic acid, the glycine at position 485 or an amino acid corresponding thereto is substituted with aspartic acid, the aspartic acid at position 486 or an amino acid corresponding thereto is substituted with proline, and the lysine at position 487 or an amino acid corresponding thereto is substituted with proline (R484D_G485D_D486P_K487P);

a quadruple substitution in which the arginine at position 484 or an amino acid corresponding thereto is substituted with aspartic acid, the glycine at position 485 or an amino acid corresponding thereto is substituted with aspartic acid, the aspartic acid at position 486 or an amino acid corresponding thereto is substituted with alanine, and the lysine at position 487 or an amino acid corresponding thereto is substituted with alanine (R484D_G485D_D486A_K487A);

a quadruple substitution in which the arginine at position 484 or an amino acid corresponding thereto is substituted with aspartic acid, the glycine at position 485 or an amino acid corresponding thereto is substituted with aspartic acid, the aspartic acid at position 486 or an amino acid corresponding thereto is substituted with tryptophan, and the lysine at position 487 or an amino acid corresponding thereto is substituted with tryptophan (R484D_G485D_D486W_K487W); and a quadruple substitution in which the arginine at position 484 or an amino acid corresponding thereto is substituted with proline, the glycine at position 485 or an amino acid corresponding thereto is substituted with proline, the aspartic acid at position 486 or an amino acid corresponding thereto is substituted with arginine, and the lysine at position 487 or an amino acid corresponding thereto is substituted with arginine (R484P_G485P_D486R_K487R).

[20] A modified β-galactosidase, wherein the modified β-galactosidase has undergone any of the following modifications in a β-galactosidase consisting of the amino acid sequence of any of SEQ ID NOs. 1 to 4 or an amino acid sequence having 90% or more identity to the amino acid sequence set forth in any of SEQ ID NOs. 1 to 4:

(a) a deletion of the region of arginine at position 484 (R484) to lysine at position 487 (K487) or a region corresponding thereto;

(b) an insertion of an amino acid(s) at the position between asparagine at position 514 (N514) and asparagine at position 515 (N515) or at a position corresponding thereto;

(c) an insertion of an amino acid(s) at the position between proline at position 604 (P604) and tyrosine at position 605 (Y605) or at a position corresponding thereto;

(d) a deletion of the glycine at position 485 (G485) or an amino acid corresponding thereto, and in addition, a substitution of aspartic acid at position 486 (D486) or an amino acid corresponding thereto;

(e) a deletion of the region of glycine at position 485 (G485) to aspartic acid at position 486 (D486) or a region corresponding thereto, and in addition, a substitution of lysine at position 487 (K487) or an amino acid corresponding thereto;

(f) a deletion of the region of glycine at position 485 (G485) to aspartic acid at position 486 (D486) or a region corresponding thereto, and in addition, a substitution of arginine at position 484 (R484) or an amino acid corresponding thereto, and a substitution of lysine at position 487 (K487) or an amino acid corresponding thereto;

(g) an insertion of an amino acid(s) at the position between arginine at position 484 (R484) and glycine at position 485 (G485) or at a position corresponding thereto; and (h) an insertion of an amino acid(s) at the position between glycine at position 485 (G485) and aspartic acid at position 486 (D486) or at a position corresponding thereto.

[21] The modified β-galactosidase according to [20], wherein for (d) to (f), the amino acid that has been substituted for arginine at position 484 (R484) is tryptophan or proline, the amino acid that has been substituted for aspartic acid at position 486 (D486) is histidine, and the amino acid that has been substituted for lysine at position 487 (K487) is arginine, tryptophan, or proline; and for (b), (c), (g), and (h), the number of amino acids to be inserted is from 1 to 10.

[22] A modified β-galactosidase, wherein the modified β-galactosidase has undergone any of the following modifications in a β-galactosidase consisting of the amino acid sequence of SEQ ID NO. 1:

(i) a substitution of the lysine at position 487 (K487) with glycine or proline;

(ii) a substitution of the asparagine at position 514 (N514) with tryptophan; and (iii) a substitution of the asparagine at position 515 (N515) with lysine or tryptophan.

[23] A gene coding the modified β-galactosidase according to any one of [1] to [22].

[24] A recombinant DNA comprising the gene according to [23].

[25] A microorganism carrying the recombinant DNA according to [24].

[26] An enzyme preparation comprising the modified β-galactosidase according to any one of [1] to [22].

[27] A method for the production of an oligosaccharide, characterized in that the modified β-galactosidase according to any one of [1] to [22] is allowed to act on a disaccharide, oligosaccharide, or polysaccharide having at least one of β-1,3-, β-1,4-, and β-1,6-bonds.

BRIEF DESCRIPTION OF DRAWINGS

FIG. 3 shows variants with decreased or increased hydrolytic activities for allolactose. (A) Measurement results for variants meeting the condition that allolactose decomposing activity÷1%-lactose decomposing activity is 50% or less. (B) Measurement results for variants meeting a condition that allolactose decomposing activity÷1%-lactose decomposing activity is 150% or greater. WT: wild-type enzyme.

FIG. 4 shows variants by which the content of tetrasaccharides in the composition of the galacto-oligosaccharides produced was altered. WT: wild-type enzyme.

FIG. 5 shows variants by which the content of allolactose in the composition of the galacto-oligosaccharides produced was altered. WT: wild-type enzyme.

FIG. 6 shows variants by which the content of tetrasaccharides in the composition of the galacto-oligosaccharides produced was altered. WT: wild-type enzyme.

FIG. 7 shows variants with single amino acid substitution and meeting condition 3 (see below). WT: wild-type enzyme.

FIG. 8 shows variants with single amino acid substitution and meeting condition 4 (see below). WT: wild-type enzyme.

FIG. 9 shows variants with single amino acid substitution which produced oligosaccharides with an increased content of tetrasaccharides. WT-A: wild-type enzyme of BgaD type A.

FIG. 10 shows variants in which a substitution meeting condition 3 (see below) and a substitution meeting condition 5 (see below) were combined (case 1), a substitution meeting condition 3 (see below) and a substitution meeting condition 6 (see below) were combined (case 3), a substitution meeting condition 4 (see below) and a substitution meeting condition 5 (see below) were combined (case 4), substitutions meeting condition 3 (see below) were combined (case 5-1), and substitutions meeting condition 4 (see below) were combined (case 5-2). WT: wild-type enzyme.

FIG. 11 shows variants with two amino acid substitutions and meeting condition 3 (see below; left), and variants with three or four amino acid substitutions and meeting condition 4 (see below; right). WT: wild-type enzyme.

FIG. 12 shows variants with three or four amino acid substitutions and meeting condition 3 (see below; upper) and condition 4 (see below; bottom). WT: wild-type enzyme.

FIG. 13 shows insertion or deletion variants and meeting condition 3 (see below; upper) and condition 4 (see below; bottom). WT: wild-type enzyme.

DESCRIPTION OF EMBODIMENTS

Figure 1:
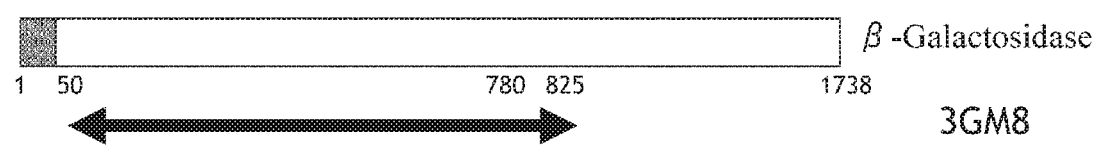
FIG. 1 shows a comparison of a β-galactosidase from *Bacillus circulans* and 3GM8 (a beta-glycosidase from *Bacteroides vulgatus* (Identities=282/824 (34%), Positives=425/824 (52%)).

For convenience of description, some of the terms used in relation to the present invention are defined as follows.

Terminology

The term "modified β-galactosidase" refers to an enzyme obtained by modification or mutation of a particular β-galactosidase (which is referred to as a "reference β-galactosidase" for convenience of description). The reference β-galactosidase is a β-galactosidase produced by *Bacillus circulans*. From earlier studies, it is known that the β-galactosidase from *Bacillus circulans* is made up of four enzymes (isozymes) with different molecular weights. The present invention uses any of these four enzymes (isozymes) as a reference β-galactosidase. Typically, an enzyme having the amino acid sequence of any of SEQ ID NOs. 1 to 4 is used as a reference β-galactosidase. However, it is also possible to as a reference β-galactosidase, use an enzyme that has an amino acid sequence having 90% or more identity to the amino acid sequence of any of SEQ ID NOs. 1 to 4, wherein the enzyme exhibits β-galactosidase activity. As a reference β-galactosidase, it is possible to preferably use an enzyme that has an amino acid sequence having 95% or more identity to the amino acid sequence of any of SEQ ID NOs. 1 to 4, wherein the enzyme exhibits β-galactosidase activity, more preferably an enzyme that has an amino acid sequence having 98% or more identity to the amino acid sequence of any of SEQ ID NOs. 1 to 4, wherein the enzyme exhibits β-galactosidase activity, and most preferably an enzyme that has an amino acid sequence having 99% or more identity to the amino acid sequence of any of SEQ ID NOs. 1 to 4, wherein the enzyme exhibits β-galactosidase activity. SEQ ID NO. 1 represents the amino acid sequence of an isozyme of β-galactosidase with a molecular weight of 195 kD (also referred to hereinafter as BgaD-A); SEQ ID NO. 2 represents the amino acid sequence of an isozyme of β-galactosidase with a molecular weight of 160 kD (also referred to hereinafter as BgaD-B); SEQ ID NO. 3 represents the amino acid sequence of an isozyme of β-galactosidase with a molecular weight of 135 kD (also referred to hereinafter as BgaD-C); and SEQ ID NO. 4 represents the amino acid sequence of an isozyme of β-galactosidase with a molecular weight of 86 kD (also referred to hereinafter as BgaD-D). The base sequences coding BgaD-A, BgaD-B, BgaD-C, and BgaD-D are represented in SEQ ID NOs. 5, 6, 7, and 8, respectively.

In the present invention, an "amino acid substitution" is carried out as modification or mutation. Therefore, some amino acid residues are found to be different when a modified β-galactosidase and a reference β-galactosidase therefor are compared. In the specification, a modified β-galactosidase is also referred to as a modified enzyme, an variant β-galactosidase, a variant, or others.

In the specification, amino acids are designated according to the common practice, as their single letters as described below:

methionine: M; serine: S; alanine: A; threonine: T; valine: V; tyrosine: Y; leucine: L; asparagine: N; isoleucine: I; glutamine: Q; proline: P; aspartic acid: D; phenylalanine: F; glutamic acid: E; tryptophan: W; lysine: K; cysteine: C; arginine: R; glycine: G; and histidine: H.

In addition, an amino acid residue at a mutation site (an amino acid residue to be substituted with another amino acid) is expressed in a combination of the above-described single letter representing the kind of the amino acid residue and the figure representing the position of the amino acid residue. For example, if proline at position 182 is a mutation site, then the amino acid is designated as "P182."

(Modified β-Galactosidases)

A first aspect of the present invention is directed to a modified β-galactosidase (modified enzyme). A modified enzyme of the present invention typically has an amino acid sequence in which one or more amino acids selected from the group consisting of the following (1) to (21), in a β-galactosidase consisting of the amino acid sequence of any of SEQ ID NOs. 1 to 4 or an amino acid sequence having 90% or more identity to the amino acid sequence set forth in any of SEQ ID NOs. 1 to 4:

(1) proline at position 182 (P182),
(2) tyrosine at position 187 (Y187),
(3) serine at position 188 (S188),
(4) tryptophan at position 405 (W405),
(5) alanine at position 406 (A406),
(6) glutamine at position 407 (Q407),
(7) tyrosine at position 449 (Y449),
(8) threonine at position 483 (T483),
(9) serine at position 512 (S512),
(10) serine at position 531 (S531),
(11) threonine at position 533 (T533),
(12) serine at position 534 (S534),
(13) asparagine at position 550 (N550),
(14) glutamine at position 551 (Q551),
(15) tryptophan at position 593 (W593),
(16) tyrosine at position 598 (Y598),
(17) proline at position 602 (P602),
(18) proline at position 604 (P604),
(19) tyrosine at position 609 (Y609),
(20) lysine at position 612 (K612), and
(21) tyrosine at position 615 (Y615).

As shown in the examples described below, the above-described amino acid residues to be substituted have been identified by prediction of the steric structure of the wild-type enzymes and validation experiments on variant enzymes. In an embodiment of the present invention, the structure of a reference β-galactosidase enzyme is modified by substitution of one or more of these amino acids to alter a property of the reference β-galactosidase. Here, the "property" is an activity to synthesize oligosaccharides and/or a hydrolytic activity for allolactose.

In a reference β-galactosidase that has an amino acid sequence having 90% or more identity, preferably 95% or more identity, more preferably 98% or more identity, most preferably 99% or more identity, to the amino acid sequence of any of SEQ ID NOs. 1 to 4, insertion or deletion of an amino acid(s) may result in differences in the positions of amino acids between the sequences of the reference β-galactosidase and an enzyme consisting of the amino acid sequence of any of SEQ ID NOs. 1 to 4. For this reason, in one embodiment of the present invention, an amino acid(s) corresponding to one or more amino acids selected from the group consisting of the above-described amino acids (1) to (21) in a reference β-galactosidase is/are to be substituted. Here, the term "corresponding" means that between two proteins (enzymes) to be compared, the corresponding amino acids in the two proteins make a comparable contribution in exerting their function. For example, it is possible that when an amino acid sequence to be compared is aligned relative to a reference amino acid sequence (for example, the amino acid sequence of SEQ ID NO. 1) with taking into account a partial homology in their primary structures (amino acid sequences), whereby an optimal comparison between them can be made (in this case, the alignment can be optimized by insertion of a gap or gaps if needed), an amino acid at the position corresponding to that of a given amino acid in the reference amino acid sequence is identified as an "amino acid corresponding" thereto. Instead of or in addition to making a comparison between the primary structures of two proteins (enzymes), an "amino acid corresponding" in the two proteins (enzymes) can also be identified by making a comparison between their steric structures (three-dimensional structures). The use of steric structure information allows one to obtain comparison results with high reliability. In this case, a procedure can be employed in which the alignment is carried out with comparing the atomic coordinates in the steric structures of a plurality of enzymes.

A kind of an amino acid after substitution is not particularly limited. Thus, it may be "conservative amino acid substitution" or "non-conservative amino acid substitution". The "conservative amino acid substitution" herein refers to substituting a certain amino acid residue with an amino acid residue having a side chain with the same characteristics. Amino acid residues are classified into some families according to their side chains, such as basic side chains (e.g., lysine, arginine, and histidine), acidic side chains (e.g., asparaginic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is typically substitution between amino acid residues in the same family.

In a first embodiment of the present invention, the one or more amino acids to be substituted are selected from the group consisting of tyrosine at position 449 (Y449), serine at position 531 (S531), tryptophan at position 593 (W593), proline at position 602 (P602), proline at position 604 (P604), and lysine at position 612 (K612). These amino acids have been identified as meeting the condition that "a variant enzyme has an allolactose decomposing activity of 50% or less relative to that of the parent wild-type enzyme" (condition 1), in experiments described in the Examples which follows, and are related to the substrate specificity of the hydrolytic activity for allolactose. Accordingly, it can be said that modified enzymes in this embodiment are highly useful in that they have a reduced allolactose-hydrolytic activity. The amino acids that have been substituted for the above-mentioned amino acids are preferably as indicated below. An amino acid to be substituted in this embodiment is referred to as a "group 1 amino acid."

The amino acid that has been substituted for tyrosine at position 449 (Y449) is aspartic acid, glutamic acid, asparagine, or tryptophan.

The amino acid that has been substituted for serine at position 531 (S531) is alanine, aspartic acid, glutamic acid, phenylalanine, glycine, isoleucine, methionine, asparagine, or glutamine.

The amino acid that has been substituted for tryptophan at position 593 (W593) is phenylalanine.

The amino acid that has been substituted for proline at position 602 (P602) is glutamic acid or glycine.

The amino acid that has been substituted for proline at position 604 (P604) is alanine, glycine, histidine, isoleucine, methionine, serine, threonine, valine, tryptophan, or tyrosine.

The amino acid that has been substituted for lysine at position 612 (K612) is methionine.

In a second embodiment of the present invention, the one or more amino acids to be substituted are selected from the group consisting of tyrosine at position 187 (Y187), serine at position 188 (S188), threonine at position 533 (T533), proline at position 602 (P602), and lysine at position 612 (K612). These amino acids have been identified as meeting the condition that "a variant enzyme has an allolactose decomposing activity of 150% or greater relative to that of the parent wild-type enzyme" (condition 2), in experiments described in the Examples which follows, and are related to the substrate specificity of the hydrolytic activity for allolactose. Accordingly, it can be said that modified enzymes in this embodiment are highly useful in that they have an enhanced allolactose-hydrolytic activity. The amino acids that have been substituted for the above-mentioned amino acids are preferably as indicated below. An amino acid to be substituted in this embodiment is referred to as a "group 2 amino acid."

The amino acid that has been substituted for tyrosine at position 187 (Y187) is aspartic acid, glutamic acid, or glycine.

The amino acid that has been substituted for serine at position 188 (S188) is proline or threonine.

The amino acid that has been substituted for threonine at position 533 (T533) is methionine or glutamine.

The amino acid that has been substituted for proline at position 602 (P602) is cysteine, isoleucine, asparagine, serine, threonine, or valine.

The amino acid that has been substituted for lysine at position 612 (K612) is phenylalanine.

In a third embodiment of the present invention, the one or more amino acids to be substituted are selected from the group consisting of proline at position 182 (P182), tyrosine at position 187 (Y187), serine at position 188 (S188), tryptophan at position 405 (W405), glutamine at position 407 (Q407), tyrosine at position 449 (Y449), threonine at position 483 (T483), serine at position 512 (S512), serine at position 531 (S531), asparagine at position 550 (N550), proline at position 602 (P602), and proline at position 604 (P604). These amino acids have been identified as meeting the condition that "a variant enzyme produces oligosaccharides in which the content of trisaccharides and higher saccharides is approximately equal and the content of tetrasaccharides is smaller, relative to the case of the parent wild-type enzyme" (condition 3), in experiments described in the Examples which follows, and are related to the amount of production of tetrasaccharides. Accordingly, it can be said that modified enzymes in this embodiment are highly useful in that their use results in a decrease in the content of tetrasaccharides. The amino acids that have been substituted for the above-mentioned amino acids are preferably as indicated below. I An amino acid to be substituted in this embodiment is referred to as a "group 3 amino acid."

The amino acid that has been substituted for proline at position 182 (P182) is leucine.

The amino acid that has been substituted for tyrosine at position 187 (Y187) is aspartic acid or leucine.

The amino acid that has been substituted for serine at position 188 (S188) is isoleucine.

The amino acid that has been substituted for tryptophan at position 405 (W405) is alanine, aspartic acid, glutamic acid, glycine, histidine, leucine, asparagine, serine, or threonine.

The amino acid that has been substituted for glutamine at position 407 (Q407) is glycine or arginine.

The amino acid that has been substituted for tyrosine at position 449 (Y449) is glutamic acid, isoleucine, glutamine, arginine, or serine.

The amino acid that has been substituted for threonine at position 483 (T483) is glutamine.

The amino acid that has been substituted for serine at position 512 (S512) is phenylalanine, threonine, or valine. The amino acid that has been substituted for serine at position 531 (S531) is proline.

The amino acid that has been substituted for asparagine at position 550 (N550) is leucine, arginine, or serine.

The amino acid that has been substituted for proline at position 602 (P602) is leucine, asparagine, or glutamine.

The amino acid that has been substituted for proline at position 604 (P604) is isoleucine or methionine.

From the results of further studies, as amino acids to be substituted which meet the condition that "a variant enzyme produces oligosaccharides in which the content of trisaccharides and higher saccharides is approximately equal and the content of tetrasaccharides is smaller, relative to the case of the parent wild-type enzyme" (condition 3) (i.e., group 3 amino acids), there have been identified tryptophan at position 85 (W85), phenylalanine at position 91 (F91), tyrosine at position 103 (Y103), tyrosine at position 134 (Y134), tyrosine at position 153 (Y153), proline at position 182 (P182), tryptophan at position 186 (W186), tyrosine at position 192 (Y192), tyrosine at position 295 (Y295), histidine at position 345 (H345), glycine at position 349 (G349), phenylalanine at position 402 (F402), glutamine at position 407 (Q407), glycine at position 479 (G479), glutamic acid at position 480 (E480), lysine at position 482 (K482), threonine at position 483 (T483), arginine at position 484 (R484), glycine at position 485 (G485), aspartic acid at position 486 (D486), lysine at position 487 (K487), valine at position 488 (V488), tyrosine at position 496 (Y496), serine at position 512 (S512), glutamic acid at position 513 (E513), asparagine at position 514 (N514), asparagine at position 515 (N515), tyrosine at position 516 (Y516), aspartic acid at position 517 (D517), tyrosine at position 519 (Y519), threonine at position 533 (T533), tyrosine at position 547 (Y547), tyrosine at position 549 (Y549), tyrosine at position 555 (Y555), arginine at position 572 (R572), threonine at position 573 (T573), tyrosine at position 598 (Y598), tyrosine at position 605 (Y605), tyrosine at position 606 (Y606), tyrosine at position 609 (Y609), phenylalanine at position 616 (F616), phenylalanine at position 624 (F624), tryptophan at position 648 (W648), and tryptophan at position 650 (W650). Therefore, one embodiment of the present invention provides a modified enzyme consisting of an amino acid sequence in which one or more amino acids selected from the group consisting of the above-mentioned amino acids, or an amino acid(s) corresponding thereto, in a β-galactosidase consisting of the amino acid sequence of any of SEQ ID NOs. 1 to 4 or an amino acid sequence having 90% or more identity to the amino acid sequence set forth in any of SEQ ID NOs. 1 to 4. The amino acids that have been substituted for the above-mentioned amino acids are preferably as indicated below.

The amino acid that has been substituted for tryptophan at position 85 (W85) is glycine.

The amino acid that has been substituted for phenylalanine at position 91 (F91) is alanine or isoleucine.

The amino acid that has been substituted for tyrosine at position 103 (Y103) is glycine.

The amino acid that has been substituted for tyrosine at position 134 (Y134) is glycine.

The amino acid that has been substituted for tyrosine at position 153 (Y153) is glycine.

The amino acid that has been substituted for proline at position 182 (P182) is tryptophan or tyrosine.

The amino acid that has been substituted for tryptophan at position 186 (W186) is methionine.

The amino acid that has been substituted for tyrosine at position 192 (Y192) is glycine.

The amino acid that has been substituted for tyrosine at position 295 (Y295) is glycine.

The amino acid that has been substituted for histidine at position 345 (H345) is glycine.

The amino acid that has been substituted for glycine at position 349 (G349) is tryptophan.

The amino acid that has been substituted for phenylalanine at position 402 (F402) is glycine.

The amino acid that has been substituted for glutamine at position 407 (Q407) is isoleucine, leucine, methionine, valine, or tyrosine.

The amino acid that has been substituted for glycine at position 479 (G479) is leucine, proline, or glutamine.

The amino acid that has been substituted for glutamic acid at position 480 (E480) is asparagine.

The amino acid that has been substituted for lysine at position 482 (K482) is methionine or valine.

The amino acid that has been substituted for threonine at position 483 (T483) is glycine or serine.

The amino acid that has been substituted for arginine at position 484 (R484) is phenylalanine, isoleucine, methionine, asparagine, or glutamine.

The amino acid that has been substituted for glycine at position 485 (G485) is aspartic acid, asparagine, glutamine, or threonine.

The amino acid that has been substituted for aspartic acid at position 486 (D486) is alanine, glutamic acid, phenylalanine, isoleucine, lysine, leucine, methionine, proline, glutamine, arginine, threonine, tryptophan, or tyrosine.

The amino acid that has been substituted for lysine at position 487 (K487) is cysteine, glutamic acid, phenylalanine, histidine, isoleucine, leucine, asparagine, glutamine, arginine, threonine, valine, tryptophan, or tyrosine.

The amino acid that has been substituted for valine at position 488 (V488) is glycine, isoleucine, leucine, arginine, serine, threonine, tryptophan, or tyrosine.

The amino acid that has been substituted for tyrosine at position 496 (Y496) is glycine.

The amino acid that has been substituted for serine at position 512 (S512) is cysteine, aspartic acid, glutamic acid, asparagine, proline, glutamine, or tryptophan.

The amino acid that has been substituted for glutamic acid at position 513 (E513) is alanine, cysteine, aspartic acid, phenylalanine, glycine, histidine, lysine, leucine, methionine, asparagine, proline, glutamine, arginine, serine, threonine, or valine.

The amino acid that has been substituted for asparagine at position 514 (N514) is glutamic acid, leucine, or lysine.

The amino acid that has been substituted for asparagine at position 515 (N515) is alanine, aspartic acid, glutamic acid, glycine, isoleucine, leucine, proline, or valine.

The amino acid that has been substituted for tyrosine at position 516 (Y516) is tryptophan.

The amino acid that has been substituted for aspartic acid at position 517 (D517) is lysine or tryptophan.

The amino acid that has been substituted for tyrosine at position 519 (Y519) is glycine.

The amino acid that has been substituted for threonine at position 533 (T533) is glutamic acid.

The amino acid that has been substituted for tyrosine at position 547 (Y547) is glycine.

The amino acid that has been substituted for tyrosine at position 549 (Y549) is glycine.

The amino acid that has been substituted for tyrosine at position 555 (Y555) is glycine.

The amino acid that has been substituted for arginine at position 572 (R572) is cysteine, leucine, methionine, threonine, tryptophan, or tyrosine.

The amino acid that has been substituted for threonine at position 573 (T573) is glutamic acid.

The amino acid that has been substituted for tyrosine at position 598 (Y598) is histidine or asparagine.

The amino acid that has been substituted for tyrosine at position 605 (Y605) is cysteine, aspartic acid, histidine, isoleucine, lysine, proline, arginine, or threonine.

The amino acid that has been substituted for tyrosine at position 606 (Y606) is alanine, cysteine, aspartic acid, glutamic acid, phenylalanine, glycine, histidine, isoleucine, lysine, leucine, methionine, or serine.

The amino acid that has been substituted for tyrosine at position 609 (Y609) is glutamic acid, asparagine, or serine.

The amino acid that has been substituted for phenylalanine at position 616 (F616) is glycine.

The amino acid that has been substituted for phenylalanine at position 624 (F624) is glycine.

The amino acid that has been substituted for tryptophan at position 648 (W648) is glycine.

The amino acid that has been substituted for tryptophan at position 650 (W650) is glycine.

In a fourth embodiment of the present invention, the one or more amino acids to be substituted are selected from the group consisting of threonine at position 483 (T483), serine at position 512 (S512), glutamine at position 551 (Q551), tyrosine at position 598 (Y598), and tyrosine at position 615 (Y615). These amino acids have been identified as meeting the condition that "a variant enzyme produces oligosaccharides in which the content of trisaccharides and higher saccharides is approximately equal and the content of tetrasaccharides is higher, relative to the case of the parent wild-type enzyme" (condition 4), in experiments described in the Examples which follow, and are related to the amount of production of tetrasaccharides. Accordingly, it can be said that modified enzymes in this embodiment are highly useful in that their use results in an increase in the content of tetrasaccharides. The amino acids that have been substituted for the above-mentioned amino acids are preferably as indicated below. An amino acid to be substituted in the fourth embodiment is referred to as a "group 4 amino acid."

The amino acid that has been substituted for threonine at position 483 (T483) is lysine, methionine, or arginine.

The amino acid that has been substituted for serine at position 512 (S512) is glycine or lysine.

The amino acid that has been substituted for glutamine at position 551 (Q551) is asparagine.

The amino acid that has been substituted for tyrosine at position 598 (Y598) is asparagine.

The amino acid that has been substituted for tyrosine at position 615 (Y615) is threonine.

From the results of further studies, as the amino acids that are to be substituted and that meet the condition that "a variant enzyme produces oligosaccharides in which the content of trisaccharides and higher saccharides is approximately equal and the content of tetrasaccharides is higher, relative to the case of the parent wild-type enzyme" (condition 4) (i.e., group 4 amino acids), there have been identified tryptophan at position 76 (W76), glutamic acid at position 480 (E480), threonine at position 483 (T483), glycine at position 485 (G485), arginine at position 484 (R484), lysine at position 487 (K487), valine at position 488 (V488), serine at position 512 (S512), asparagine at position 514 (N514), asparagine at position 515 (N515), glycine at position 569 (G569), and phenylalanine at position 596 (F596). Therefore, one embodiment of the present invention provides a modified enzyme consisting of an amino acid sequence in which one or more amino acids selected from the group consisting of the above-mentioned amino acids, or an amino acid(s) corresponding thereto, has/have been substituted by other amino acid in a β-galactosidase consisting of the amino acid sequence of any of SEQ ID NOs. 1 to 4 or an amino acid sequence having 90% or more identity to the amino acid sequence set forth in any of SEQ ID NOs. 1 to 4. The amino acids that have been substituted for the above-mentioned amino acids are preferably as indicated below.

The amino acid that has been substituted for tryptophan at position 76 (W76) is glycine.

The amino acid that has been substituted for glutamic acid at position 480 (E480) is glutamine.

The amino acid that has been substituted for threonine at position 483 (T483) is tryptophan.

The amino acid that has been substituted for glycine at position 485 (G485) is proline or threonine.

The amino acid that has been substituted for arginine at position 484 (R484) is alanine, cysteine, aspartic acid, glycine, proline, serine, tyrosine, or lysine.

The amino acid that has been substituted for lysine at position 487 (K487) is glycine or proline.

The amino acid that has been substituted for valine at position 488 (V488) is proline.

The amino acid that has been substituted for serine at position 512 (S512) is leucine or methionine.

The amino acid that has been substituted for asparagine at position 514 (N514) is aspartic acid.

The amino acid that has been substituted for asparagine at position 515 (N515) is phenylalanine, arginine, tryptophan, tyrosine, or lysine.

The amino acid that has been substituted for glycine at position 569 (G569) is lysine, proline, or valine.

The amino acid that has been substituted for phenylalanine at position 596 (F596) is glycine.

In a fifth embodiment of the present invention, the one or more amino acids to be substituted are selected from the group consisting of tryptophan at position 405 (W405), threonine at position 483 (T483), serine at position 531 (S531), asparagine at position 550 (N550), and tyrosine at position 598 (Y598). These amino acids have been identified as meeting the condition that "a variant enzyme produces oligosaccharides in which the content of trisaccharides and higher saccharides is approximately equal and the content of allolactose is smaller, relative to the case of the parent wild-type enzyme" (condition 5), in experiments described in the Examples which follow, and are related to the content of allolactose. Accordingly, it can be said that modified enzymes in this embodiment are highly useful in that their use results in a decrease in the percentage of allolactose. The amino acids that have been substituted for the above-mentioned amino acids are preferably as indicated below. An amino acid to be substituted in the fifth embodiment is referred to as a "group 5 amino acid."

The amino acid that has been substituted for tryptophan at position 405 (W405) is alanine, aspartic acid, serine, or threonine.

The amino acid that has been substituted for threonine at position 483 (T483) is methionine.

The amino acid that has been substituted for serine at position 531 (S531) is aspartic acid, phenylalanine, glycine, leucine, lysine, or methionine.

The amino acid that has been substituted for asparagine at position 550 (N550) is phenylalanine.

The amino acid that has been substituted for tyrosine at position 598 (Y598) is phenylalanine or histidine.

In a sixth embodiment of the present invention, the one or more amino acids to be substituted are selected from the group consisting of proline at position 182 (P182), tyrosine at position 187 (Y187), serine at position 188 (S188), tryptophan at position 405 (W405), alanine at position 406 (A406), glutamine at position 407 (Q407), tyrosine at position 449 (Y449), threonine at position 483 (T483), serine at position 512 (S512), serine at position 534 (S534), asparagine at position 550 (N550), glutamine at position 551 (Q551), proline at position 602 (P602), tyrosine at position 609 (Y609), lysine at position 612 (K612), and tyrosine at position 615 (Y615). These amino acids have been identified as meeting the condition that "a variant enzyme produces oligosaccharides in which the content of trisaccharides and higher saccharides is approximately equal and the content of allolactose is higher, relative to the case of the parent wild-type enzyme" (condition), in experiments described in the Examples which follow, and are related to the content of allolactose. Accordingly, it can be said that modified enzymes in this embodiment are highly useful in that their use results in an increase in the percentage of allolactose. The amino acids that have been substituted for the above-mentioned amino acids are preferably as indicated below. An amino acid to be substituted in the sixth embodiment is referred to as a "group 6 amino acid."

The amino acid that has been substituted for proline at position 182 (P182) is leucine or serine.

The amino acid that has been substituted for tyrosine at position 187 (Y187) is aspartic acid, glutamic acid, or asparagine.

The amino acid that has been substituted for serine at position 188 (S188) is glutamic acid, glycine, isoleucine, or asparagine.

The amino acid that has been substituted for tryptophan at position 405 (W405) is histidine.

The amino acid that has been substituted for alanine at position 406 (A406) is proline.

The amino acid that has been substituted for glutamine at position 407 (Q407) is alanine, phenylalanine, glycine, lysine, or arginine.

The amino acid that has been substituted for tyrosine at position 449 (Y449) is glutamic acid or arginine.

The amino acid that has been substituted for threonine at position 483 (T483) is serine or glutamine.

The amino acid that has been substituted for serine at position 512 (S512) is glycine, threonine, or valine.

The amino acid that has been substituted for serine at position 534 (S534) is lysine or glutamine.

The amino acid that has been substituted for asparagine at position 550 (N550) is alanine, glycine, lysine, leucine, methionine, arginine, or serine.

The amino acid that has been substituted for glutamine at position 551 (Q551) is lysine or histidine.

The amino acid that has been substituted for proline at position 602 (P602) is cysteine, aspartic acid, or asparagine.

The amino acid that has been substituted for tyrosine at position 609 (Y609) is aspartic acid, glutamine, or threonine.

The amino acid that has been substituted for lysine at position 612 (K612) is phenylalanine or isoleucine.

The amino acid that has been substituted for tyrosine at position 615 (Y615) is glutamic acid, isoleucine, or threonine.

In the present invention, two or more amino acids may be substituted. As mentioned above, the amino acids to be substituted are classified into groups 1 to 6. Two or more amino acids to be substituted are selected, for example, from among the amino acids within one group. In this embodiment, two or more amino acids belonging to one group are substituted, whereby it is expected that modified enzymes are generated in which a property characteristic of the given group (for example, a reduced allolactose-decomposing activity in the case of the group 1 amino acids) is enhanced. On the other hand, two or more amino acids to be substituted may be selected from among the amino acids within two or more different groups. It is expected that such selections would lead to the generation of modified enzymes in which properties of the respective groups to which the selected amino acids belong are combined. Preferable specific examples in this embodiment are given below. In this context, although combinations of amino acids to be substituted are not limited in particular, it is preferable that amino acids from groups exhibiting opposite properties, that is, from groups 1 and 2, from groups 3 and 4, or from groups 5 and 6, are not combined.

(Case 1)

Amino acids from group 3 and from group 5 are selected as targets for substitution. Modified enzymes obtained are expected to exhibit a characteristic of producing oligosaccharides in which both the percentages of tetrasaccharides and of allolactose are reduced.

(Case 2)

Amino acids from group 4 and from group 6 are selected as targets for substitution. Modified enzymes obtained are expected to exhibit a characteristic of producing oligo-saccharides in which both the percentages of tetrasaccharides and of allolactose are increased.
(Case 3)
Amino acids from group 3 and from group 6 are selected as targets for substitution. Modified enzymes obtained are expected to exhibit a characteristic of producing oligo-saccharides in which the percentage of tetrasaccharides is reduced, whereas the percentage of allolactose is increased.
(Case 4)
Amino acids from group 4 and from group 5 are selected as targets for substitution. Modified enzymes obtained are expected to exhibit a characteristic of producing oligo-saccharides in which the percentage of tetrasaccharides is increased, whereas the percentage of allolactose is reduced.
(Case 5)
A plurality of amino acids from one group is substituted. Substitutions of amino acids for plurality of amino acids from one group are expected to bring about a greater alteration. For example, if a plurality of amino acids from among the group 3 amino acids is selected as targets for substitution, then modified enzymes obtained are expected to exhibit a characteristic of producing oligo-saccharides in which the percentage of tetrasaccharides is reduced to a greater degree.

Specific examples falling within the above-described case 1 can include a modified enzyme in which the serine at position 188 is substituted with isoleucine and the asparagine at position 550 is substituted with phenylalanine (S188I_N550F); a modified enzyme in which the glutamine at position 407 is substituted with arginine and the asparagine at position 550 is substituted with phenylalanine (Q407R_N550F); a modified enzyme in which the tyrosine at position 449 is substituted with glutamine and the tyrosine at position 598 is substituted with histidine (Y449Q_Y598H); and a modified enzyme in which the asparagine at position 550 is substituted with phenylalanine and the proline at position 602 is substituted with glutamine (N550F_P602Q).

Specific examples falling within the above-described case 3 can include a modified enzyme in which the glutamine at position 407 is substituted with arginine and the tyrosine at position 449 is substituted with glutamic acid (Q407R_Y449E).

Specific examples falling within the above-described case 4 can include a modified enzyme in which the asparagine at position 550 is substituted with phenylalanine and the tyrosine at position 598 is substituted with asparagine (N550F_Y598N).

Specific examples falling within the above-described case 5 (wherein a plurality of amino acids from among the group 3 amino acids are selected as targets for substitution) can include a modified enzyme in which the proline at position 182 is substituted with leucine and the tyrosine at position 449 is substituted with glutamic acid (P182L_Y449E); a modified enzyme in which the proline at position 182 is substituted with leucine and the tyrosine at position 449 is substituted with glutamine (P182L_Y449Q); a modified enzyme in which the tyrosine at position 187 is substituted with leucine and the glutamine at position 407 is substituted with arginine (Y187L_Q407R); a modified enzyme in which the tyrosine at position 187 is substituted with leucine and the tyrosine at position 449 is substituted with glutamic acid (Y187L_Y449E); a modified enzyme in which the tyrosine at position 187 is substituted with leucine and the tyrosine at position 449 is substituted with glutamine (Y187L_Y449Q); a modified enzyme in which the tyrosine at position 187 is substituted with leucine and the serine at position 512 is substituted with cysteine (Y187L_S512C); a modified enzyme in which the tyrosine at position 187 is substituted with leucine and the serine at position 512 is substituted with asparagine (Y187L_S512N); a modified enzyme in which the tyrosine at position 187 is substituted with leucine and the serine at position 512 is substituted with threonine (Y187L_S512T); a modified enzyme in which the serine at position 188 is substituted with isoleucine and the glutamine at position 407 is substituted with arginine (S188I_Q407R); a modified enzyme in which the serine at position 188 is substituted with isoleucine and the tyrosine at position 449 is substituted with glutamine (S188I_Y449Q); a modified enzyme in which the serine at position 188 is substituted with isoleucine and the threonine at position 483 is substituted with glutamic acid (S188I_T483E); a modified enzyme in which the glutamine at position 407 is substituted with leucine and the serine at position 512 is substituted with valine (Q407L_S512V); a modified enzyme in which the glutamine at position 407 is substituted with arginine and the threonine at position 483 is substituted with glycine (Q407R_T483G); a modified enzyme in which the glutamine at position 407 is substituted with arginine and the tyrosine at position 449 is substituted with glutamine (Q407R_Y449Q); a modified enzyme in which the glutamine at position 407 is substituted with arginine and the asparagine at position 550 is substituted with serine (Q407R_N550S); a modified enzyme in which the tyrosine at position 449 is substituted with glutamine and the asparagine at position 550 is substituted with serine (Y449Q_N550S); a modified enzyme in which the lysine at position 487 is substituted with tryptophan and the serine at position 512 is substituted with threonine (K487W_S512T); a modified enzyme in which the lysine at position 487 is substituted with tryptophan and the aspartic acid at position 517 is substituted with lysine (K487W_D517K); a modified enzyme in which the lysine at position 487 is substituted with tryptophan and the asparagine at position 515 is substituted with glycine (K487W_N515G); and a modified enzyme in which the lysine at position 487 is substituted with tryptophan and the aspartic acid at position 517 is substituted with tryptophan (K487W_D517W).

Similarly, specific examples falling within the above-described case 5 (wherein a plurality of amino acids from among the group 4 amino acids are selected as targets for substitution) can include a modified enzyme in which the lysine at position 487 is substituted with proline and the asparagine at position 515 is substituted with arginine (K487P_N515R).

Further specific examples of modified enzymes in which two or more amino acids are substituted can include a modified enzyme in which the phenylalanine at position 91 is substituted with serine and the glutamine at position 407 is substituted with methionine (F91S_Q407M), a modified enzyme in which the threonine at position 180 is substituted with valine and the tyrosine at position 187 is substituted with leucine (T180V_Y187L), a modified enzyme in which the threonine at position 180 is substituted with valine and the serine at position 188 is substituted with isoleucine (T180V_S188I), a modified enzyme in which the threonine at position 180 is substituted with valine and the glutamine at position 407 is substituted with arginine (T180V_Q407R), a modified enzyme in which the threonine at position 180 is substituted with valine and the tyrosine at position 449 is substituted with glutamic acid (T180V_Y449E), a modified enzyme in which the threonine at position 180 is substituted with valine and the threonine at position 483 is substituted with glycine (T180V_T483G), a modified enzyme in which the threonine at position 180 is substituted with valine and the serine at position 512 is substituted with valine (T180V_S512V), a modified enzyme in which the threonine at position 180 is substituted with valine and the asparagine at position 550 is substituted with phenylalanine (T180V_N550F), a modified enzyme in which the threonine at position 180 is substituted with valine and the tyrosine at position 615 is substituted with proline (T180V_Y615P), a modified enzyme in which the proline at position 182 is substituted with leucine and the arginine at position 376 is substituted with proline (P182L_R376P), a modified enzyme in which the proline at position 182 is substituted with tryptophan and the tyrosine at position 449 is substituted with glutamine (P182W_Y449Q), a modified enzyme in which the tyrosine at position 187 is substituted with leucine and the lysine at position 487 is substituted with alanine (Y187L_K487A), a modified enzyme in which the tyrosine at position 187 is substituted with leucine and the serine at position 512 is substituted with alanine (Y187L_S512A), a modified enzyme in which the tyrosine at position 187 is substituted with leucine and the threonine at position 533 is substituted with asparagine (Y187L_T533N), a modified enzyme in which the arginine at position 376 is substituted with proline and the glutamine at position 407 is substituted with leucine (R376P_Q407L), a modified enzyme in which the arginine at position 376 is substituted with proline and the tyrosine at position 449 is substituted with glutamine (R376P_Y449Q), a modified enzyme in which the arginine at position 376 is substituted with proline and the serine at position 512 is substituted with valine (R376P_S512V), a modified enzyme in which the arginine at position 376 is substituted with proline and the asparagine at position 550 is substituted with tryptophan (R376P_N550W), a modified enzyme in which the arginine at position 376 is substituted with proline and the asparagine at position 550 is substituted with tyrosine (R376P_N550Y), a modified enzyme in which the glutamine at position 407 is substituted with leucine and the threonine at position 533 is substituted with glutamic acid (Q407L_T533E), a modified enzyme in which the glutamine at position 407 is substituted with leucine and the tryptophan at position 570 is substituted with tyrosine (Q407L_W570Y), a modified enzyme in which the glutamine at position 407 is substituted with leucine and the tyrosine at position 615 is substituted with leucine (Q407L_Y615L), a modified enzyme in which the glutamine at position 407 is substituted with arginine and the tyrosine at position 615 is substituted with leucine (Q407R_Y615L), a modified enzyme in which the glutamine at position 407 is substituted with arginine and the tyrosine at position 615 is substituted with proline (Q407R_Y615P), a modified enzyme in which the tyrosine at position 449 is substituted with aspartic acid and the tyrosine at position 598 is substituted with phenylalanine (Y449D_Y598F), a modified enzyme in which the tyrosine at position 449 is substituted with glutamine and the threonine at position 533 is substituted with glutamic acid (Y449Q_T533E), a modified enzyme in which the tyrosine at position 449 is substituted with glutamine and the tyrosine at position 615 is substituted with glycine (Y449Q_Y615G), a modified enzyme in which the tyrosine at position 449 is substituted with glutamine and the tyrosine at position 615 is substituted with proline (Y449Q_Y615P), a modified enzyme in which the threonine at position 483 is substituted with glycine and the serine at position 512 is substituted with valine (T483G_S512V), a modified enzyme in which the threonine at position 483 is substituted with glycine and the asparagine at position 550 is substituted with serine (T483G_N550S), a modified enzyme in which the threonine at position 483 is substituted with glycine and the tyrosine at position 615 is substituted with leucine (T483G_Y615L), a modified enzyme in which the threonine at position 483 is substituted with glutamine and the proline at position 602 is substituted with glutamine (T483Q_P602Q), a modified enzyme in which the arginine at position 484 is substituted with histidine and the lysine at position 487 is substituted with histidine (R484H_K487H), a modified enzyme in which the arginine at position 484 is substituted with tryptophan and the lysine at position 487 is substituted with aspartic acid (R484W_K487D), a modified enzyme in which the arginine at position 484 is substituted with tryptophan and the threonine at position 575 is substituted with tryptophan (R484W_T575W), a modified enzyme in which the glycine at position 485 is substituted with lysine and the valine at position 488 is substituted with tryptophan (G485K_V488W), a modified enzyme in which the glycine at position 485 is substituted with lysine and the tyrosine at position 516 is substituted with tryptophan (G485K_Y516W), a modified enzyme in which the glycine at position 485 is substituted with lysine and the aspartic acid at position 517 is substituted with lysine (G485K_D517K), a modified enzyme in which the glycine at position 485 is substituted with lysine and the aspartic acid at position 517 is substituted with tryptophan (G485K_D517W), a modified enzyme in which the glycine at position 485 is substituted with lysine and the glycine at position 569 is substituted with tryptophan (G485K_G569W), a modified enzyme in which the glycine at position 485 is substituted with lysine and the glycine at position 571 is substituted with lysine (G485K_G571K), a modified enzyme in which the glycine at position 485 is substituted with lysine and the arginine at position 572 is substituted with tryptophan (G485K_R572W), a modified enzyme in which the glycine at position 485 is substituted with lysine and the threonine at position 573 is substituted with tryptophan (G485K_T573W), a modified enzyme in which the glycine at position 485 is substituted with tryptophan and the tyrosine at position 516 is substituted with tryptophan (G485W_Y516W), a modified enzyme in which the glycine at position 485 is substituted with tryptophan and the aspartic acid at position 517 is substituted with tryptophan (G485W_D517W), a modified enzyme in which the glycine at position 485 is substituted with tryptophan and the threonine at position 573 is substituted with lysine (G485W_T573K), a modified enzyme in which the glycine at position 485 is substituted with tryptophan and the threonine at position 573 is substituted with tryptophan (G485W_T573W), a modified enzyme in which the lysine at position 487 is substituted with alanine and the serine at position 512 is substituted with valine (K487A_S512V), a modified enzyme in which the lysine at position 487 is substituted with glycine and the asparagine at position 515 is substituted with glutamine (K487G_N515Q), a modified enzyme in which the lysine at position 487 is substituted with tryptophan and the threonine at position 573 is substituted with lysine (K487W_T573K), a modified enzyme in which the lysine at position 487 is substituted with tryptophan and the tryptophan at position 593 is substituted with phenylalanine (K487W_W593F), a modified enzyme in which the valine at position 488 is substituted with lysine and the asparagine at position 514 is substituted with lysine (V488K_N514K), a modified enzyme in which the valine at position 488 is substituted with lysine and the aspartic acid at position 517 is substituted with lysine (V488K_D517K), a modified enzyme in which the valine at position 488 is substituted with lysine and the glycine at position 569 is substituted with lysine (V488K_G569K), a modified enzyme in which the valine at position 488 is substituted with lysine and the glycine at position 569 is substituted with tryptophan (V488K_G569W), a modified enzyme in which the valine at position 488 is substituted with lysine and the arginine at position 572 is substituted with lysine (V488K_R572K), a modified enzyme in which the valine at position 488 is substituted with lysine and the threonine at position 573 is substituted with lysine (V488K_T573K), a modified enzyme in which the valine at position 488 is substituted with lysine and the threonine at position 573 is substituted with tryptophan (V488K_T573W), a modified enzyme in which the valine at position 488 is substituted with lysine and the tyrosine at position 516 is substituted with lysine (V488K_Y516K), a modified enzyme in which the valine at position 488 is substituted with lysine and the tyrosine at position 516 is substituted with tryptophan (V488K_Y516W), a modified enzyme in which the valine at position 488 is substituted with tryptophan and the asparagine at position 514 is substituted with tryptophan (V488W_N514W), a modified enzyme in which the valine at position 488 is substituted with tryptophan and the threonine at position 573 is substituted with tryptophan (V488W_T573W), a modified enzyme in which the glutamic acid at position 500 is substituted with alanine and the isoleucine at position 501 is substituted with alanine (E500A_I501A), a modified enzyme in which the serine at position 512 is substituted with valine and the asparagine at position 550 is substituted with serine (S512V_N550S), a modified enzyme in which the threonine at position 533 is substituted with glutamic acid and the asparagine at position 550 is substituted with serine (T533E_N550S), a modified enzyme in which the threonine at position 533 is substituted with glutamic acid and the tyrosine at position 615 is substituted with glycine (T533E_Y615G), a modified enzyme in which the tryptophan at position 570 is substituted with tyrosine and the tyrosine at position 615 is substituted with leucine (W570Y_Y615L) (these modified enzymes meet the above-described condition 3 that "a variant enzyme produces oligosaccharides in which the content of trisaccharides and higher saccharides is approximately equal and the content of tetrasaccharides is smaller, relative to the case of the parent wild-type enzyme"); a modified enzyme in which the phenylalanine at position 91 is substituted with valine and the glutamic acid at position 513 is substituted with glycine (F91V_E513G), a modified enzyme in which the threonine at position 180 is substituted with valine and the threonine at position 483 is substituted with lysine (T180V_T483K), a modified enzyme in which the threonine at position 180 is substituted with valine and the tyrosine at position 598 is substituted with asparagine (T180V_Y598N), a modified enzyme in which the threonine at position 180 is substituted with valine and the tyrosine at position 615 is substituted with glycine (T180V_Y615G), a modified enzyme in which the proline at position 182 is substituted with leucine and the tyrosine at position 615 is substituted with leucine (P182L_Y615L), a modified enzyme in which the arginine at position 376 is substituted with proline and the tyrosine at position 598 is substituted with asparagine (R376P_Y598N), a modified enzyme in which the glutamine at position 407 is substituted with leucine and the threonine at position 483 is substituted with lysine (Q407L_T483K), a modified enzyme in which the glutamine at position 407 is substituted with leucine and the lysine at position 487 is substituted with proline (Q407L_K487P), a modified enzyme in which the glutamine at position 407 is substituted with leucine and the tyrosine at position 615 is substituted with glycine (Q407L_Y615G), a modified enzyme in which the tyrosine at position 449 is substituted with glutamic acid and the lysine at position 487 is substituted with alanine (Y449E_K487A), a modified enzyme in which the tyrosine at position 449 is substituted with glutamic acid and the lysine at position 487 is substituted with proline (Y449E_K487P), a modified enzyme in which the threonine at position 483 is substituted with glycine and the lysine at position 487 is substituted with alanine (T483G_K487A), a modified enzyme in which the threonine at position 483 is substituted with glycine and the threonine at position 533 is substituted with glutamic acid (T483G_T533E), a modified enzyme in which the threonine at position 483 is substituted with glycine and the tyrosine at position 615 is substituted with glycine (T483G_Y615G), a modified enzyme in which the threonine at position 483 is substituted with methionine and the lysine at position 487 is substituted with alanine (T483M_K487A), a modified enzyme in which the threonine at position 483 is substituted with methionine and the lysine at position 487 is substituted with glycine (T483M_K487G), a modified enzyme in which the threonine at position 483 is substituted with methionine and the lysine at position 487 is substituted with proline (T483M_K487P), a modified enzyme in which the arginine at position 484 is substituted with histidine and the lysine at position 487 is substituted with aspartic acid (R484H_K487D), a modified enzyme in which the arginine at position 484 is substituted with lysine and the glutamic acid at position 513 is substituted with tryptophan (R484K_E513W), a modified enzyme in which the arginine at position 484 is substituted with lysine and the asparagine at position 514 is substituted with lysine (R484K_N514K), a modified enzyme in which the arginine at position 484 is substituted with lysine and the asparagine at position 514 is substituted with tryptophan (R484K_N514W), a modified enzyme in which the arginine at position 484 is substituted with lysine and the asparagine at position 515 is substituted with lysine (R484K_N515K), a modified enzyme in which the arginine at position 484 is substituted with lysine and the asparagine at position 515 is substituted with tryptophan (R484K_N515W), a modified enzyme in which the arginine at position 484 is substituted with lysine and the aspartic acid at position 517 is substituted with tryptophan (R484K_D517W), a modified enzyme in which the arginine at position 484 is substituted with lysine and the glycine at position 569 is substituted with lysine (R484K_G569K), a modified enzyme in which the arginine at position 484 is substituted with lysine and the glycine at position 571 is substituted with lysine (R484K_G571K), a modified enzyme in which the arginine at position 484 is substituted with lysine and the arginine at position 572 is substituted with lysine (R484K_R572K), a modified enzyme in which the arginine at position 484 is substituted with lysine and the arginine at position 572 is substituted with tryptophan (R484K_R572W), a modified enzyme in which the arginine at position 484 is substituted with lysine and the threonine at position 573 is substituted with lysine (R484K_T573K), a modified enzyme in which the arginine at position 484 is substituted with lysine and the threonine at position 573 is substituted with tryptophan (R484K_T573W), a modified enzyme in which the arginine at position 484 is substituted with lysine and the tyrosine at position 516 is substituted with lysine (R484K_Y516K), a modified enzyme in which the arginine at position 484 is substituted with tryptophan and the asparagine at position 515 is substituted with lysine (R484W_N515K), a modified enzyme in which the glycine at position 485 is substituted with aspartic acid and the lysine at position 487 is substituted with histidine (G485D_K487H), a modified enzyme in which the glycine at position 485 is substituted with lysine and the lysine at position 487 is substituted with histidine (G485K_K487H), a modified enzyme in which the glycine at position 485 is substituted with lysine and the glycine at position 569 is substituted with lysine (G485K_G569K), a modified enzyme in which the glycine at position 485 is substituted with lysine and the asparagine at position 514 is substituted with lysine (G485K_N514K), a modified enzyme in which the glycine at position 485 is substituted with lysine and the asparagine at position 515 is substituted with lysine (G485K_N515K), a modified enzyme in which the glycine at position 485 is substituted with lysine and the asparagine at position 515 is substituted with tryptophan (G485K_N515W), a modified enzyme in which the glycine at position 485 is substituted with arginine and the lysine at position 487 is substituted with aspartic acid (G485R_K487D), a modified enzyme in which the glycine at position 485 is substituted with tryptophan and the glutamic acid at position 513 is substituted with tryptophan (G485W_E513W), a modified enzyme in which the glycine at position 485 is substituted with tryptophan and the asparagine at position 515 is substituted with lysine (G485W_N515K), a modified enzyme in which the glycine at position 485 is substituted with tryptophan and the asparagine at position 515 is substituted with tryptophan (G485W_N515W), a modified enzyme in which the lysine at position 487 is substituted with alanine and the serine at position 531 is substituted with alanine (K487A_S531A), a modified enzyme in which the lysine at position 487 is substituted with alanine and the tryptophan at position 593 is substituted with phenylalanine (K487A_W593F), a modified enzyme in which the lysine at position 487 is substituted with alanine and the tyrosine at position 615 is substituted with leucine (K487A_Y615L), a modified enzyme in which the lysine at position 487 is substituted with tryptophan and the asparagine at position 514 is substituted with lysine (K487W_N514K), a modified enzyme in which the lysine at position 487 is substituted with tryptophan and the asparagine at position 514 is substituted with tryptophan (K487W_N514W), a modified enzyme in which the lysine at position 487 is substituted with tryptophan and the tyrosine at position 516 is substituted with tryptophan (K487W_Y516W), a modified enzyme in which the lysine at position 487 is substituted with tryptophan and the glycine at position 569 is substituted with lysine (K487W_G569K), a modified enzyme in which the lysine at position 487 is substituted with tyrosine and the asparagine at position 515 is substituted with phenylalanine (K487Y_N515F), a modified enzyme in which the lysine at position 487 is substituted with tyrosine and the asparagine at position 515 is substituted with tryptophan (K487Y_N515W), a modified enzyme in which the valine at position 488 is substituted with lysine and the asparagine at position 515 is substituted with lysine (V488K_N515K), a modified enzyme in which the valine at position 488 is substituted with lysine and the asparagine at position 515 is substituted with tryptophan (V488K_N515W), a modified enzyme in which the valine at position 488 is substituted with tryptophan and the asparagine at position 515 is substituted with lysine (V488W_N515K), a modified enzyme in which the valine at position 488 is substituted with tryptophan and the asparagine at position 515 is substituted with tryptophan (V488W_N515W), a modified enzyme in which the valine at position 488 is substituted with tyrosine and the asparagine at position 515 is substituted with tryptophan (V488Y_N515W), a modified enzyme in which the asparagine at position 550 is substituted with serine and the tyrosine at position 598 is substituted with asparagine (N550S_Y598N), a modified enzyme in which the asparagine at position 550 is substituted with serine and the tyrosine at position 615 is substituted with glycine (N550S_Y615G), a modified enzyme in which the asparagine at position 550 is substituted with serine and the tyrosine at position 615 is substituted with leucine (N550S_Y615L), a modified enzyme in which the asparagine at position 550 is substituted with serine and the tyrosine at position 615 is substituted with proline (N550S_Y615P) (these modified enzymes meet the above-described condition 4 that "a variant enzyme produces oligosaccharides in which the content of trisaccharides and higher saccharides is approximately equal and the content of tetrasaccharides is higher, relative to the case of the parent wild-type enzyme").

These specific examples represent modified enzymes in which two amino acids are substituted. On the other hand, examples of modified enzymes in which three or four amino acids are substituted can include a modified enzyme in which the arginine at position 484 is substituted with alanine, the glycine at position 485 is substituted with alanine, and the lysine at position 487 is substituted with aspartic acid (R484A_G485A_K487D), a modified enzyme in which the arginine at position 484 is substituted with aspartic acid, the glycine at position 485 is substituted with aspartic acid, and the lysine at position 487 is substituted with aspartic acid (R484D_G485D_K487D), a modified enzyme in which the glycine at position 485 is substituted with arginine, the aspartic acid at position 486 is substituted with arginine, and the lysine at position 487 is substituted with arginine (G485R_D486R_K487R), a modified enzyme in which the arginine at position 484 is substituted with alanine, the glycine at position 485 is substituted with alanine, the aspartic acid at position 486 is substituted with alanine, and the lysine at position 487 is substituted with alanine (R484A_G485A_D486A_K487A), a modified enzyme in which the arginine at position 484 is substituted with alanine, the glycine at position 485 is substituted with alanine, the aspartic acid at position 486 is substituted with proline, and the lysine at position 487 is substituted with proline (R484A_G485A_D486P_K487P) (these modified enzymes meet the above-described condition 3 that "a variant enzyme produces oligosaccharides in which the content of trisaccharides and higher saccharides is approximately equal and the content of tetrasaccharides is smaller, relative to the case of the parent wild-type enzyme"); a modified enzyme in which the arginine at position 484 is substituted with alanine, the glycine at position 485 is substituted with alanine, and the lysine at position 487 is substituted with aspartic acid (R484A_G485A_K487D), a modified enzyme in which the arginine at position 484 is substituted with cysteine, the aspartic acid at position 486 is substituted with histidine, and the lysine at position 487 is substituted with arginine (R484C_D486H_K487R), a modified enzyme in which the glycine at position 485 is substituted with arginine, the aspartic acid at position 486 is substituted with tryptophan, and the lysine at position 487 is substituted with tryptophan (G485R_D486W_K487W), a modified enzyme in which the glycine at position 485 is substituted with arginine, the aspartic acid at position 486 is substituted with alanine, and the lysine at position 487 is substituted with alanine (G485R_D486A_K487A), a modified enzyme in which the glycine at position 485 is substituted with arginine, the aspartic acid at position 486 is substituted with proline, and the lysine at position 487 is substituted with proline (G485R_D486P_K487P), a modified enzyme in which the arginine at position 484 is substituted with alanine, the glycine at position 485 is substituted with alanine, the aspartic acid at position 486 is substituted with alanine, and the lysine at position 487 is substituted with alanine (R484A_G485A_D486A_K487A), a modified enzyme in which the arginine at position 484 is substituted with alanine, the glycine at position 485 is substituted with alanine, the aspartic acid at position 486 is substituted with arginine, and the lysine at position 487 is substituted with arginine (R484A_G485A_D486R_K487R), a modified enzyme in which the arginine at position 484 is substituted with aspartic acid, the glycine at position 485 is substituted with aspartic acid, the aspartic acid at position 486 is substituted with arginine, and the lysine at position 487 is substituted with arginine (R484D_G485D_D486R_K487R), a modified enzyme in which the arginine at position 484 is substituted with aspartic acid, the glycine at position 485 is substituted with aspartic acid, the aspartic acid at position 486 is substituted with proline, and the lysine at position 487 is substituted with proline (R484D_G485D_D486P_K487P), a modified enzyme in which the arginine at position 484 is substituted with aspartic acid, the glycine at position 485 is substituted with aspartic acid, the aspartic acid at position 486 is substituted with alanine, and the lysine at position 487 is substituted with alanine (R484D_G485D_D486A_K487A), a modified enzyme in which the arginine at position 484 is substituted with aspartic acid, the glycine at position 485 is substituted with aspartic acid, the aspartic acid at position 486 is substituted with tryptophan, and the lysine at position 487 is substituted with tryptophan (R484D_G485D_D486W_K487W), a modified enzyme in which the arginine at position 484 is substituted with proline, the glycine at position 485 is substituted with proline, the aspartic acid at position 486 is substituted with proline, and the lysine at position 487 is substituted with arginine (R484P_G485P_D486R_K487R) (these modified enzymes meet the above-described condition 4 that "a variant enzyme produces oligosaccharides in which the content of trisaccharides and higher saccharides is approximately equal and the content of tetrasaccharides is higher, relative to the case of the parent wild-type enzyme").

The modified enzymes that have been described above are obtained by substituting a particular amino acid(s) of a reference β-galactosidase with other amino acid(s). Through the inventors' studies, there have been found, as useful modified enzymes other than variants with the above-described amino acid substitutions, modified enzymes in which an amino acid(s) is/are inserted at a particular position(s) in a given amino acid sequence (insertion variants), a particular amino acid(s) in a given amino acid sequence is/are deleted (deletion variants), and in addition, an amino acid substitution is applied to a deletion variant. Therefore, one embodiment of the present invention provides a modified enzyme which undergone any of the following modifications in a β-galactosidase consisting of the amino acid sequence of any of SEQ ID NOs. 1 to 4 or an amino acid sequence having 90% or more identity to the amino acid sequence set forth in any of SEQ ID NOs. 1 to 4:

(a) a deletion of the region of arginine at position 484 (R484) to lysine at position 487 (K487) or a region corresponding thereto;

(b) an insertion of an amino acid(s) at the position between asparagine at position 514 (N514) and asparagine at position 515 (N515) or at a position corresponding thereto;

(c) an insertion of an amino acid(s) at the position between proline at position 604 (P604) and tyrosine at position 605 (Y605) or at a position corresponding thereto;

(d) a deletion of the glycine at position 485 (G485) or an amino acid corresponding thereto, and in addition, a substitution of aspartic acid at position 486 (D486) or an amino acid corresponding thereto;

(e) a deletion of the region of glycine at position 485 (G485) to aspartic acid at position 486 (D486) or a region corresponding thereto, and in addition, a substitution of lysine at position 487 (K487) or an amino acid corresponding thereto;

(f) a deletion of the region of glycine at position 485 (G485) to aspartic acid at position 486 (D486) or a region corresponding thereto, and in addition, a substitution of arginine at position 484 (R484) or an amino acid corresponding thereto, and a substitution of lysine at position 487 (K487) or an amino acid corresponding thereto;

(g) an insertion of an amino acid(s) at the position between arginine at position 484 (R484) and glycine at position 485 (G485) or at a position corresponding thereto; and (h) an insertion of an amino acid(s) at the position between glycine at position 485 (G485) and aspartic acid at position 486 (D486) or at a position corresponding thereto.

For (d) to (f), it is preferable that the amino acid that has been substituted for R484 is tryptophan or proline; for D486, histidine; and for K487, arginine, tryptophan, or proline. For (b), (c), (g), and (h), the number of amino acids to be inserted is, for example, from 1 to 10, preferably from 2 to 8. In the following are described specific examples of the above-described (a) to (g), along with their notation.

<Notation for Modified Enzymes>

"N514-F-F-N515" refers to a modified enzyme having two F (phenylalanine) residues inserted between N514 and N515.

"Δ484-487" refers to a modified enzyme having a deletion of the amino acids at positions 484 to 487.

"Δ485-486_K487R" refers to a modified enzyme having both a deletion of the amino acids at positions 485 to 486 and a substitution of the amino acid at position 487 with R (arginine).

<Specific Examples of Modified Enzymes>

(A) Modified enzymes meeting the above-described condition 3 that "a variant enzyme produces oligosaccharides in which the content of trisaccharides and higher saccharides is approximately equal and the content of tetrasaccharides is smaller, relative to the case of the parent wild-type enzyme," which are represent by Δ484-487,
N514-F-F-N515,
N514-W-W-N515,
P604-W-W-Y605,
P604-A-A-A-A-Y605, and
P604-F-F-F-F-Y605.

(B) Modified enzymes meeting the above-described condition 4 that "a variant enzyme produces oligosaccharides in which the content of trisaccharides and higher saccharides is approximately equal and the content of tetrasaccharides is higher, relative to the case of the parent wild-type enzyme," which are represent by

Δ485 D486H,
Δ485-486_K487R,
Δ485-486_R484W_K487W,

Δ485-486_R484W_K487P,
R484-A-A-G485,
R484-F-F-G485,
R484-K-K-G485,
R484-P-P-G485,
R484-R-R-G485,
R484-S-S-G485,
R484-W-W-G485,
G485-S-S-S-D486,
R484-A-A-A-A-G485,
R484-D-D-D-D-G485,
R484-F-F-F-F-G485,
R484-P-P-P-P-G485,
R484-R-R-R-R-G485,
R484-S-S-S-S-G485,
R484-W-W-W-W-G485,
R484-A-A-A-A-A-A-A-A-G485,
R484-D-D-D-D-D-D-D-D-G485,
R484-F-F-F-F-F-F-F-F-G485,
R484-K-K-K-K-K-K-K-K-G485, and
R484-P-P-P-P-P-P-P-G485.

As shown in the examples described below, other amino acid residues useful for alteration of the enzyme specificity were also found by an approach different from those by which the amino acids of groups 1 to 6 were identified. On the basis of the results from this approach, the present invention further provides the following modified β-galactosidase enzyme: a modified β-galactosidase in which, in addition to a substitution as described above, the tryptophan at position 1540 (W1540) is substituted with other amino acid in a β-galactosidase consisting of the amino acid sequence of SEQ ID NO. 1. The amino acid that has been substituted for the tryptophan preferably is alanine, cysteine, aspartic acid, glutamic acid, phenylalanine, glycine, histidine, isoleucine, lysine, leucine, methionine, asparagine, proline, glutamine, arginine, serine, threonine, or valine. Modified enzymes in this embodiment are highly useful in that, in addition to the modified enzyme having properties arising from an above-described substitution employed in combination, its use results in an increase in the content of tetrasaccharides.

From the results of further studies, as amino acids that are a target for substitution and that are highly useful in that the content of tetrasaccharides is increased in the case of a β-galactosidase consisting of the amino acid sequence of SEQ ID NO. 1, there were identified lysine at position 487 (K487), asparagine at position 514 (N514), and asparagine at position 515 (N515). The amino acids that have been substituted for the above-mentioned amino acids are preferably as indicated below.

The amino acid that has been substituted for lysine at position 487 (K487) is glycine or proline.

The amino acid that has been substituted for asparagine at position 514 (N514) is tryptophan.

The amino acid that has been substituted for asparagine at position 515 (N515) is lysine or tryptophan.

Besides, one of the β-galactosidases derived from *Bacillus circulans* is described in WO 2010/098561. It is also possible that a mutation corresponding to any of the amino acid substitutions disclosed in the present specification is applied to this β-galactosidase, thereby to obtain a modified β-galactosidase. The sequence coding β-galactosidase disclosed in WO 2010/098561 has about 70% identity to the sequence coding a reference β-galactosidase in the present application (SEQ ID NO. 5).

(Nucleic Acid Coding for Modified β-Galactosidase, Etc.)

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further mutant of an enzyme.

The "gene coding for a modified enzyme" herein refers to a nucleic acid capable of obtaining the modified enzyme when it is expressed, and includes, as a matter of course of a nucleic acid having a nucleotide sequence corresponding to the amino acid sequence of the modified enzyme, also a nucleic acid obtained by adding a sequence that does not code for an amino acid sequence to such a nucleic acid. Degeneracy of a codon is also considered.

The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a nucleotide sequence in a part (hereinafter also referred to as a "homologous nucleic acid", and a nucleotide sequence defining a homologous nucleic acid is also referred to as a "homologous nucleotide sequence") as compared to the nucleotide sequence of the gene coding for the modified enzyme of the invention, although functions of a protein coded by the nucleic acid are equal. An example of the homologous nucleic acid includes a DNA composed of a nucleotide sequence containing substitution, deletion, insertion, addition or inversion of 1 to several nucleotides on the basis of the nucleotide sequence of the nucleic acid coding for the modified enzyme of the present invention and coding for a protein having enzyme activity characteristic to the modified enzyme. Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having the complementary nucleotide sequence to the nucleotide sequence of the gene coding for the modified enzyme of the invention. Another embodiment of the present invention provides a nucleic acid having a nucleotide sequence with an identity of at least about 60%, 70%, 80%, 90%, 95%, 99%, or 99.9% to the nucleotide sequence of the gene coding for the modified enzyme of the invention or the complementary nucleotide sequence Another embodiment of the present invention relates to a nucleic acid having a nucleotide sequence hybridizing to the complementary nucleotide sequence to the nucleotide sequence of the gene coding for the modified enzyme of the invention or its homologous nucleotide sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 µg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of modified salmon sperm DNA, and a 50 mM phosphate buffer (pH 7.5) as a hybridization liquid.

Another embodiment of the present invention provides a nucleic acid (nucleic acid fragment) having a part of the nucleotide sequence of the gene coding for the modified enzyme of the invention or the complementary nucleotide sequence. Such a nucleic acid fragment can be used in detection, identification, and/or amplification of a nucleic acid having the nucleotide sequence of the gene coding for the modified enzyme of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the nucleotide sequence of the gene coding for the modified enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a modified enzyme can be used. Examples of *Escherichia coli* include *Escherichia coli* BL21 (DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Felgner, P. L. et al., Proc. Natl. Acad. Sci. U.S.A. 84, 7413-7417 (1984)). Note that the microorganism of the present invention can be used in producing the modified enzyme of the present invention.

(Enzyme Agent Containing Modified β-Galactosidase)

The modified enzyme of the present invention is provided, for example, in the form of an enzyme agent. The enzyme agent may contain an excipient, a buffer agent, a suspending agent, a stabilizer, a preservative, an antiseptic, saline and the like besides the active ingredient (the modified enzyme of the present invention). As the excipient, starch, dextrin, maltose, trehalose, lactose, D-glucose, sorbitol, D-mannitol, white soft sugar, glycerol and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, ethanol, benzalkonium chloride, paraoxybenzoic acid, chlorobutanol and the like can be used.

(Applications of Modified β-Galactosidases)

A further aspect of the present invention provides applications of modified enzymes or enzyme preparations. Examples of these applications include use for production of galacto-oligosaccharides, production and processing of pharmaceutical products and supplements for lactose-intolerant patients, production and processing of dairy products (for example, processed milk products such as lactose-reduced milk, powdered milk such as skim milk and nursing powdered milk, yogurts, and others), and production and processing of medical foods.

Modified enzymes of the present invention are particularly useful for the production of galacto-oligosaccharides. In the production of galacto-oligosaccharides, a predetermined amount (for example, 50 U to 1000 U) of a modified enzyme is added, for example, to a pre-heated lactose-dissolved solution (for example, 30% to 50% lactose, pH 7.0) and the mixture is left standing at around 40° C. for 1 to 10 hours, to yield galacto-oligosaccharides. Galacto-oligosaccharides are represented by the formula Gal-(Gal)n-Glc, wherein n is from 0 to about 5; and Gal is a galactose residue and Glc is a glucose residue. The manner in which Gal and Glc residues are bound includes not only β1-6, β1-3, β1-4, β1-2, but also α1-3, α1-6, and others.

The use of a plurality of modified enzymes with different properties would make it possible that various galacto-oligosaccharides are produced separately as intended. This form of usage is effective in reproducing the profile of galacto-oligosaccharides (the type and ratio of galacto-oligosaccharides) contained in mother's milk.

A modified enzyme and the parent wild-type enzyme thereof are different in their properties. Therefore, the use of a modified enzyme and the parent wild-type enzyme thereof in combination makes it possible to manufacture a galacto-oligosaccharide of which the production cannot be achieved (or is not suitable) by using the wild-type enzyme alone. When a plurality of modified enzymes with different properties and the parent wild-type enzyme thereof are used in combination, it would be possible to further increase the kind of galacto-oligosaccharides to be produced. Thus, the use of (one or more) modified enzymes and the parent wild-type enzyme thereof in combination is also effective in producing various galacto-oligosaccharides separately as intended.

Methods by which galacto-oligosaccharides (a mixture of various types of galacto-oligosaccharides) are obtained using a plurality of modified enzymes (a combination of a plurality of modified enzymes, or alternatively a combination of a given wild-type enzyme and one or more modified enzymes thereof) include, when classified roughly, one in which galacto-oligosaccharides that have been produced using respective enzymes are mixed, one in which a plurality of enzymes is allowed to act on a raw material (lactose) at the same time, and one in which a plurality of enzymes is allowed to act on a raw material in a stepwise manner.

EXAMPLES

<Identification of Positions for Effective Mutations 1>

1. Purposes

A *Bacillus circulans*-derived β-galactosidase is an important enzyme for the industrial production of galacto-oligosaccharides. However, the galacto-oligosaccharides produced by using the enzyme are highly uniform in composition, and it is difficult that the composition (profile) of the galacto-oligosaccharides to be produced is altered even though the conditions under which they are produced are adjusted. In the past, it has been difficult to obtain the steric structure information of this enzyme, so that it has not been easy to identify amino acids responsible for its functions. For this reason, the inventors attempted to identify positions for effective mutations by means of using computer simulation, aiming at creating a modified enzyme useful for the production of galacto-oligosaccharides.

2. Methods and Results (1) Prediction of the Steric Structure of Wild-Type Enzymes and Design of Variant Enzymes (Modified β-Galactosidases)
(1-1) Prediction of the Steric Structure and Design of Mutation Sites on the Basis of the Primary Sequences of the Wild-Type Enzymes β-galactosidase derived from *Bacillus circulans* performs the hydrolysis of lactose and catalyze the trans-galactosylation reaction (production of galacto-oligosaccharides). From earlier studies, it is known that the β-galactosidase produced by *Bacillus circulans* is made up of four enzymes (isozymes) with different molecular weights, that is, β-galactosidase isozymes with a molecular weight of 195 kD (BgaD-A; SEQ ID NO. 1), 160 kD (BgaD-B; SEQ ID NO. 2), 135 kD (BgaD-C; SEQ ID NO. 3), and 86 kD (BgaD-D; SEQ ID NO. 4) (Patent Literature 1 and Non Patent Literature 1). Among these enzymes, BgaD-D with the lowest molecular weight is a β-galactosidase isozyme of the smallest size possessing enzymatic activity, and has the highest transglycosylation activity.

As described above, it has been difficult to obtain the steric structure information of β-galactosidase isozymes derived from *Bacillus circulans*. For this reason, the inventors attempted to predict their steric structures using computer simulation. Information on the steric structure of enzymes with β-galactosidase activity was extracted from the steric structures information deposited in a database (Protein Data Bank (http://www.pdb.org/)), thereby to search for enzymes having a sequence homologous to the primary sequence of any of the β-galactosidase isozymes derived from *Bacillus circulans*. Specifically, the primary sequence of a β-galactosidase isozyme derived from *Bacillus circulans* was used as a reference sequence to search for steric structures that are predicted to be highly homologous relative to the β-galactosidase isozyme. In consequence, there was found the structure 3GM8 (a beta-glycosidase from *Bacteroides vulgatus*) (FIG. 1). Subsequently, loop sequences located around the active center were identified based on a steric structure modeled using the 3GM8 as a template. By using the steric structure model thus constructed, amino acids that are likely to come into contact with the substrate were predicted from among the amino acids forming the substrate pocket of a β-galactosidase derived from *Bacillus circulans*. Furthermore, sites for introduction of mutation were designed, taking note of amino acids on the loops.

(1-2) Construction of Plasmids and Generation of Variants

Figure 2:
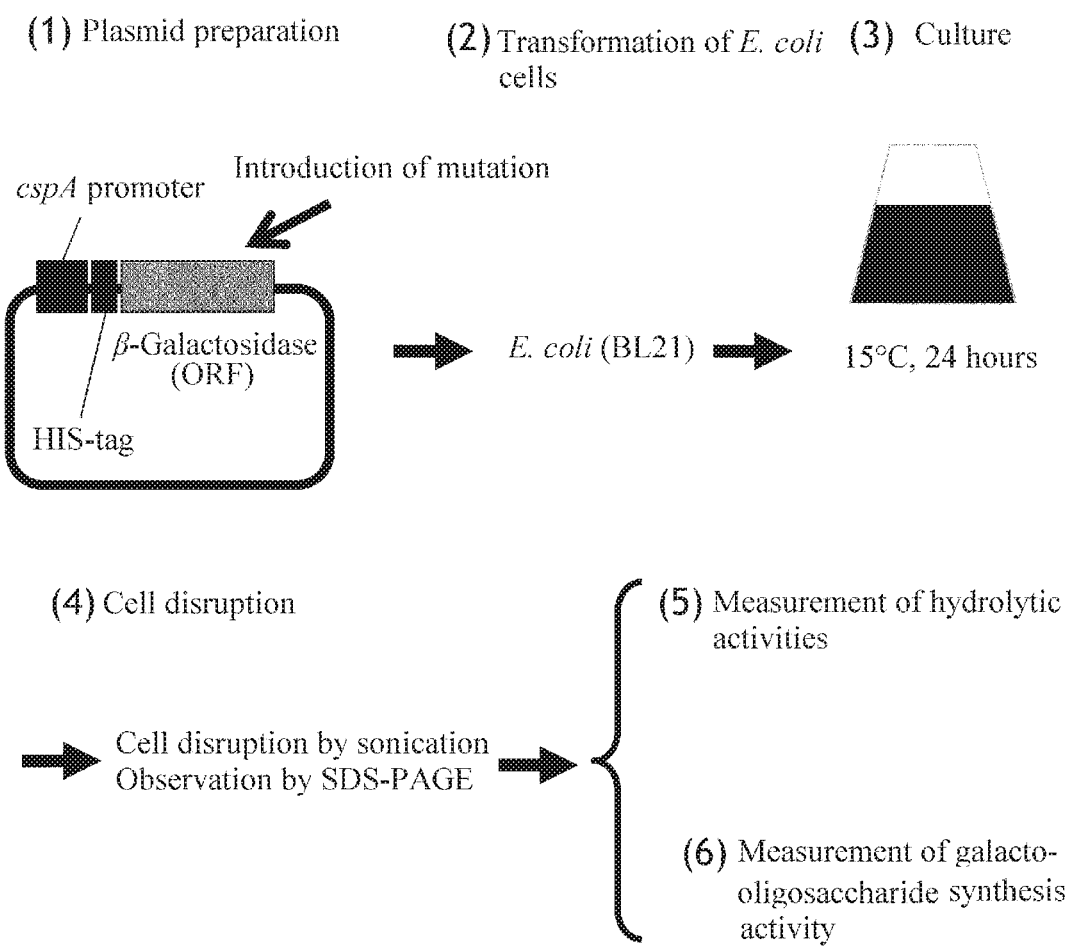
FIG. 2 shows a system for recombinant expression of variants (modified β-galactosidases).

Amino acids at the sites where a mutation was to be introduced were intended to be subjected to random substitution. The actual introduction of mutations was performed via PCR using as a template a plasmid coding a DNA for BgaD type D. At a single site where a mutation was to be introduced, 8 to 19 amino acids to be substituted for the original amino acid were designed and used for actual mutations. Primers corresponding to the respective mutations were designed, and the respective mutations were introduced via an inverted PCR method using a KOD plus Mutagenesis kit (Toyobo Co., Ltd,). A PCR product was self-ligated according to the protocol for the kit, and then transformed into *E. coli* DH5alpha cells. The plasmid was obtained by a mini-prep procedure and then sequenced to verify the mutation. In addition, the plasmid was used to transform into *E. coli* BL21 cells, which then were subjected to expression of the protein (variant) according to the protocol described below (FIG. 2).

<Protocol>

1. Pre-culture in 1.5 mL of LB with amp (37° C., overnight)
2. Add 0.06 mL of the pre-culture to 3 mL of LB with amp
3. Incubate at 37° C. for 4 hours
4. Transfer the test tube on ice and add 0.75 pt of 1 M IPTG
5. Incubate at 15° C. for 24 hours
6. Harvest and wash cells with phosphate buffer (pH 7.4)
7. Suspend the cells in 0.25 mL phosphate buffer (pH 7.4)
8. Subject the cells to ultrasonic disruption in a sonicator (30 seconds×3 times)
9. Collect the supernatant by centrifugation The crude *E. coli* cells extract prepared by the above procedure was used as a sample of the variant (modified β-galactosidase).

Further, variants were subjected to purification for verification of their activities. Each of the variants, which had been expressed as a fusion protein having a HIS tag attached at the N terminus, was purified on a nickel column HISTrap HP (1 ml; GE Healthcare). The buffers used for the respective operations were as follows:

A binding buffer (20 mM sodium phosphate, 0.2 M NaCl, 20 mM imidazole, pH 7.4)

An elution buffer (10 mM sodium phosphate, 0.1 M NaCl, 0.25 M imidazole, pH 7.4)

The variant was allowed to be bound on the column in the binding buffer, and then the column was washed with the same buffer. After that, the bound variant was eluted from the column in the elution buffer. The elution fractions were used as samples for SDS-PAGE and for measurements of hydrolytic activities, to ascertain the degree of purification of the enzyme.

(1-3) Evaluation of Hydrolytic Activities

Measurement methods for hydrolysis were carried out with reference to a previous document (Patent Literature 1). As substrate, use was made of three substances, o-nitrophenyl-β-D-galactopyranoside (ONPG), lactose, and allolactose, for which the respective activities were measured by the methods described below.

(a) LSU Activity: ONPG Method

When lactase acts on ONPG (at a final concentration of 20 mM) at pH 6.0 and 40° C., the amount of enzyme at which 1 μmol of ONPG is generated per minute in an early stage of the reaction is defined as 1 LSU.

(b) LU Activity: Lactose Decomposition Assay

When lactase acts on lactose (at a final concentration of 10%) at pH 6.0 and 40° C., the amount of enzyme at which 1 μmol of glucose is generated per minute in an early stage of the reaction is defined as 1 LU.

(c) Allolactose Decomposing Activity: Allolactose Decomposition Assay

When lactase acts on allolactose (at a final concentration of 1%) at pH 6.0 and 40° C., the amount of enzyme at which 1 μmol of glucose is generated per minute in an early stage of the reaction is defined as 1 U.

(d) 1%-Lactose Decomposing Activity: Lactose Decomposition Assay

When lactase acts on lactose (at a final concentration of 1%) at pH 6.0 and 40° C., the amount of enzyme at which 1 μmol of glucose is generated per minute in an early stage of the reaction is defined as 1 U.

By these measurements, mutation sites were sought out which caused a change in the substrate specificity, as compared to that of the parent wild-type enzyme.

(1-4) Evaluation of Galacto-Oligosaccharide (GOS) Synthesis Activity

For the evaluation of galacto-oligosaccharide (GOS) synthesis activity, an oligosaccharide synthesis reaction was carried out using a concentrated solution of lactose as the substrate, and reaction products were analyzed by HPLC. From earlier studies, it has been reported that when lactose is used as the substrate, a high-yield GOS synthesis can be done by carrying out the enzyme reaction at a final substrate concentration of about 50% and a pH of around 6 (JP H11-18763 A). The GOS synthesis was performed according to the method described in the report (the method described in Example 2). The composition of GOSs produced was analyzed using the following columns:

A gel filtration column: MCIGEL CK04S (Mitsubishi Kasei Corp.)

An amide column: NH2P-40 3E (Showa Denko K.K.)

On the basis of the analysis results, the contents of oligosaccharides for tetrasaccharides and for trisaccharides and higher saccharides, and of allolactose in the entire saccharides were determined to prepare tables.

(2) Mutation Sites Resulting in a Decreased or Increased Hydrolytic Activity for Allolactose The LSU activity, LU activity, allolactose-decomposing activity, and 1%-lactose decomposing activity were determined for recombinantly expressed enzymes of all variant enzymes and the parent wild-type enzymes thereof. First, from the results of measurements of the LSU activity and LU activity, variants with which the disappearance of enzymatic activity was observed were excluded. On the other hand, the allolactose decomposing activity varies depending upon the lactose decomposing activity, and thus values of "allolactose decomposing activity÷1%-lactose decomposing activity" were used to evaluate relative substrate specificities of variant enzymes for allolactose, which were compared to that of the parent wild-type enzyme.

From the results of actual measurements, the parent wild-type enzyme was found to have a value of "allolactose decomposing activity÷1%-lactose decomposing activity" of 0.02%. On the basis of this observation, variants meeting either of the conditions described below were selected as variants having altered substrate specificity for allolactose (FIG. 3).

Condition 1: a variant enzyme has an allolactose decomposing activity of 50% or less relative to that of the parent wild-type enzyme, which means that the value of "allolactose decomposing activity÷ 1%-lactose decomposing activity" for a variant enzyme is not more than ½ of that for the parent wild-type enzyme.

Condition 2: a variant enzyme has an allolactose decomposing activity of 150% or more relative to that of the parent wild-type enzyme, which means that the value of "allolactose decomposing activity÷ 1%-lactose decomposing activity" for a variant enzyme is not less than 3/2 of that for the parent wild-type enzyme.

The variants meeting condition 1 were the following 28 variant enzymes (FIG. 3(A)), in which the tyrosine at position 449 (Y449) was substituted with any of amino acids D, E, N, and W;

the serine at position 531 (S531) was substituted with any of amino acids A, D, E, F, G, I, M, N, and Q;

the tryptophan at position 593 (W593) was substituted with an amino acid F;

the proline at position 602 (P602) was substituted with any of amino acids E and G;

the proline at position 604 (P604) was substituted with any of amino acids A, G, H, I, M, S, T, V, W, and Y; and the lysine at position 612 (K612) was substituted with an amino acid M.

The variants meeting condition 2 were the following 14 variant enzymes (FIG. 3(B)), in which the tyrosine at position 187 (Y187) was substituted with any of amino acids D, E, and G;

the serine at position 188 (S188) was substituted with any of amino acids P and T;

the threonine at position 533 (T533) was substituted with any of amino acids M and Q;

the proline at position 602 (P602) was substituted with any of amino acids C, I, N, S, T, and V; and the lysine at position 612 (K612) was substituted with an amino acid F.

From these results, it turned out that a total of 9 amino acids are related to the substrate specificity of the hydrolytic activity for allolactose.

(3) Mutation Sites Resulting in a Change in the Composition of Galacto-Oligosaccharides (GOSs)

Mutation sites resulting in a change in the composition of galacto-oligosaccharides (GOSs) were evaluated for recombinantly expressed enzymes of all variant enzymes and the parent wild-type enzyme thereof. Variants meeting either of the conditions described below were selected as variants resulting in an altered composition of GOSs. First, the composition of GOSs produced was analyzed, and attention was paid to the contents of oligosaccharide components, tetrasaccharides, and trisaccharides and higher saccharides, in the GOSs produced. From the results of actual measurements, the parent wild-type enzyme was found to have a content of tetrasaccharides of 10.8% and a content of trisaccharides and higher saccharides of 40.0%. On the basis of this observation, mutation sites were selected in which the resultant variant enzymes gave a content of trisaccharides that was close to the value provided by the wild-type enzyme (that is, an amount of oligosaccharides synthesized that was comparable to that synthesized by the wild-type enzyme), but resulted in an altered content of tetrasaccharides. Therefore, mutation sites were selected which meet either of the following conditions:

Condition 3: a variant enzyme produces oligosaccharides in which the content of trisaccharides and higher saccharides is approximately equal and the content of tetrasaccharides is smaller, relative to the case of the parent wild-type enzyme.

Condition 4: a variant enzyme produces oligosaccharides in which the content of trisaccharides and higher saccharides is approximately equal and the content of tetrasaccharides is higher, relative to the case of the parent wild-type enzyme.

The variants meeting condition 3 were the following 33 variant enzymes (FIG. 4(A)), in which the proline at position 182 (P182) was substituted with an amino acid L;

the tyrosine at position 187 (Y187) was substituted with any of amino acids D and L;

the serine at position 188 (S188) was substituted with an amino acid I;

the tryptophan at position 405 (W405) was substituted with any of amino acids A, D, E, G, H, L, N, S, and T;

the glutamine at position 407 (Q407) was substituted with any of amino acids G and R;

the tyrosine at position 449 (Y449) was substituted with any of amino acids E, I, Q, R, and S;

the threonine at position 483 (T483) was substituted with an amino acid Q;

the serine at position 512 (S512) was substituted with any of amino acids F, T and V;

the serine at position 531 (S531) was substituted with an amino acid P;

the asparagine at position 550 (N550) was substituted with any of amino acids L, R, and S;

the proline at position 602 (P602) was substituted with any of amino acids L, N, and Q; and the proline at position 604 (P604) was substituted with any of amino acid I and M.

The variants meeting condition 4 were the following 8 variant enzymes (FIG. 4(B)), in which the threonine at position 483 (T483) was substituted with any of amino acids K, M, and R;

the serine at position 512 (S512) was substituted with any of amino acids G and K;

the glutamine at position 551 (Q551) was substituted with an amino acid N;

the tyrosine at position 598 (Y598) was substituted with an amino acid N; and the tyrosine at position 615 (Y615) was substituted with an amino acid T.

From these results, it turned out that a total of 9 amino acids are related to the amount of production of tetrasaccharides.

Second, attention was paid to the contents of allolactose and of trisaccharides and higher saccharides in the composition of GOSs produced. The parent wild-type enzyme was found to have a content of allolactose of 3.58% and a content of trisaccharides and higher saccharides of 40.2%. On the basis of this observation, sites for mutation were sought in which the resultant variant enzymes gave a content of trisaccharides that was close to the value provided by the wild-type enzyme, but resulted in an altered content of allolactose. Therefore, mutation sites were selected which meet either of the following conditions:

Condition 5: a variant enzyme produces oligosaccharides in which the content of trisaccharides and higher saccharides is approximately equal and the content of allolactose is smaller, relative to the case of the parent wild-type enzyme.

Condition 6: a variant enzyme produces oligosaccharides in which the content of trisaccharides and higher saccharides is approximately equal and the content of allolactose is higher, relative to the case of the parent wild-type enzyme.

The variants meeting condition 5 were the following 14 variant enzymes (FIG. 5(A)), in which the tryptophan at position 405 (W405) was substituted with any of amino acids A, D, S, and T;

the threonine at position 483 (T483) was substituted with an amino acid M;

the serine at position 531 (S531) was substituted with any of amino acids D, F, G, L, K, and M;

the asparagine at position 550 (N550) was substituted with an amino acid F; and the tyrosine at position 598 (Y598) was substituted with any of amino acids F and H.

The variants meeting condition 6 were the following 45 variant enzymes (FIG. 5(B)), in which the proline at position 182 (P182) was substituted with any of amino acids L and S;

the tyrosine at position 187 (Y187) was substituted with any of amino acids D, E, and N;

the serine at position 188 (S188) was substituted with any of amino acids E, G, I, and N;

the tryptophan at position 405 (W405) was substituted with an amino acid H;

the alanine at position 406 (A406) was substituted with an amino acid P;

the glutamine at position 407 (Q407) was substituted with any of amino acids A, F, G, K and R;

the tyrosine at position 449 (Y449) was substituted with any of amino acids E and R;

the threonine at position 483 (T483) was substituted with any of amino acids S and Q;

the serine at position 512 (S512) was substituted with any of amino acids G, T and V;

the serine at position 534 (S534) was substituted with any of amino acids K and Q;

the asparagine at position 550 (N550) was substituted with any of amino acids A, G, K, L, M, R, and S;

the glutamine at position 551 (Q551) was substituted with any of amino acids K and H;

the proline at position 602 (P602) was substituted with any of amino acids C, D, and N;

the tyrosine at position 609 (Y609) was substituted with any of amino acids D, Q, and T;

the lysine at position 612 (K612) was substituted with any of amino acids F and I; and the tyrosine at position 615 (Y615) was substituted with any of amino acids E, I, and T.

From these results, it turned out that a total of 19 amino acids are related to the content of allolactose.

(4) Mutation Sites in BgaD Type A

In the procedures shown in the above section (1-1), the designing of applying mutation to the loop structures located around the active center was made. On the other hand, the amino acids related to GOS synthesis has been reported for BgaD type A. In particular, it was reported that the substitution of the tryptophan at position 1540 (W1540) with alanine or phenylalanine led to a higher maximum yield of oligosaccharide synthesis (Non Patent Literature 1). Taking note of this report, the inventors assumed that the composition of GOSs to be produced could be altered by applying a mutation not only to an amino acid located around the active center that have been examined, but also to an amino acid present only in BgaD type A. On the basis of this assumption, the inventors actually attempted to perform saturation mutagenesis, in which the tryptophan at position 1540 (W1540) was substituted with 19 amino acids. In particular, W1540 was substituted with the other natural amino acids in a similar procedure as in the section (1-2), using as a template a plasmid coding a DNA for BgaD type A (SEQ ID NO. 5). In addition, the plasmid constructed was introduced into E. coli cells to express a variant enzyme. Furthermore, the GOS synthesis reaction was carried out in a similar way as in the section (1-4), and the contents of oligosaccharide components, tetrasaccharides and trisaccharides and higher saccharides, in the composition of GOSs produced were analyzed.

From the results of measurements of the composition of GOSs produced, the parent wild-type enzyme was found to have a content of tetrasaccharides of 10.4% and a content of trisaccharides and higher saccharides of 38.5%. On the basis of this observation, examination was made as to whether a change in the content of tetrasaccharides was observed in all the variants. From the results, it was found that 18 variant enzymes resulted in a higher content of tetrasaccharides than the wild-type enzyme (FIG. 6). Specifically, it turned out that the amount of production of tetrasaccharides was increased in the case of the following variants, in which the tryptophan at position 1540 (W1540) was substituted with any of amino acids A, C, D, E, F, G, H, I, K, L, M, N, P, Q, R, S, T, and V.

From the results described above, it turned out that an effect of increasing the amount of production of tetrasaccharides was observed by applying mutation not only to the loop structures around the active center, but also to the amino acid at position 1540.

3. Summary (1) Variants were found to have a decreased or increased hydrolytic activity for saccharides with a β-1,6-bond (mutations at 9 amino acid sites yielded 42 variants).

(2) The galacto-oligosaccharides produced by variants had altered degrees of polymerization and percentages of branched chains (mutation sites leading to an altered content of tetrasaccharides: 15 amino acid sites, yielding 41 variants; mutation sites leading to an altered percentage of branched chains: 19 amino acid sites, yielding 49 variants).

(3) Although the parent wild-type enzyme was capable of producing only oligosaccharides with a uniform composition, the use of variants would make it possible to produce various types of galacto-oligosaccharides separately as intended. Variants can be used, for example, for reproducing the components of mother's milk.

(4) It will be possible to construct even more useful variants by combining mutation sites that have been found to be effective by the above investigation.

<Identification of Positions for Effective Mutations 2>

From the results of further studies, there were further identified positions for effective mutations, whereby useful variants were obtained. In the following, the variants (variant enzymes) that were successfully obtained and their characteristics are described. Here, the variants in (A), (B), and (D) to (N) are derived from BgaD type D β-galactosidase (SEQ ID NO. 4), whereas the variants in (C) are derived from BgaD type A β-galactosidase (SEQ ID NO. 1).

(A) Variants meeting condition 3 and having undergone a single amino acid substitution (FIG. 7), in which the tryptophan at position 85 (W85) was substituted with glycine;

the phenylalanine at position 91 (F91) was substituted with alanine or isoleucine;

the tyrosine at position 103 (Y103) was substituted with glycine;

the tyrosine at position 134 (Y134) was substituted with glycine;

the tyrosine at position 153 (Y153) was substituted with glycine;

the proline at position 182 (P182) was substituted with tryptophan or tyrosine;

the tryptophan at position 186 (W186) was substituted with methionine;

the tyrosine at position 192 (Y192) was substituted with glycine;

the tyrosine at position 295 (Y295) was substituted with glycine;

the histidine at position 345 (H345) was substituted with glycine;

the glycine at position 349 (G349) was substituted with tryptophan;

the phenylalanine at position 402 (F402) was substituted with glycine;

the glutamine at position 407 (Q407) was substituted with isoleucine, leucine, methionine, valine, or tyrosine;

the glycine at position 479 (G479) was substituted with leucine, proline, or glutamine;

the glutamic acid at position 480 (E480) was substituted with asparagine;

the lysine at position 482 (K482) was substituted with methionine or valine;

the threonine at position 483 (T483) was substituted with glycine or serine;

the arginine at position 484 (R484) was substituted with phenylalanine, isoleucine, methionine, asparagine, or glutamine;

the glycine at position 485 (G485) was substituted with aspartic acid, asparagine, glutamine, or threonine;

the aspartic acid at position 486 (D486) was substituted with alanine, glutamic acid, phenylalanine, isoleucine, lysine, leucine, methionine, proline, glutamine, arginine, threonine, tryptophan, or tyrosine;

the lysine at position 487 (K487) was substituted with cysteine, glutamic acid, phenylalanine, histidine, isoleucine, leucine, asparagine, glutamine, arginine, threonine, valine, tryptophan, or tyrosine;

the valine at position 488 (V488) was substituted with glycine, isoleucine, leucine, arginine, serine, threonine, tryptophan, or tyrosine;

the tyrosine at position 496 (Y496) was substituted with glycine;

the serine at position 512 (S512) was substituted with cysteine, aspartic acid, glutamic acid, asparagine, proline, glutamine, or tryptophan;

the glutamic acid at position 513 (E513) was substituted with alanine, cysteine, aspartic acid, phenylalanine, glycine, histidine, lysine, leucine, methionine, asparagine, proline, glutamine, arginine, serine, threonine, or valine;

the asparagine at position 514 (N514) was substituted with glutamic acid, leucine, or lysine;

the asparagine at position 515 (N515) was substituted with alanine, aspartic acid, glutamic acid, glycine, isoleucine, leucine, proline, or valine;

the tyrosine at position 516 (Y516) was substituted with tryptophan;

the aspartic acid at position 517 (D517) was substituted with lysine or tryptophan;

the tyrosine at position 519 (Y519) was substituted with glycine;

the threonine at position 533 (T533) was substituted with glutamic acid;

the tyrosine at position 547 (Y547) was substituted with glycine;

the tyrosine at position 549 (Y549) was substituted with glycine;

the tyrosine at position 555 (Y555) was substituted with glycine;

the arginine at position 572 (R572) was substituted with cysteine, leucine, methionine, threonine, tryptophan, or tyrosine;

the threonine at position 573 (T573) was substituted with glutamic acid;

the tyrosine at position 598 (Y598) was substituted with histidine or asparagine;

the tyrosine at position 605 (Y605) was substituted with cysteine, aspartic acid, histidine, isoleucine, lysine, proline, arginine, or threonine;

the tyrosine at position 606 (Y606) was substituted with alanine, cysteine, aspartic acid, glutamic acid, phenylalanine, glycine, histidine, isoleucine, lysine, leucine, methionine, or serine;

the tyrosine at position 609 (Y609) was substituted with glutamic acid, asparagine, or serine;

the phenylalanine at position 616 (F616) was substituted with glycine;

the phenylalanine at position 624 (F624) was substituted with glycine;

the tryptophan at position 648 (W648) was substituted with glycine; and the tryptophan at position 650 (W650) was substituted with glycine.

(B) Variants meeting condition 4 and having undergone a single amino acid substitution (FIG. 8), in which the tryptophan at position 76 (W76) was substituted with glycine;

the glutamic acid at position 480 (E480) was substituted with glutamine;

the threonine at position 483 (T483) was substituted with tryptophan;

the glycine at position 485 (G485) was substituted with proline or threonine;

the arginine at position 484 (R484) was substituted with alanine, cysteine, aspartic acid, glycine, proline, serine, tyrosine, or lysine;

the lysine at position 487 (K487) was substituted with glycine or proline;

the valine at position 488 (V488) was substituted with proline;

the serine at position 512 (S512) was substituted with leucine or methionine;

the asparagine at position 514 (N514) was substituted with aspartic acid;

the asparagine at position 515 (N515) was substituted with phenylalanine, arginine, tryptophan, tyrosine, or lysine;

the glycine at position 569 (G569) was substituted with lysine, proline or valine; and the phenylalanine at position 596 (F596) was substituted with glycine.

(C) Variants having an increased content of tetrasaccharides and having undergone a single amino acid substitution (variants derived from BgaD type A β-galactosidase) (FIG. 9), in which the lysine at position 487 (K487) was substituted with glycine or proline;

the asparagine at position 514 (N514) was substituted with tryptophan; and the asparagine at position 515 (N515) was substituted with lysine or tryptophan.

(D) Variants having a combination of a substitution meeting condition 3 and a substitution meeting condition 5 (FIG. 10), in which the serine at position 188 was substituted with isoleucine and the asparagine at position 550 was substituted with phenylalanine (S188I_N550F);

the glutamine at position 407 was substituted with arginine and the asparagine at position 550 was substituted with phenylalanine (Q407R_N550F);

the tyrosine at position 449 was substituted with glutamine and the tyrosine at position 598 was substituted with histidine (Y449Q_Y598H); and the asparagine at position 550 was substituted with phenylalanine and the proline at position 602 was substituted with glutamine (N550F_P602Q).

(E) A variant having a combination of a substitution meeting condition 3 and a substitution meeting condition 6 (FIG. 10), in which the glutamine at position 407 was substituted with arginine and the tyrosine at position 449 was substituted with glutamic acid (Q407R_Y449E).

(F) A variant having a combination of a substitution meeting condition 4 and a substitution meeting condition 5 (FIG. 10), in which the asparagine at position 550 was substituted with phenylalanine and the tyrosine at position 598 was substituted with asparagine (N550F_Y598N).

(G) Variants having a combination of substitutions meeting condition 3 (FIG. 10), in which the proline at position 182 was substituted with leucine and the tyrosine at position 449 was substituted with glutamic acid (P182L_Y449E);

the proline at position 182 was substituted with leucine and the tyrosine at position 449 was substituted with glutamine (P182L_Y449Q);

the tyrosine at position 187 was substituted with leucine and the glutamine at position 407 was substituted with arginine (Y187L_Q407R);

the tyrosine at position 187 was substituted with leucine and the tyrosine at position 449 was substituted with glutamic acid (Y187L_Y449E);

the tyrosine at position 187 was substituted with leucine and the tyrosine at position 449 was substituted with glutamine (Y187L_Y449Q);

the tyrosine at position 187 was substituted with leucine and the serine at position 512 was substituted with cysteine (Y187L_S512C);

the tyrosine at position 187 was substituted with leucine and the serine at position 512 was substituted with asparagine (Y187L_S512N);

the tyrosine at position 187 was substituted with leucine and the serine at position 512 was substituted with threonine (Y187L_S512T);

the serine at position 188 was substituted with isoleucine and the glutamine at position 407 was substituted with arginine (S188I_Q407R);

the serine at position 188 was substituted with isoleucine and the tyrosine at position 449 was substituted with glutamine (S188I_Y449Q);

the serine at position 188 was substituted with isoleucine and the threonine at position 483 was substituted with glutamic acid (S188I_T483E);

the glutamine at position 407 was substituted with leucine and the serine at position 512 was substituted with valine (Q407L_S512V);

the glutamine at position 407 was substituted with arginine and the threonine at position 483 was substituted with glycine (Q407R_T483G);

the glutamine at position 407 was substituted with arginine and the tyrosine at position 449 was substituted with glutamine (Q407R_Y449Q);

the glutamine at position 407 was substituted with arginine and the asparagine at position 550 was substituted with serine (Q407R_N550S);

the tyrosine at position 449 was substituted with glutamine and the asparagine at position 550 was substituted with serine (Y449Q_N550S);

the lysine at position 487 was substituted with tryptophan and the serine at position 512 was substituted with threonine (K487W_S512T);

the lysine at position 487 was substituted with tryptophan and the aspartic acid at position 517 was substituted with lysine (K487W_D517K);

the lysine at position 487 was substituted with tryptophan and the asparagine at position 515 was substituted with glycine (K487W_N515G); and the lysine at position 487 was substituted with tryptophan and the aspartic acid at position 517 was substituted with tryptophan (K487W_D517W).

(H) A variant having a combination of substitutions meeting condition 4 (FIG. 10), in which the lysine at position 487 was substituted with proline and the asparagine at position 515 was substituted with arginine (K487P_N515R).

(I) Variants meeting condition 3 and having undergone two amino acid substitutions (FIG. 11), in which the phenylalanine at position 91 was substituted with serine and the glutamine at position 407 was substituted with methionine (F91S_Q407M);

the threonine at position 180 was substituted with valine and the tyrosine at position 187 was substituted with leucine (T180V_Y187L);

the threonine at position 180 was substituted with valine and the serine at position 188 was substituted with isoleucine (T180V_S188I);

the threonine at position 180 was substituted with valine and the glutamine at position 407 was substituted with arginine (T180V_Q407R);

the threonine at position 180 was substituted with valine and the tyrosine at position 449 was substituted with glutamic acid (T180V_Y449E);

the threonine at position 180 was substituted with valine and the threonine at position 483 was substituted with glycine (T180V_T483G);

the threonine at position 180 was substituted with valine and the serine at position 512 was substituted with valine (T180V_S512V);

the threonine at position 180 was substituted with valine and the asparagine at position 550 is substituted with phenylalanine (T180V_N550F);

the threonine at position 180 was substituted with valine and the tyrosine at position 615 was substituted with proline (T180V_Y615P);

the proline at position 182 was substituted with leucine and the arginine at position 376 was substituted with proline (P182L_R376P);

the proline at position 182 was substituted with tryptophan and the tyrosine at position 449 was substituted with glutamine (P182W_Y449Q);

the tyrosine at position 187 was substituted with leucine and the lysine at position 487 was substituted with alanine (Y187L_K487A);

the tyrosine at position 187 was substituted with leucine and the serine at position 512 was substituted with alanine (Y187L_S512A);

the tyrosine at position 187 was substituted with leucine and the threonine at position 533 was substituted with asparagine (Y187L_T533N);

the arginine at position 376 was substituted with proline and the glutamine at position 407 was substituted with leucine (R376P_Q407L);

the arginine at position 376 was substituted with proline and the tyrosine at position 449 was substituted with glutamine (R376P_Y449Q);

the arginine at position 376 was substituted with proline and the serine at position 512 was substituted with valine (R376P_S512V);

the arginine at position 376 was substituted with proline and the asparagine at position 550 was substituted with tryptophan (R376P_N550W);

the arginine at position 376 was substituted with proline and the asparagine at position 550 was substituted with tyrosine (R376P_N550Y);

the glutamine at position 407 was substituted with leucine and the threonine at position 533 was substituted with glutamic acid (Q407L_T533E);

the glutamine at position 407 was substituted with leucine and the tryptophan at position 570 was substituted with tyrosine (Q407L_W570Y);

the glutamine at position 407 was substituted with leucine and the tyrosine at position 615 was substituted with leucine (Q407L_Y615L);

the glutamine at position 407 was substituted with arginine and the tyrosine at position 615 was substituted with leucine (Q407R_Y615L);

the glutamine at position 407 was substituted with arginine and the tyrosine at position 615 was substituted with proline (Q407R_Y615P);

the tyrosine at position 449 was substituted with aspartic acid and the tyrosine at position 598 was substituted with phenylalanine (Y449D_Y598F);

the tyrosine at position 449 was substituted with glutamine and the threonine at position 533 was substituted with glutamic acid (Y449Q_T533E);

the tyrosine at position 449 was substituted with glutamine and the tyrosine at position 615 was substituted with glycine (Y449Q_Y615G);

the tyrosine at position 449 was substituted with glutamine and the tyrosine at position 615 was substituted with proline (Y449Q_Y615P);

the threonine at position 483 was substituted with glycine and the serine at position 512 was substituted with valine (T483G_S512V);

the threonine at position 483 was substituted with glycine and the asparagine at position 550 was substituted with serine (T483G_N550S);

the threonine at position 483 was substituted with glycine and the tyrosine at position 615 was substituted with leucine (T483G_Y615L);

the threonine at position 483 was substituted with glutamine and the proline at position 602 was substituted with glutamine (T483Q_P602Q);

the arginine at position 484 was substituted with histidine and the lysine at position 487 was substituted with histidine (R484H_K487H);

the arginine at position 484 was substituted with tryptophan and the lysine at position 487 was substituted with aspartic acid (R484W_K487D);

the arginine at position 484 was substituted with tryptophan and the threonine at position 575 is substituted with tryptophan (R484W_T575W);

the glycine at position 485 was substituted with lysine and the valine at position 488 was substituted with tryptophan (G485K_V488W);

the glycine at position 485 was substituted with lysine and the tyrosine at position 516 was substituted with tryptophan (G485K_Y516W);

the glycine at position 485 was substituted with lysine and the aspartic acid at position 517 was substituted with lysine (G485K_D517K);

the glycine at position 485 was substituted with lysine and the aspartic acid at position 517 was substituted with tryptophan (G485K_D517W);

the glycine at position 485 was substituted with lysine and the glycine at position 569 was substituted with tryptophan (G485K_G569W);

the glycine at position 485 was substituted with lysine and the glycine at position 571 was substituted with lysine (G485K_G571K);

the glycine at position 485 was substituted with lysine and the arginine at position 572 was substituted with tryptophan (G485K_R572W);

the glycine at position 485 was substituted with lysine and the threonine at position 573 was substituted with tryptophan (G485K_T573W);

the glycine at position 485 was substituted with tryptophan and the tyrosine at position 516 was substituted with tryptophan (G485W_Y516W);

the glycine at position 485 was substituted with tryptophan and the aspartic acid at position 517 was substituted with tryptophan (G485W_D517W);

the glycine at position 485 was substituted with tryptophan and the threonine at position 573 is substituted with lysine (G485W_T573K);

the glycine at position 485 was substituted with tryptophan and the threonine at position 573 was substituted with tryptophan (G485W_T573W);

the lysine at position 487 was substituted with alanine and the serine at position 512 was substituted with valine (K487A_S512V);

the lysine at position 487 was substituted with glycine and the asparagine at position 515 was substituted with glutamine (K487G_N515Q);

the lysine at position 487 was substituted with tryptophan and the threonine at position 573 was substituted with lysine (K487W_T573K);

the lysine at position 487 was substituted with tryptophan and the tryptophan at position 593 was substituted with phenylalanine (K487W_W593F);

the valine at position 488 was substituted with lysine and the asparagine at position 514 was substituted with lysine (V488K_N514K);

the valine at position 488 was substituted with lysine and the aspartic acid at position 517 was substituted with lysine (V488K_D517K);

the valine at position 488 was substituted with lysine and the glycine at position 569 was substituted with lysine (V488K_G569K);

the valine at position 488 was substituted with lysine and the glycine at position 569 was substituted with tryptophan (V488K_G569W);

the valine at position 488 was substituted with lysine and the arginine at position 572 was substituted with lysine (V488K_R572K);

the valine at position 488 was substituted with lysine and the threonine at position 573 was substituted with lysine (V488K_T573K);

the valine at position 488 was substituted with lysine and the threonine at position 573 was substituted with tryptophan (V488K_T573W);

the valine at position 488 was substituted with lysine and the tyrosine at position 516 was substituted with lysine (V488K_Y516K);

the valine at position 488 was substituted with lysine and the tyrosine at position 516 was substituted with tryptophan (V488K_Y516W);

the valine at position 488 was substituted with tryptophan and the asparagine at position 514 was substituted with tryptophan (V488W_N514W);

the valine at position 488 was substituted with tryptophan and the threonine at position 573 is substituted with tryptophan (V488W_T573W);

the glutamic acid at position 500 was substituted with alanine and the isoleucine at position 501 was substituted with alanine (E500A_I501A);

the serine at position 512 was substituted with valine and the asparagine at position 550 was substituted with serine (S512V_N550S);

the threonine at position 533 was substituted with glutamic acid and the asparagine at position 550 was substituted with serine (T533E_N550S);

the threonine at position 533 was substituted with glutamic acid and the tyrosine at position 615 was substituted with glycine (T533E_Y615G); and the tryptophan at position 570 was substituted with tyrosine and the tyrosine at position 615 was substituted with leucine (W570Y_Y615L).

(J) Variants meeting condition 4 and having undergone two amino acid substitutions (FIG. 11), in which the phenylalanine at position 91 was substituted with valine and the glutamic acid at position 513 was substituted with glycine (F91V_E513G);

the threonine at position 180 was substituted with valine and the threonine at position 483 was substituted with lysine (T180V_T483K);

the threonine at position 180 was substituted with valine and the tyrosine at position 598 was substituted with asparagine (T180V_Y598N);

the threonine at position 180 was substituted with valine and the tyrosine at position 615 was substituted with glycine (T180V_Y615G);

the proline at position 182 was substituted with leucine and the tyrosine at position 615 was substituted with leucine (P182L_Y615L);

the arginine at position 376 was substituted with proline and the tyrosine at position 598 was substituted with asparagine (R376P_Y598N);

the glutamine at position 407 was substituted with leucine and the threonine at position 483 was substituted with lysine (Q407L_T483K);

the glutamine at position 407 was substituted with leucine and the lysine at position 487 was substituted with proline (Q407L_K487P);

the glutamine at position 407 was substituted with leucine and the tyrosine at position 615 was substituted with glycine (Q407L_Y615G);

the tyrosine at position 449 was substituted with glutamic acid and the lysine at position 487 was substituted with alanine (Y449E_K487A);

the tyrosine at position 449 was substituted with glutamic acid and the lysine at position 487 was substituted with proline (Y449E_K487P);

the threonine at position 483 was substituted with glycine and the lysine at position 487 was substituted with alanine (T483G_K487A);

the threonine at position 483 was substituted with glycine and the threonine at position 533 was substituted with glutamic acid (T483G_T533E);

the threonine at position 483 was substituted with glycine and the tyrosine at position 615 was substituted with glycine (T483G_Y615G);

the threonine at position 483 was substituted with methionine and the lysine at position 487 was substituted with alanine (T483M_K487A);

the threonine at position 483 was substituted with methionine and the lysine at position 487 was substituted with glycine (T483M_K487G);

the threonine at position 483 was substituted with methionine and the lysine at position 487 was substituted with proline (T483M_K487P);

the arginine at position 484 was substituted with histidine and the lysine at position 487 was substituted with aspartic acid (R484H_K487D);

the arginine at position 484 was substituted with lysine and the glutamic acid at position 513 was substituted with tryptophan (R484K_E513W);

the arginine at position 484 was substituted with lysine and the asparagine at position 514 was substituted with lysine (R484K_N514K);

the arginine at position 484 was substituted with lysine and the asparagine at position 514 was substituted with tryptophan (R484K_N514W);

the arginine at position 484 was substituted with lysine and the asparagine at position 515 was substituted with lysine (R484K_N515K);

the arginine at position 484 was substituted with lysine and the asparagine at position 515 was substituted with tryptophan (R484K_N515W);

the arginine at position 484 was substituted with lysine and the aspartic acid at position 517 was substituted with tryptophan (R484K_D517W);

the arginine at position 484 was substituted with lysine and the glycine at position 569 was substituted with lysine (R484K_G569K);

the arginine at position 484 was substituted with lysine and the glycine at position 571 was substituted with lysine (R484K_G571K);

the arginine at position 484 was substituted with lysine and the arginine at position 572 was substituted with lysine (R484K_R572K);

the arginine at position 484 was substituted with lysine and the arginine at position 572 was substituted with tryptophan (R484K_R572W);

the arginine at position 484 was substituted with lysine and the threonine at position 573 was substituted with lysine (R484K_T573K);

the arginine at position 484 was substituted with lysine and the threonine at position 573 was substituted with tryptophan (R484K_T573W);

the arginine at position 484 was substituted with lysine and the tyrosine at position 516 was substituted with lysine (R484K_Y516K);

the arginine at position 484 was substituted with tryptophan and the asparagine at position 515 was substituted with lysine (R484W_N515K);

the glycine at position 485 was substituted with aspartic acid and the lysine at position 487 was substituted with histidine (G485D_K487H);

the glycine at position 485 was substituted with lysine and the lysine at position 487 was substituted with histidine (G485K_K487H);

the glycine at position 485 was substituted with lysine and the glycine at position 569 was substituted with lysine (G485K_G569K);

the glycine at position 485 was substituted with lysine and the asparagine at position 514 was substituted with lysine (G485K_N514K);

the glycine at position 485 was substituted with lysine and the asparagine at position 515 was substituted with lysine (G485K_N515K);

the glycine at position 485 was substituted with lysine and the asparagine at position 515 was substituted with tryptophan (G485K_N515W);

the glycine at position 485 was substituted with arginine and the lysine at position 487 was substituted with aspartic acid (G485R_K487D);

the glycine at position 485 was substituted with tryptophan and the glutamic acid at position 513 was substituted with tryptophan (G485W_E513W);

the glycine at position 485 was substituted with tryptophan and the asparagine at position 515 was substituted with lysine (G485W_N515K);

the glycine at position 485 was substituted with tryptophan and the asparagine at position 515 was substituted with tryptophan (G485W_N515W);

the lysine at position 487 was substituted with alanine and the serine at position 531 was substituted with alanine (K487A_S531A);

the lysine at position 487 was substituted with alanine and the tryptophan at position 593 was substituted with phenylalanine (K487A_W593F);

the lysine at position 487 was substituted with alanine and the tyrosine at position 615 was substituted with leucine (K487A_Y615L);

the lysine at position 487 was substituted with tryptophan and the asparagine at position 514 was substituted with lysine (K487W_N514K);

the lysine at position 487 was substituted with tryptophan and the asparagine at position 514 was substituted with tryptophan (K487W_N514W);

the lysine at position 487 was substituted with tryptophan and the tyrosine at position 516 was substituted with tryptophan (K487W_Y516W);

then lysine at position 487 was substituted with tryptophan and the glycine at position 569 was substituted with lysine (K487W_G569K);

the lysine at position 487 was substituted with tyrosine and the asparagine at position 515 is substituted with phenylalanine (K487Y_N515F);

the lysine at position 487 was substituted with tyrosine and the asparagine at position 515 was substituted with tryptophan (K487Y_N515W);

the valine at position 488 was substituted with lysine and the asparagine at position 515 was substituted with lysine (V488K_N515K);

the valine at position 488 was substituted with lysine and the asparagine at position 515 was substituted with tryptophan (V488K_N515W);

the valine at position 488 was substituted with tryptophan and the asparagine at position 515 was substituted with lysine (V488W_N515K);

the valine at position 488 was substituted with tryptophan and the asparagine at position 515 was substituted with tryptophan (V488W_N515W);

the valine at position 488 was substituted with tyrosine and the asparagine at position 515 was substituted with tryptophan (V488Y_N515W);

the asparagine at position 550 was substituted with serine and the tyrosine at position 598 was substituted with asparagine (N550S_Y598N);

the asparagine at position 550 was substituted with serine and the tyrosine at position 615 was substituted with glycine (N550S_Y615G);

the asparagine at position 550 was substituted with serine and the tyrosine at position 615 was substituted with leucine (N550S_Y615L); and the asparagine at position 550 was substituted with serine and the tyrosine at position 615 was substituted with proline (N550S_Y615P).

(K) Variants meeting condition 3 and having undergone three or four amino acid substitutions (FIG. 12), in which the arginine at position 484 was substituted with alanine, the glycine at position 485 was substituted with alanine, and the lysine at position 487 was substituted with aspartic acid (R484A_G485A_K487D);

the arginine at position 484 was substituted with aspartic acid, the glycine at position 485 was substituted with aspartic acid, and the lysine at position 487 was substituted with aspartic acid (R484D_G485D_K487D);

the glycine at position 485 was substituted with arginine, the aspartic acid at position 486 was substituted with arginine, and the lysine at position 487 was substituted with arginine (G485R_D486R_K487R);

the arginine at position 484 was substituted with alanine, the glycine at position 485 was substituted with alanine, the aspartic acid at position 486 was substituted with alanine, and the lysine at position 487 was substituted with alanine (R484A_G485A_D486A_K487A); and the arginine at position 484 was substituted with alanine, the glycine at position 485 was substituted with alanine, the aspartic acid at position 486 was substituted with proline, and the lysine at position 487 was substituted with proline (R484A_G485A_D486P_K487P).

(L) Variants meeting condition 4 and having undergone three or four amino acid substitutions (FIG. 12), in which the arginine at position 484 was substituted with alanine, the glycine at position 485 was substituted with alanine, and the lysine at position 487 was substituted with aspartic acid (R484A_G485A_K487D);

the arginine at position 484 was substituted with cysteine, the aspartic acid at position 486 was substituted with histidine, and the lysine at position 487 was substituted with arginine (R484C_D486H_K487R);

the glycine at position 485 was substituted with arginine, the aspartic acid at position 486 was substituted with tryptophan, and the lysine at position 487 was substituted with tryptophan (G485R_D486W_K487W);

the glycine at position 485 was substituted with arginine, the aspartic acid at position 486 was substituted with alanine, and the lysine at position 487 was substituted with alanine (G485R_D486A_K487A);

the glycine at position 485 was substituted with arginine, the aspartic acid at position 486 was substituted with proline, and the lysine at position 487 was substituted with proline (G485R_D486P_K487P);

the arginine at position 484 was substituted with alanine, the glycine at position 485 was substituted with alanine, the aspartic acid at position 486 was substituted with alanine, and the lysine at position 487 was substituted with alanine (R484A_G485A_D486A_K487A);

the arginine at position 484 was substituted with alanine, the glycine at position 485 was substituted with alanine, the aspartic acid at position 486 was substituted with arginine, and the lysine at position 487 was substituted with arginine (R484A_G485A_D486R_K487R);

the arginine at position 484 was substituted with aspartic acid, the glycine at position 485 was substituted with aspartic acid, the aspartic acid at position 486 was substituted with arginine, and the lysine at position 487 was substituted with arginine (R484D_G485D_D486R_K487R);

the arginine at position 484 was substituted with aspartic acid, the glycine at position 485 was substituted with aspartic acid, the aspartic acid at position 486 was substituted with proline, and the lysine at position 487 was substituted with proline (R484D_G485D_D486P_K487P);

the arginine at position 484 was substituted with aspartic acid, the glycine at position 485 was substituted with aspartic acid, the aspartic acid at position 486 was substituted with alanine, and the lysine at position 487 was substituted with alanine (R484D_G485D_D486A_K487A);

the arginine at position 484 was substituted with aspartic acid, the glycine at position 485 was substituted with aspartic acid, the aspartic acid at position 486 was substituted with tryptophan, and the lysine at position 487 was substituted with tryptophan (R484D_G485D_D486W_K487W); and the arginine at position 484 was substituted with proline, the glycine at position 485 was substituted with proline, the aspartic acid at position 486 was substituted with arginine, and the lysine at position 487 was substituted with arginine (R484P_G485P_D486R_K487R).

(M) Insertion or deletion variants meeting condition 3 (FIG. 13), which are represented by Δ484-487,
N514-F-F-N515,
N514-W-W-N515,
P604-W-W-Y605,
P604-A-A-A-A-Y605, and
P604-F-F-F-F-Y605.

(N) Insertion or deletion variants meeting condition 4 (FIG. 13), which are represented by Δ485_D486H,
Δ485-486_K487R,
Δ485-486_R484W_K487W,
Δ485-486_R484P_K487P,
R484-A-A-G485,
R484-F-F-G485,
R484-K-K-G485,
R484-P-P-G485,
R484-R-R-G485,
R484-S-S-G485,
R484-W-W-G485,
G485-S-S-S-D486,
R484-A-A-A-A-G485,
R484-D-D-D-D-G485,
R484-F-F-F-F-G485,
R484-P-P-P-P-G485,
R484-R-R-R-R-G485,
R484-S-S-S-S-G485,
R484-W-W-W-W-G485,
R484-A-A-A-A-A-A-A-A-G485,
R484-D-D-D-D-D-D-D-D-G485,
R484-F-F-F-F-F-F-F-F-G485,
R484-K-K-K-K-K-K-K-K-G485, and
R484-P-P-P-P-P-P-P-P-G485.

INDUSTRIAL APPLICABILITY

The modified enzymes of the present invention exhibit enzymological properties different from those of the parent wild-type enzymes thereof. Taking advantage of these characteristics, it is envisaged that the modified enzymes will be used to produce various galacto-oligosaccharides separately as intended. In particular, it can be expected that the present invention is used for reproducing the profile of oligosaccharides in mother's milk, which has not been achievable using wild-type enzymes alone. In addition, the modified enzymes of the present invention will be expected to be used for production (synthesis) of oligosaccharides. Furthermore, the present invention can also be used for production and processing of pharmaceutical products and supplements for lactose-intolerant patients, production and processing of dairy products (for example, processed milk products such as lactose-reduced milk, powdered milk such as skim milk and nursing powdered milk, yogurts, and others), and production and processing of medical foods.

The present invention should not be limited in any way to the description of the above-described embodiments and examples of the invention. The present invention also includes a variety of modified embodiments within the scope that one skilled in the art could easily arrive without departing from the description of the scope of claims. The contents of articles, published patent applications, patent publications, and others that are expressly provided are incorporated in their entire content by citation.

The invention claimed is:

1. A modified β-galactosidase consisting of an amino acid sequence that has at least 98% sequence identity to the amino acid sequence of SEQ ID NO. 1, 2, 3, or 4, wherein the modified β-galactosidase comprises one or more of the following substitutions: wherein the tyrosine at position 187 (Y187) is aspartic acid or leucine; the aspartic acid at position 486 (D486) is alanine, glutamic acid, phenylalanine, isoleucine, lysine, leucine, methionine, proline, glutamine, arginine, threonine, tryptophan, or tyrosine; the lysine at position 487 (K487) is cysteine, glutamic acid, phenylalanine, histidine, isoleucine, leucine, asparagine, glutamine, arginine, threonine, valine, tryptophan, or tyrosine; the serine at position 512 (S512) is phenylalanine, threonine, valine, cysteine, aspartic acid, glutamic acid, asparagine, proline, glutamine, or tryptophan; the glutamic acid at position 513 (E513) is alanine, cysteine, aspartic acid, phenylalanine, glycine, histidine, lysine, leucine, methionine, asparagine, proline, glutamine, arginine, serine, threonine, or valine; and the arginine at position 572 (R572) is cysteine, leucine, methionine, threonine, tryptophan, or tyrosine, relative to SEQ ID NO. 1, 2, 3, or 4, wherein the modified β-galactosidase in an oligosaccharide synthesis reaction with a concentrated solution of lactose as the substrate, produces oligosaccharides in which the content of tetrasaccharides is smaller than that of the oligosaccharides produced by using the parent wild-type β-galactosidase.

2. A polynucleotide encoding the modified β-galactosidase of claim 1.

3. A recombinant DNA comprising the polynucleotide of claim 2.

4. A microorganism carrying the recombinant DNA of claim 3.

5. An enzyme preparation comprising the modified β-galactosidase of claim 1.

6. A method for producing an oligosaccharide, the method comprising contacting the modified β-galactosidase of claim 1 with a disaccharide, an oligosaccharide, or a polysaccharide having at least one of β-1,3-bond, β-1,4-bond, β-1,6-bond, or a combination thereof.

* * * * *